United States Patent
Driebe et al.

(10) Patent No.: US 11,572,591 B2
(45) Date of Patent: Feb. 7, 2023

(54) **METHODS AND ASSAYS FOR SUBTYPING *STAPHYLOCOCCUS AUREUS* CLONAL COMPLEX 8 STRAINS**

(71) Applicants: THE TRANSLATIONAL GENOMICS RESEARCH INSTITUTE, Phoenix, AZ (US); ARIZONA BOARD OF REGENTS ON BEHALF OF NORTHERN ARIZONA UNIVERSITY, Flagstaff, AZ (US); CENTERS FOR DISEASE CONTROL AND PREVENTION (CDC), Atlanta, GA (US)

(72) Inventors: Elizabeth Driebe, Flagstaff, AZ (US); Jolene Bowers, Flagstaff, AZ (US); David Engelthaler, Flagstaff, AZ (US); Paul Keim, Flagstaff, AZ (US); Brandi Limbago, Atlanta, GA (US); James K. Rasheed, Atlanta, GA (US); Linda McDougal, Atlanta, GA (US); Valerie S. Albrecht, Atlanta, GA (US)

(73) Assignees: The Translational Genomics Research Institute, Phoenix, AZ (US); Arizona Board of Regents on behalf of Northern Arizona University, Flagstaff, AZ (US); Centers for Disease Control and Prevention, Bethesda, MD (US)

( * ) Notice: Subject to any disclaimer, the term of this patent is extended or adjusted under 35 U.S.C. 154(b) by 0 days.

(21) Appl. No.: 16/607,716

(22) PCT Filed: Apr. 26, 2018

(86) PCT No.: PCT/US2018/009666
§ 371 (c)(1),
(2) Date: Oct. 23, 2019

(87) PCT Pub. No.: WO2018/200887
PCT Pub. Date: Nov. 1, 2018

(65) Prior Publication Data
US 2020/0165663 A1    May 28, 2020

Related U.S. Application Data

(60) Provisional application No. 62/490,460, filed on Apr. 26, 2017.

(51) Int. Cl.
*C12Q 1/689*  (2018.01)
*C12Q 1/686*  (2018.01)
(Continued)

(52) U.S. Cl.
CPC ............ *C12Q 1/689* (2013.01); *C12Q 1/686* (2013.01); *A61K 31/496* (2013.01);
(Continued)

(58) Field of Classification Search
CPC ...................................................... C12Q 1/689
See application file for complete search history.

(56) References Cited

U.S. PATENT DOCUMENTS 4,683,195 A    7/1987  Mullis et al.
4,683,202 A    7/1987  Mullis
(Continued)

FOREIGN PATENT DOCUMENTS

EP    0070685 A2    1/1983
WO    1994/016108 A1    7/1994
(Continued)

OTHER PUBLICATIONS

Challagundla, L. et al. mBio 9(1):e2016-17 (Jan. 2018). (Year: 2018).*

(Continued)

*Primary Examiner* — Diana B Johannsen
(74) *Attorney, Agent, or Firm* — Rodney J. Fuller; Booth Udall Fuller, PLC

(57) ABSTRACT

The present invention provides a method of detecting *Staphylococcus aureus* in a subject, by contacting a sample obtained from the subject with at least one detectably (Continued)

labeled probe of the invention or detecting in the sample identity to a sequence of the invention. The invention is also directed to kits, microarrays and detectable *Staphylococcus aureus* polynucleotide probes useful in detecting the presence of *Staphylococcus aureus*.

20 Claims, 5 Drawing Sheets
Specification includes a Sequence Listing.

(51) Int. Cl.
```
A61K 31/505      (2006.01)
A61K 31/635      (2006.01)
A61K 38/14       (2006.01)
A61K 31/65       (2006.01)
A61K 31/5377     (2006.01)
A61K 31/496      (2006.01)
```
(52) U.S. Cl.
CPC ........ *A61K 31/505* (2013.01); *A61K 31/5377* (2013.01); *A61K 31/635* (2013.01); *A61K 31/65* (2013.01); *A61K 38/14* (2013.01); *C12Q 2531/113* (2013.01); *C12Q 2561/113* (2013.01); *C12Q 2600/158* (2013.01)

(56) References Cited

U.S. PATENT DOCUMENTS

| | | | |
|---|---|---|---|
| 4,965,188 | A | 10/1990 | Mullis et al. |
| 5,035,996 | A | 7/1991 | Hartley |
| 5,210,015 | A | 5/1993 | Gelfand et al. |
| 5,487,972 | A | 1/1996 | Gelfand et al. |
| 5,804,375 | A | 9/1998 | Gelfand et al. |
| 5,854,033 | A | 12/1998 | Lizardi |
| 6,214,979 | B1 | 4/2001 | Gelfand et al. |
| RE39,007 | E | 3/2006 | Dattagupta et al. |
| 7,608,276 | B2 * | 10/2009 | Masignani ............ A61P 31/14 424/243.1 |
| 2004/0265897 | A1 | 12/2004 | Lizardi |
| 2007/0020746 | A1 | 1/2007 | Kunsch et al. |
| 2015/0259727 | A1 | 9/2015 | Keim et al. |

FOREIGN PATENT DOCUMENTS

| | | |
|---|---|---|
| WO | 2006/081222 A2 | 8/2006 |
| WO | 2006/087574 A2 | 8/2006 |
| WO | 2010/149159 A1 | 12/2010 |
| WO | 2017/020967 A1 | 2/2017 |

OTHER PUBLICATIONS

Straub, L. et al. PNAS E10596-E10604 (Nov. 2017). (Year: 2017).*
Chadwick, Sean G. et al., "Detection of Epidemic USA300 Community-Associated Methicillin-Resistant *Staphylococcus aureus* Strains by Use of a Single Allele-Specific PCR Assay Targeting a Novel Polymorphism of *Staphylococcus aureus* pbp 3", Journal of Clinical Microbiology, 51(8):2541-2550 (Aug. 2013).
Engelthaler, David M. et al., "Rapid and robust phylotyping of spa t003, a dominant MRSA clone in Luxembourg and other European countries", BMC Infectious Diseases, 13(339):1-10 (2013).
Fiandaca, M. J., et al. Self-reporting PNA/DNA primers for PCR analysis. Genome Res 2001; 11(4):609-613.
Nazarenko, I., et al. Multiplex quantitative PCR using self-quenched primers labeled with a single fluorophore. Nucleic Acids Res 2002; 30(9):e37.
Whitcombe, D., et al. Detection of PCR products using self-probing amplicons and fluorescence. Nat Biotechnol 1999; 17(8):804-807.
Nazarenko, I. A., et al. A closed tube format for amplification and detection of DNA based on energy transfer. Nucleic Acids Res 1997; 25(12):2516-2521.
Todd, A. V., et al. DzyNA-PCR: Use of DNAzymes to detect and quantify nucleic acid sequences in a real-time fluorescent format. Clin Chem 2000; 46(5):625-630.
Holland, P. M., et al. Detection of specific polymerase chain reaction product by utilizing the 5'—3' exonuclease activity of Thermus aquaticus DNA polymerase. Proc Natl Acad Sci USA 1991; 88(16):7276-7280.
Heid, et al. Real time quantitative PCR. Genome Research 1996; 6(10):986-994.
Santalucia, J., et al. Improved nearest-neighbor parameters for predicting DNA duplex stability. Biochemistry 1996; 35(11):3555-3562.
Bustin, S. A., et al. The MIQE Guidelines: Minimum Information for Publication of Quantitative Real-Time PCR Experiments. Clinical Chemistry 2009; 55(4):611-622.
Bal, A. M., et al. Genomic insights into the emergence and spread of international clones of healthcare-, community-and livestock-associated meticillin-resistant *Staphylococcus aureus*: blurring of the traditional definitions. J Glob Antimicrob Resist 2016; 6:95-101.
Carrel, M., et al. USA300 methicillin-resistant *Staphylococcus aureus*, United States, 2000-2013. Emerg Infect Dis 2014; 21:1973-1980.
Diekema, D. J., et al. Continued emergence of USA300 methicillin-resistant *Staphylococcus aureus* in the United States: results from a nationwide surveillance study. Infect Control Hosp Epidemiol 2014; 35:285-292.
Albrecht, V. S., et al. *Staphylococcus aureus* colonization and strain type at various body sites among patients with a closed abscess and uninfected controls at U.S. emergency departments. J Clin Microbiol 2015; 53:3478-3484.
David, M. Z., et al. Methicillin-susceptible *Staphylococcus aureus* as a predominantly healthcare-associated pathogen: a possible reversal of roles? PLoS One 2011; 6:e18217.
Miko, B. A., et al. Molecular characterization of methicillin-susceptible *Staphylococcus aureus* clinical isolates in the United States, 2004 to 2010. J Clin Microbiol 2013; 51:874-879.
Li, M., et al. Evolution of virulence in epidemic community-associated methicillin-resistant *Staphylococcus aureus*. Proc Natl Acad Sci U S A 2009; 106(14):5883-5888.
Harris, S. R., et al. Evolution of MRSA during hospital transmission and intercontinental spread. Science 2010; 327(5964):469-474.
Wang, Z., et al. Comparative genomics of methicillin-resistant *Staphylococcus aureus* ST239: distinct geographical variants in Beijing and Hong Kong. BMC Genomics 2014; 15:529.
Robinson, D. A., et al. Evolution of *Staphylococcus aureus* by large chromosomal replacements. J Bacteriol 2004; 186(4):1060-1064.
Chambers, H. F., et al. Waves of resistance: *Staphylococcus aureus* in the antibiotic era. Nat Rev Microbiol 2009; 7(9):629-641.
Enright, M. C., et al. The evolutionary history of methicillin-resistant *Staphylococcus aureus* (MRSA). Proc Natl Acad Sci U S A 2002; 99(11):7687-7692.
Coombs, G. W., et al. Methicillin-resistant *Staphylococcus aureus* clones, Western Australia. Emerg Infect Dis 2006; 12(2):241-247.
Planet, P. J., et al. Parallel epidemics of community-associated methicillin-resistant *Staphylococcus aureus* USA300 infection in North and South America. J Infect Dis 2015; 212(12):1874-1882.
McDougal, L. K., et al. Pulsed-field gel electrophoresis typing of oxacillin-resistant *Staphylococcus aureus* isolates from the United States: establishing a national database. J Clin Microbiol 2003; 41(11):5113-5120.
David, M. Z., et al. Comparing pulsed-field gel electrophoresis with multilocus sequence typing, spa typing, staphylococcal cassette chromosome mec (SCCmec) typing, and PCR for Panton-Valentine leukocidin, arcA, and ppp3 in methicillin-resistant *Staphylococcus aureus* isolates at a U.S. Medical Center. J Clin Microbiol 2013; 51(3):814-819.
Nubel, U., et al. Frequent emergence and limited geographic dispersal of methicillin-resistant *Staphylococcus aureus* Proc Natl Acad Sci U S A 2008; 105(37):14130-14135.
Driebe, E. M., et al. Using whole genome analysis to examine recombination across diverse sequence types of *Staphylococcus aureus*. PLoS One 2015; 10(7):e0130955.

(56) References Cited

OTHER PUBLICATIONS

Strommenger, B., et al. Evolution of methicillin-resistant *Staphylococcus aureus* towards increasing resistance. J Antimicrob Chemother 2014; 69:616-622.
Monecke, S., et al. A field guide to pandemic, epidemic and sporadic clones of methicillin-resistant *Staphylococcus aureus*. PLoS One 2011; 6(4):e17936.
Campanile, F., et al. Hospital-associated methicillin-resistant *Staphylococcus aureus* (HA-MRSA) in Italy. Ann Clin Microbiol Antimicrob 2009; 8:22.
Jamrozy, D. M., et al. Pan-genomic perspective on the evolution of the *Staphylococcus aureus* USA300 epidemic. Microb Genom 2016; 2(5):e000058.
Benson, M. A., et al. Evolution of hypervirulence by a MRSA clone through acquisition of a transposable element. Mol Microbiol 2014; 93(4):664-681.
Boyle-Vavra, S., et al. USA300 and USA500 clonal lineages of *Staphylococcus aureus* do not produce a capsular polysaccharide due to conserved mutations in the cap5 locus mBio 2015; 6:e02585-14.
Keim, P., et al. Anthrax molecular epidemiology and forensics: using the appropriate marker for different evolutionary scales. Infect Genet Evol 2004; 4(3):205-213.
Nimmo, G. R. USA300 abroad: global spread of a virulent strain of community-associated methicillin-resistant *Staphylococcus aureus*. Clin Microbiol Infect 2012; 18(8):725-734.
Aanensen, D. M., et al. Whole-genome sequencing for routine pathogen surveillance in public health: a population snapshot of invasive *Staphylococcus aureus* in Europe. mBio 2016; 7:e00444-16.
Rossi, F., et al. Transferable vancomycin resistance in a community-associated MRSA lineage. N Engl J Med 2014; 370:1524-1531.
Goering, R. V., et al. Epidemiologic distribution of the arginine catabolic mobile element among selected methicillin-resistant and methicillin-susceptible *Staphylococcus aureus* isolates. J Clin Microbiol 2007; 45(6):1981-1984.
Christianson, S., et al. Comparative genomics of Canadian epidemic lineages of methicillin-resistant *Staphylococcus aureus*. J Clin Microbiol 2007; 45(6):1904-1911.
Frisch, M. B., et al. Invasive methicillin-resistant *Staphylococcus aureus* USA500 strains from the U.S. Emerging Infections Program constitute three geographically distinct lineages. mSphere 2018; 3(3):e00571-17.
Noto, M. J., et al. Gene acquisition at the insertion site for SCCmec, the genomic island conferring methicillin resistance in *Staphylococcus aureus*. J Bacteriol 2008; 190(4):1276-1283.
Diep, B. A., et al. Roles of 34 virulence genes in the evolution of hospital-and community-associated strains of methicillin-resistant *Staphylococcus aureus*. J Infect Dis 2006; 193(11):1495-1503.
Planet, P. J., et al. Emergence of the epidemic methicillin-resistant *Staphylococcus aureus* strain USA300 coincides with horizontal transfer of the arginine catabolic mobile element and speG-mediated adaptations for survival on skin. mBio 2013; 4(6):e00889-13.
Roe, C. C., et al. Whole genome SNP typing to investigate methicillin-resistant *Staphylococcus aureus* carriage in a health care provider as the source of multiple surgical site infections. Hereditas 2016; 153:11.
Holden, M. T., et al. A genomic portrait of the emergence, evolution, and global spread of a methicillin-resistant *Staphylococcus aureus* pandemic. Genome Res 2013; 23(4):653-664.
Kurt, K., et al. Subpopulations of *Staphylococcus aureus* clonal complex 121 are associated with distinct clinical entities. PLoS One 2013; 8(3):e58155.
McAdam, P. R., et al. Molecular tracing of the emergence, adaptation, and transmission of hospital-associated methicillin-resistant *Staphylococcus aureus*. Proc Natl Acad Sci U S A 2012; 109(23):9107-9112.

See, I., et al. Public health importance of methicillin-sensitive *Staphylococcus aureus* (MSSA): results from pilot surveillance in five counties, 2014-2015. Open Forum Infect Dis 2015; 2:1121; Abstract Only.
Grundmann, H., et al. Geographic distribution of *Staphylococcus aureus* causing invasive infections in Europe: a molecular-epidemiological analysis. PLoS Med 2010; 7(1):e1000215.
Barbier, F., et al. Methicillin-resistant coagulase-negative staphylococci in the community: high homology of SCCmec IVa between *Staphylococcus epidermidis* and major clones of methicillin-resistant *Staphylococcus aureus*. J Infect Dis 2010; 202(2):270-281.
Huang, J., et al. Prevalence of fusB in *Staphylococcus aureus* clinical isolates. J Med Microbiol 2013; 62:1199-1203.
Zheng, B., et al. Severe infective endocarditis with systemic embolism due to community associated methicillin-resistant *Staphylococcus aureus* ST630. Braz J Infect Dis 2015; 19(1):85-89.
Gu, F. F., et al. Characterization of *Staphylococcus aureus* isolated from non-native patients with skin and soft tissue infections in Shanghai. PLoS One 2015; 10:e0123557.
Jackson, B. R., et al. Implementation of nationwide real-time whole-genome sequencing to enhance listeriosis outbreak detection and investigation. Clin Infect Dis 2016; 63(3):380-386.
Bergholz, T. M., et al. Determination of evolutionary relationships of outbreak-associated Listeria monocytogenes strains of serotypes 1/2a and 1/2b by whole-genome sequencing. Appl Environ Microbiol 2016; 82(3):928-938.
Deng, X., et al. Comparative analysis of subtyping methods against a whole-genome-sequencing standard for *Salmonella enterica* serotype Enteritidis J Clin Microbiol 2015; 53(1):212-218.
Fenover, F. C., et al. Characterization of a strain of community-associated methicillin-resistant *Staphylococcus aureus* widely disseminated in the United States. J Clin Microbiol 2006; 44(1):108 118.
Sahl, J. W., et al. NASP: an accurate, rapid method for the identification of SNPs in WGS datasets that supports flexible input and output formats. Microb Genom 2016; 2(8):e000074.
Bowers, J. R., et al. KlebSeq: a diagnostic tool for surveillance, detection, and monitoring of Klebsiella pneumoniae. J Clin Microbiol 2016; 54(10):2582-2596.
Bowers, J. R., et al. Genomic analysis of the emergence and rapid global dissemination of the clonal group 258 Klebsiella pneumoniae pandemic. PLoS One 2015; 10(7):e0133727.
Engelthaler, D. M., et al. Hypervirulent emm59 clone in invasive group A streptococcus outbreak, southwestern United States. Emerg Infect Dis 2016; 22(4):734-738.
Sanches, I. S., et al. Evidence for the geographic spread of a methicillin-resistant *Staphylococcus aureus* clone between Portugal and Spain. J Clin Microbiol 1995; 33(5):1243-1246.
De Lencastre, H., et al. Archaic strains of methicillin-resistant *Staphylococcus aureus*: molecular and microbiological properties of isolates from the 1960s in Denmark. Microb Drug Resist 2000; 6(1):1-10.
Glaser, P., et al. Demography and intercontinental spread of the USA300 community-acquired methicillin-resistant *Staphylococcus aureus* lineage. mBio 2016; 7(1):e02183-15.
Uhlemann, A. C., et al. Molecular tracing of the emergence, diversification, and transmission of S. *aureus* sequence type 8 in a New York community. Proc Natl Acad Sci U S A 2014; 111(18):6738-3743.
Stegger, M., et al. Origin and evolution of European community-acquired methicillin-resistant *Staphylococcus aureus*. mBio 2014; 5(5):e01044-14.
McKenna, A., et al. The Genome Analysis Toolkit: a MapReduce framework for analyzing next-generation DNA sequencing data. Genome Res 2010; 20(9):1297-1303.
Delcher, A. L., et al. Using MUMmer to identify similar regions in large sequence sets. Curr Protoc Bioinformatics 2003; Chapter 10:Unit 10.3.
Nguyen, L. T., et al. IQ-TREE: a fast and effective stochastic algorithm for estimating maximum-likelihood phylogenies. Mol Biol Evol 2015; 32(1):268-274.

(56) References Cited

OTHER PUBLICATIONS

Letunic, I., et al. Interactive tree of life v2: online annotation and display of phylogenetic trees made easy. Nucleic Acids Res 2011; 39(Web Server Issue):W475-W478.

Inouye, M., et al. SRST2: rapid genomic surveillance for public health and hospital microbiology labs. Genome Med 2014; 6(11):90.

Chen, L., et al. Multiplex real-time PCR for rapid staphylococcal cassette chromosome mec typing. J Clin Microbiol 2009; 47(11):3692-3706.

Bankevich, A., et al. SPAdes: a new genome assembly algorithm and its applications to single-cell sequencing. J Comput Biol 2012; 19(5):455-477.

Stajich, J. E., et al. The Bioperi toolkit: Perl modules for the life sciences. Genome Res 2002; 12(10):1611-1618.

Kondo, Y., et al. Combination of multiplex PCRs for staphylococcal cassette chromosome mec type assignment: rapid identification system for mec, ccr, and major differences in junkyard regions. Antimicrob Agents Chemother 2007; 51(1):264-274.

Kitchel, B., et al. Genetic factors associated with elevated carbapenem resistance in KPC-producing Klebsiella pneumoniae. Antimicrob Agents Chemother 2010; 54(10):4201-4207.

Howden, B. P., et al. Complete genome sequence of *Staphylococcus aureus* strain JKD6008, an ST239 clone of methicillin-resistant *Staphylococcus aureus* with intermediate-level vancomycin resistance. J Bacteriol 2010; 192(21):5848-5849.

Li, Y., et al. Complete genome sequence of *Staphylococcus aureus* T0131, an ST239-MRSA-SCCmec type III clone isolated in China. J Bacteriol 2011; 193(13):3411-3412.

Holden, M. T., et al. Genome sequence of a recently emerged, highly transmissible, multi-antibiotic-and antiseptic-resistant variant of methicillin-resistant *Staphylococcus aureus*, sequence type 239 (TW). J Bacteriol 2010; 192(3):888-892.

Ito, T., et al. Structural comparison of three types of staphylococcal cassette chromosome mec integrated in the chromosome in methicillin-resistant *Staphylococcus aureus*. Antimicrob Agents Chemother 2001; 45(5):1323-1336.

Suzuki, E., et al. Distribution of mec regulator genes in methicillin-resistant *Staphylococcus* clinical strains. Antimicrob Agents Chemother 1993; 37(6):1219-1226.

Chung, M., et al. Molecular typing of methicillin-resistant *Staphylococcus aureus* by pulsed-field gel electrophoresis: comparison of results obtained in a multilaboratory effort using identical protocols and MRSA strains. Microb Drug Resist 2000; 6(3):189-198.

Crisostomo, M. I., et al. The evolution of methicillin resistance in *Staphylococcus aureus*: similarity of genetic backgrounds in historically early methicillin-susceptible and-resistant isolates and contemporary epidemic clones. Proc Natl Acad Sci U S A 2001; 98(17):9865-9870.

Zhang, K., et al. Novel staphylococcal cassette chromosome mec type, tentatively designated type VIII, harboring class A mec and type 4 ccr gene complexes in a Canadian epidemic strain of methicillin-resistant *Staphylococcus aureus*. Antimicrob Agents Chemother 2009; 53(2):531-540.

Diep, B. A., et al. Complete genome sequence of USA300, an epidemic clone of community-acquired meticillin-resistant *Staphylococcus aureus*. Lancet 2006; 367(9512):731-739.

Gonzalez, B. E., et al. Severe staphylococcal sepsis in adolescents in the era of community-acquired methicillin-resistant *Staphylococcus aureus*. Pediatrics 2005; 115(3):642-648.

Highlander, S. K., et al. Subtle genetic changes enhance virulence of methicillin resistant and sensitive *Staphylococcus aureus*. BMC Microbiol 2007; 7:99.

Tamura, K., et al. MEGA5: molecular evolutionary genetics analysis using maximum likelihood, evolutionary distance, and maximum parsimony methods. Mol Biol Evol 2011; 28(10):2731-2739.

Sambrook, et al. Molecular Cloning. 1989. Second Edition, Cold Spring Harbor laboratory, Plainview, NY; Chapters 9 & 11.

Owczarzy, R., et al. IDT SciTools: a suite for analysis and design of nucleic acid oligomers. Nucl Acids Res 2008; 36 (Web Server Issue):W163-W169.

Letowski, J., et al. Designing better probes: effect of probe size, mismatch position and number of hybridization in DNA oligonucleotide microarrays. J Microbiol Methods 2004; 57(2):269-278.

You, Y., et al. Design of LNA probes that improve mismatch discrimination. Nucl Acids Res 2006; 34(8):e60.

Santalucia Jr., J., et al. The thermodynamics of DNA structural motifs. Annu Rev Biophys Biomol Struct 2004; 33:415-440.

Heissl, A., et al. High-Throughput Genotyping with TaqMan Allelic Discrimination and Allele-Specific Genotyping Assays. Methods Mol Biol 2017; 1492:29-57.

Wu, et al. The ligation amplification reaction (LAR): Amplification of specific DNA sequences using sequential rounds of template-dependent ligation. Genomics 1989; 4(4):560-569.

Barany, F. Genetic disease detection and DNA amplification using cloned thermostable ligase. Proc Natl Acad Sci USA 1991; 88(1):189-193.

Lizardi, P. M., et al. Mutation detection and single-molecule counting using isothermal rolling-circle amplification. Nat Genet 1998; 19(3):225-232.

Baner, J., et al. Signal amplification of padlock probes by rolling circle replication. Nucleic Acid Res 1998; 26(22):5073-5078.

Little, M. C., et al. Strand displacement amplification and homogeneous real-time detection incorporated in a second-generation DNA probe system, BDProbeTecET. Clin Chem 1999; 45(6 Pt 1):777-784.

Oser, A., et al. Nonradioactive Assay of DNA Hybridization by DNA-Template-Mediated Formation of a Ternary TbIII Complex in Pure Liquid Phase. Angew Chem Int Engl 1990; 29(10):1167-1169.

Singh, S. K., et al. LNA (locked nucleic acids): synthesis and high-affinity nucleic acid recognition. Chem Commun 1998; 4:455-456.

Pellestor, F., et al. The peptide nucleic acids (PNAs), powerful tools for molecular genetics and cytogentics. European Journal Human Genetics 2004; 12(9):694-700.

Afonina, I. A., et al. Minor Groove Binder-Conjugated DNA Probes for Quantitative DNA Detection by Hybridization-Triggered Fluorescence. Biotechniques 2002; 32:940-949.

Svanvik, N., et al. Light-up probes. Thiazole orange-conjugated peptide nucleic acid for the detection of target nucleic acid in homogeneous solution. Anal Biochem 2001; 281(1):26-35.

Tygai, S., et al. Molecular beacons: probes that fluoresce upon hybridization. Nat Biotechnol 1996; 14(3):303-308.

Nutiu, R., et al. Tripartite molecular beacons. Nucleic Acids Res 2002; 30(18):e94.

French, D. J., et al. HyBeacon(TM) probes: a new tools for DNA sequence detection and allele discrimination. Mol Cell Probes 2001; 15(6):363-374.

Li, Q., et al. A new class of homogeneous nucleic acid probes based on specific displacement hybridization. Nucleic Acids Res 2002; 30(2):e5.

Cardullo, R. A., et al. Detection of nucleic acid hybridization by nonradiative fluorescence resonance energy transfer. Proc Natl Acad Sci USA 1988; 85(23):8790-8794.

\* cited by examiner

SEQUENCE LISTING

```
<160> NUMBER OF SEQ ID NOS: 85

<210> SEQ ID NO 1
<211> LENGTH: 21
<212> TYPE: DNA
<213> ORGANISM: Artificial Sequence
<220> FEATURE:
<223> OTHER INFORMATION: Primer/Probe

<400> SEQUENCE: 1
cgagtcagct agtggtccgt t                                        21

<210> SEQ ID NO 2
<211> LENGTH: 24
<212> TYPE: DNA
<213> ORGANISM: Artificial Sequence
<220> FEATURE:
<223> OTHER INFORMATION: Primer/Probe

<400> SEQUENCE: 2
atgcatagct cttgctaaag tgta                                     24

<210> SEQ ID NO 3
<211> LENGTH: 19
<212> TYPE: DNA
<213> ORGANISM: Artificial Sequence
<220> FEATURE:
<223> OTHER INFORMATION: Primer/Probe

<400> SEQUENCE: 3
acctatacct gaacgtcaa                                           19

<210> SEQ ID NO 4
<211> LENGTH: 18
<212> TYPE: DNA
<213> ORGANISM: Artificial Sequence
<220> FEATURE:
<223> OTHER INFORMATION: Primer/Probe

<400> SEQUENCE: 4
ctatacctga gcgtcaaa                                            18

<210> SEQ ID NO 5
<211> LENGTH: 24
<212> TYPE: DNA
<213> ORGANISM: Artificial Sequence
<220> FEATURE:
<223> OTHER INFORMATION: Primer/Probe

<400> SEQUENCE: 5
tgcccataac acatttgaca cttt                                     24

<210> SEQ ID NO 6
<211> LENGTH: 20
<212> TYPE: DNA
<213> ORGANISM: Artificial Sequence
<220> FEATURE:
```

```
<223> OTHER INFORMATION: Primer/Probe

<400> SEQUENCE: 6
ttcggccaca gctaaactcg                                                    20

<210> SEQ ID NO 7
<211> LENGTH: 22
<212> TYPE: DNA
<213> ORGANISM: Artificial Sequence
<220> FEATURE:
<223> OTHER INFORMATION: Primer/Probe

<400> SEQUENCE: 7
gttcggctac agctaaactt gc                                                 22

<210> SEQ ID NO 8
<211> LENGTH: 16
<212> TYPE: DNA
<213> ORGANISM: Artificial Sequence
<220> FEATURE:
<223> OTHER INFORMATION: Primer/Probe

<400> SEQUENCE: 8
atcggacccg gtaacc                                                        16

<210> SEQ ID NO 9
<211> LENGTH: 18
<212> TYPE: DNA
<213> ORGANISM: Artificial Sequence
<220> FEATURE:
<223> OTHER INFORMATION: Primer/Probe

<400> SEQUENCE: 9
taatcggacc tggtaacc                                                      18

<210> SEQ ID NO 10
<211> LENGTH: 20
<212> TYPE: DNA
<213> ORGANISM: Artificial Sequence
<220> FEATURE:
<223> OTHER INFORMATION: Primer/Probe

<400> SEQUENCE: 10
cgccaaatga ctcgcattgt                                                    20

<210> SEQ ID NO 11
<211> LENGTH: 22
<212> TYPE: DNA
<213> ORGANISM: Artificial Sequence
<220> FEATURE:
<223> OTHER INFORMATION: Primer/Probe

<400> SEQUENCE: 11
gcatgtgcct ttccgaarta aa                                                 22

<210> SEQ ID NO 12
<211> LENGTH: 18
<212> TYPE: DNA
<213> ORGANISM: Artificial Sequence
<220> FEATURE:
<223> OTHER INFORMATION: Primer/Probe

<400> SEQUENCE: 12
attactgtag cagggctg                                                      18
```

```
<210> SEQ ID NO 13
<211> LENGTH: 15
<212> TYPE: DNA
<213> ORGANISM: Artificial Sequence
<220> FEATURE:
<223> OTHER INFORMATION: Primer/Probe

<400> SEQUENCE: 13
ctgtagcagg gttgc                                                        15

<210> SEQ ID NO 14
<211> LENGTH: 25
<212> TYPE: DNA
<213> ORGANISM: Artificial Sequence
<220> FEATURE:
<223> OTHER INFORMATION: Primer/Probe

<400> SEQUENCE: 14
gatgacgtga taactgtacg tsgat                                             25

<210> SEQ ID NO 15
<211> LENGTH: 22
<212> TYPE: DNA
<213> ORGANISM: Artificial Sequence
<220> FEATURE:
<223> OTHER INFORMATION: Primer/Probe

<400> SEQUENCE: 15
cgcgattgag ggtgaatatt gc                                                22

<210> SEQ ID NO 16
<211> LENGTH: 22
<212> TYPE: DNA
<213> ORGANISM: Artificial Sequence
<220> FEATURE:
<223> OTHER INFORMATION: Primer/Probe

<400> SEQUENCE: 16
aagctaacaa aatcacctac tg                                                22

<210> SEQ ID NO 17
<211> LENGTH: 22
<212> TYPE: DNA
<213> ORGANISM: Artificial Sequence
<220> FEATURE:
<223> OTHER INFORMATION: Primer/Probe

<400> SEQUENCE: 17
caaagctaac aaaattacct ac                                                22

<210> SEQ ID NO 18
<211> LENGTH: 23
<212> TYPE: DNA
<213> ORGANISM: Artificial Sequence
<220> FEATURE:
<223> OTHER INFORMATION: Primer/Probe

<400> SEQUENCE: 18
tgcggatgtc ctatgtctga aag                                               23

<210> SEQ ID NO 19
<211> LENGTH: 17
<212> TYPE: DNA
<213> ORGANISM: Artificial Sequence
<220> FEATURE:
<223> OTHER INFORMATION: Primer/Probe
```

```
<400> SEQUENCE: 19
gcgcaacagg gaagcaa                                              17

<210> SEQ ID NO 20
<211> LENGTH: 20
<212> TYPE: DNA
<213> ORGANISM: Artificial Sequence
<220> FEATURE:
<223> OTHER INFORMATION: Primer/Probe

<400> SEQUENCE: 20
tgcacttaca tatcatccat                                           20

<210> SEQ ID NO 21
<211> LENGTH: 19
<212> TYPE: DNA
<213> ORGANISM: Artificial Sequence
<220> FEATURE:
<223> OTHER INFORMATION: Primer/Probe

<400> SEQUENCE: 21
cacttacata ccatccatc                                            19

<210> SEQ ID NO 22
<211> LENGTH: 24
<212> TYPE: DNA
<213> ORGANISM: Artificial Sequence
<220> FEATURE:
<223> OTHER INFORMATION: Primer/Probe

<400> SEQUENCE: 22
accttatacr gaacatagca gacg                                      24

<210> SEQ ID NO 23
<211> LENGTH: 21
<212> TYPE: DNA
<213> ORGANISM: Artificial Sequence
<220> FEATURE:
<223> OTHER INFORMATION: Primer/Probe

<400> SEQUENCE: 23
tcgatgcgct tctatcactt c                                         21

<210> SEQ ID NO 24
<211> LENGTH: 21
<212> TYPE: DNA
<213> ORGANISM: Artificial Sequence
<220> FEATURE:
<223> OTHER INFORMATION: Primer/Probe

<400> SEQUENCE: 24
tattagatga aggcctcaat a                                         21

<210> SEQ ID NO 25
<211> LENGTH: 23
<212> TYPE: DNA
<213> ORGANISM: Artificial Sequence
<220> FEATURE:
<223> OTHER INFORMATION: Primer/Probe

<400> SEQUENCE: 25
tttattagat gaaggcttca ata                                       23

<210> SEQ ID NO 26
<211> LENGTH: 25
```

```
<212> TYPE: DNA
<213> ORGANISM: Artificial Sequence
<220> FEATURE:
<223> OTHER INFORMATION: Primer/Probe

<400> SEQUENCE: 26
cctgaagaag aagagcgttt aagaa                                             25

<210> SEQ ID NO 27
<211> LENGTH: 21
<212> TYPE: DNA
<213> ORGANISM: Artificial Sequence
<220> FEATURE:
<223> OTHER INFORMATION: Primer/Probe

<400> SEQUENCE: 27
rcatcctacg atggccgaat c                                                 21

<210> SEQ ID NO 28
<211> LENGTH: 22
<212> TYPE: DNA
<213> ORGANISM: Artificial Sequence
<220> FEATURE:
<223> OTHER INFORMATION: Primer/Probe

<400> SEQUENCE: 28
taaacgtcgt aaagtagaac aa                                                22

<210> SEQ ID NO 29
<211> LENGTH: 23
<212> TYPE: DNA
<213> ORGANISM: Artificial Sequence
<220> FEATURE:
<223> OTHER INFORMATION: Primer/Probe

<400> SEQUENCE: 29
acgtaaacgt cgtaaagaag aac                                               23

<210> SEQ ID NO 30
<211> LENGTH: 22
<212> TYPE: DNA
<213> ORGANISM: Artificial Sequence
<220> FEATURE:
<223> OTHER INFORMATION: Primer/Probe

<400> SEQUENCE: 30
catgaccgcc actataacca ga                                                22

<210> SEQ ID NO 31
<211> LENGTH: 22
<212> TYPE: DNA
<213> ORGANISM: Artificial Sequence
<220> FEATURE:
<223> OTHER INFORMATION: Primer/Probe

<400> SEQUENCE: 31
atgcaacatt agcaggagga tg                                                22

<210> SEQ ID NO 32
<211> LENGTH: 17
<212> TYPE: DNA
<213> ORGANISM: Artificial Sequence
<220> FEATURE:
<223> OTHER INFORMATION: Primer/Probe

<400> SEQUENCE: 32
```
tacgactgac ctgatgc                                                    17

<210> SEQ ID NO 33
<211> LENGTH: 16
<212> TYPE: DNA
<213> ORGANISM: Artificial Sequence
<220> FEATURE:
<223> OTHER INFORMATION: Primer/Probe

<400> SEQUENCE: 33
cgactgactt gatgcc                                                     16

<210> SEQ ID NO 34
<211> LENGTH: 35
<212> TYPE: DNA
<213> ORGANISM: Artificial Sequence
<220> FEATURE:
<223> OTHER INFORMATION: Primer/Probe

<400> SEQUENCE: 34
actgcaccta tacctgaacg tcaaaattta tttgg                                35

<210> SEQ ID NO 35
<211> LENGTH: 25
<212> TYPE: DNA
<213> ORGANISM: Artificial Sequence
<220> FEATURE:
<223> OTHER INFORMATION: Primer/Probe

<400> SEQUENCE: 35
acctatacct gaacgtcaaa attta                                           25

<210> SEQ ID NO 36
<211> LENGTH: 35
<212> TYPE: DNA
<213> ORGANISM: Artificial Sequence
<220> FEATURE:
<223> OTHER INFORMATION: Primer/Probe

<400> SEQUENCE: 36
actgcaccta tacctgagcg tcaaaattta tttgg                                35

<210> SEQ ID NO 37
<211> LENGTH: 25
<212> TYPE: DNA
<213> ORGANISM: Artificial Sequence
<220> FEATURE:
<223> OTHER INFORMATION: Primer/Probe

<400> SEQUENCE: 37
acctatacct gagcgtcaaa attta                                           25

<210> SEQ ID NO 38
<211> LENGTH: 35
<212> TYPE: DNA
<213> ORGANISM: Artificial Sequence
<220> FEATURE:
<223> OTHER INFORMATION: Primer/Probe

<400> SEQUENCE: 38
acttttgtaa tcggacccgg taaccgcttt ccaca                                35

<210> SEQ ID NO 39
<211> LENGTH: 25
<212> TYPE: DNA
<213> ORGANISM: Artificial Sequence
<220> FEATURE:
<223> OTHER INFORMATION: Primer/Probe

<400> SEQUENCE: 39
tgtaatcgga cccggtaacc gcttt                                    25

<210> SEQ ID NO 40
<211> LENGTH: 35
<212> TYPE: DNA
<213> ORGANISM: Artificial Sequence
<220> FEATURE:
<223> OTHER INFORMATION: Primer/Probe

<400> SEQUENCE: 40
acttttgtaa tcggacctgg taaccgcttt ccaca                         35

<210> SEQ ID NO 41
<211> LENGTH: 25
<212> TYPE: DNA
<213> ORGANISM: Artificial Sequence
<220> FEATURE:
<223> OTHER INFORMATION: Primer/Probe

<400> SEQUENCE: 41
tgtaatcgga cctggtaacc gcttt                                    25

<210> SEQ ID NO 42
<211> LENGTH: 35
<212> TYPE: DNA
<213> ORGANISM: Artificial Sequence
<220> FEATURE:
<223> OTHER INFORMATION: Primer/Probe

<400> SEQUENCE: 42
aaattactgt agcagggctg catgctggta aacat                         35

<210> SEQ ID NO 43
<211> LENGTH: 25
<212> TYPE: DNA
<213> ORGANISM: Artificial Sequence
<220> FEATURE:
<223> OTHER INFORMATION: Primer/Probe

<400> SEQUENCE: 43
actgtagcag ggctgcatgc tggta                                    25

<210> SEQ ID NO 44
<211> LENGTH: 35
<212> TYPE: DNA
<213> ORGANISM: Artificial Sequence
<220> FEATURE:
<223> OTHER INFORMATION: Primer/Probe

<400> SEQUENCE: 44
aaattactgt agcagggttg catgctggta aacat                         35

<210> SEQ ID NO 45
<211> LENGTH: 25
<212> TYPE: DNA
<213> ORGANISM: Artificial Sequence
<220> FEATURE:
<223> OTHER INFORMATION: Primer/Probe

<400> SEQUENCE: 45
actgtagcag ggttgcatgc tggta                                    25

```
<210> SEQ ID NO 46
<211> LENGTH: 35
<212> TYPE: DNA
<213> ORGANISM: Artificial Sequence
<220> FEATURE:
<223> OTHER INFORMATION: Primer/Probe

<400> SEQUENCE: 46
gatcaaagct aacaaaatca cctactgaaa tacct                               35

<210> SEQ ID NO 47
<211> LENGTH: 25
<212> TYPE: DNA
<213> ORGANISM: Artificial Sequence
<220> FEATURE:
<223> OTHER INFORMATION: Primer/Probe

<400> SEQUENCE: 47
agctaacaaa atcacctact gaaat                                          25

<210> SEQ ID NO 48
<211> LENGTH: 35
<212> TYPE: DNA
<213> ORGANISM: Artificial Sequence
<220> FEATURE:
<223> OTHER INFORMATION: Primer/Probe

<400> SEQUENCE: 48
gatcaaagct aacaaaatta cctactgaaa tacct                               35

<210> SEQ ID NO 49
<211> LENGTH: 25
<212> TYPE: DNA
<213> ORGANISM: Artificial Sequence
<220> FEATURE:
<223> OTHER INFORMATION: Primer/Probe

<400> SEQUENCE: 49
agctaacaaa attacctact gaaat                                          25

<210> SEQ ID NO 50
<211> LENGTH: 35
<212> TYPE: DNA
<213> ORGANISM: Artificial Sequence
<220> FEATURE:
<223> OTHER INFORMATION: Primer/Probe

<400> SEQUENCE: 50
gttaatgcac ttacatatca tccatcctct aacaa                               35

<210> SEQ ID NO 51
<211> LENGTH: 25
<212> TYPE: DNA
<213> ORGANISM: Artificial Sequence
<220> FEATURE:
<223> OTHER INFORMATION: Primer/Probe

<400> SEQUENCE: 51
tgcacttaca tatcatccat cctct                                          25

<210> SEQ ID NO 52
<211> LENGTH: 35
<212> TYPE: DNA
<213> ORGANISM: Artificial Sequence
<220> FEATURE:
<223> OTHER INFORMATION: Primer/Probe
```

<400> SEQUENCE: 52
gttaatgcac ttacatacca tccatcctct aacaa                                35

<210> SEQ ID NO 53
<211> LENGTH: 25
<212> TYPE: DNA
<213> ORGANISM: Artificial Sequence
<220> FEATURE:
<223> OTHER INFORMATION: Primer/Probe

<400> SEQUENCE: 53
tgcacttaca taccatccat cctct                                           25

<210> SEQ ID NO 54
<211> LENGTH: 35
<212> TYPE: DNA
<213> ORGANISM: Artificial Sequence
<220> FEATURE:
<223> OTHER INFORMATION: Primer/Probe

<400> SEQUENCE: 54
atttattaga tgaaggcctc aataaagcga atatc                                35

<210> SEQ ID NO 55
<211> LENGTH: 25
<212> TYPE: DNA
<213> ORGANISM: Artificial Sequence
<220> FEATURE:
<223> OTHER INFORMATION: Primer/Probe

<400> SEQUENCE: 55
ttagatgaag gcctcaataa agcga                                           25

<210> SEQ ID NO 56
<211> LENGTH: 35
<212> TYPE: DNA
<213> ORGANISM: Artificial Sequence
<220> FEATURE:
<223> OTHER INFORMATION: Primer/Probe

<400> SEQUENCE: 56
atttattaga tgaaggcttc aataaagcga atatc                                35

<210> SEQ ID NO 57
<211> LENGTH: 25
<212> TYPE: DNA
<213> ORGANISM: Artificial Sequence
<220> FEATURE:
<223> OTHER INFORMATION: Primer/Probe

<400> SEQUENCE: 57
ttagatgaag gcttcaataa agcga                                           25

<210> SEQ ID NO 58
<211> LENGTH: 35
<212> TYPE: DNA
<213> ORGANISM: Artificial Sequence
<220> FEATURE:
<223> OTHER INFORMATION: Primer/Probe

<400> SEQUENCE: 58
acgtaaacgt cgtaaagtag aacaagatag aaagc                                35

<210> SEQ ID NO 59

```
<211> LENGTH: 25
<212> TYPE: DNA
<213> ORGANISM: Artificial Sequence
<220> FEATURE:
<223> OTHER INFORMATION: Primer/Probe

<400> SEQUENCE: 59
aacgtcgtaa agtagaacaa gatag                                   25

<210> SEQ ID NO 60
<211> LENGTH: 35
<212> TYPE: DNA
<213> ORGANISM: Artificial Sequence
<220> FEATURE:
<223> OTHER INFORMATION: Primer/Probe

<400> SEQUENCE: 60
acgtaaacgt cgtaaagaag aacaagatag aaagc                        35

<210> SEQ ID NO 61
<211> LENGTH: 25
<212> TYPE: DNA
<213> ORGANISM: Artificial Sequence
<220> FEATURE:
<223> OTHER INFORMATION: Primer/Probe

<400> SEQUENCE: 61
aacgtcgtaa agaagaacaa gatag                                   25

<210> SEQ ID NO 62
<211> LENGTH: 35
<212> TYPE: DNA
<213> ORGANISM: Artificial Sequence
<220> FEATURE:
<223> OTHER INFORMATION: Primer/Probe

<400> SEQUENCE: 62
aaccagatac gactgacctg atgcctggat atgat                        35

<210> SEQ ID NO 63
<211> LENGTH: 25
<212> TYPE: DNA
<213> ORGANISM: Artificial Sequence
<220> FEATURE:
<223> OTHER INFORMATION: Primer/Probe

<400> SEQUENCE: 63
gatacgactg acctgatgcc tggat                                   25

<210> SEQ ID NO 64
<211> LENGTH: 35
<212> TYPE: DNA
<213> ORGANISM: Artificial Sequence
<220> FEATURE:
<223> OTHER INFORMATION: Primer/Probe

<400> SEQUENCE: 64
aaccagatac gactgacttg atgcctggat atgat                        35

<210> SEQ ID NO 65
<211> LENGTH: 25
<212> TYPE: DNA
<213> ORGANISM: Artificial Sequence
<220> FEATURE:
<223> OTHER INFORMATION: Primer/Probe

<400> SEQUENCE: 65
```
gatacgactg acttgatgcc tggat                                            25

<210> SEQ ID NO 66
<211> LENGTH: 88
<212> TYPE: DNA
<213> ORGANISM: Artificial Sequence
<220> FEATURE:
<223> OTHER INFORMATION: Amplicon

<400> SEQUENCE: 66
cgagtcagct agtggtccgt ttaatttaac tgcacctata cctgaacgtc aaaatttatt     60
tggctacact ttagcaagag ctatgcat                                         88

<210> SEQ ID NO 67
<211> LENGTH: 79
<212> TYPE: DNA
<213> ORGANISM: Artificial Sequence
<220> FEATURE:
<223> OTHER INFORMATION: Amplicon

<400> SEQUENCE: 67
tgcccataac acatttgaca cttttgtaat cggacccggt aaccgctttc cacatgcagc     60
gagtttagct gtggccgaa                                                   79

<210> SEQ ID NO 68
<211> LENGTH: 241
<212> TYPE: DNA
<213> ORGANISM: Artificial Sequence
<220> FEATURE:
<223> OTHER INFORMATION: Amplicon

<400> SEQUENCE: 68
cgccaaatga ctcgcattgt gaaattactg tagcagggyt gcatgctggt aaacatgtga     60
tgtgtgaaaa accaatggct aaaacgacag cagaagctca aaaaatgata gatacagcta    120
aatcaacagg taaaaaatta acaataggtt atcaaaatcg tttccgagca gatagtcaat    180
ttttacatca agcagcgcaa cgtggcgact taggagacat ttacttcgga aaggcacatg    240
c                                                                    241

<210> SEQ ID NO 69
<211> LENGTH: 240
<212> TYPE: DNA
<213> ORGANISM: Artificial Sequence
<220> FEATURE:
<223> OTHER INFORMATION: Amplicon

<400> SEQUENCE: 69
gatgacgtga taactgtacg tsgatcaaag ctaacaaaat yacctactga aatacctaaa     60
ctctttgtat cttcttctga tgtagttact tcatcaattc ttatttccat atgcttttga    120
tctctaggta tttcatgatt atttctatat acatgaacac ttgtttcatg cagacaaatt    180
gttcctgtat atatttgacc agcatcagtt ttaatttggc aatattcacc ctcaatcgcg    240

<210> SEQ ID NO 70
<211> LENGTH: 118
<212> TYPE: DNA
<213> ORGANISM: Artificial Sequence
<220> FEATURE:
<223> OTHER INFORMATION: Amplicon

<400> SEQUENCE: 70

```
tgcggatgtc ctatgtctga aagtttacga ttattcttat ttctagttaa tgcacttaca    60
taycatccat cctctaacaa ctgttttaca actgcattac cttgcttccc tgttgcgc    118
```

<210> SEQ ID NO 71
<211> LENGTH: 106
<212> TYPE: DNA
<213> ORGANISM: Artificial Sequence
<220> FEATURE:
<223> OTHER INFORMATION: Amplicon

<400> SEQUENCE: 71

```
accttatacg gaacatagca gacgttattt attagatgaa ggcctcaata aagcgaatat    60
ctttgtgaca ggatcaccga tgacagaagt gatagaagcg catcga                  106
```

<210> SEQ ID NO 72
<211> LENGTH: 243
<212> TYPE: DNA
<213> ORGANISM: Artificial Sequence
<220> FEATURE:
<223> OTHER INFORMATION: Amplicon

<400> SEQUENCE: 72

```
cctgaagaag aagagcgttt aagaaacgta acgtcgtaa agwagaacaa gatagaaagc    60
aacgacatga agaacgtaaa cgtcgtaaag wagaacaaga tagaaagctt aaagaaaaat  120
tagaaaagcg aaaagcacaa caataaagcc tgatggcagc atcattcaat gcgtgccacc  180 aggttttat gttttgtcta gaaattaaat aaatcattaa atgattcggc catcgtagga  240 tgy                                                                 243
```

<210> SEQ ID NO 73
<211> LENGTH: 99
<212> TYPE: DNA
<213> ORGANISM: Artificial Sequence
<220> FEATURE:
<223> OTHER INFORMATION: Amplicon

<400> SEQUENCE: 73

```
catgaccgcc actataacca gatacgactg acctgatgcc tggatatgat gtaaatggtt    60
taaccatgca ccagaaacat cctcctgcta atgttgcat                          99
```

<210> SEQ ID NO 74
<211> LENGTH: 88
<212> TYPE: DNA
<213> ORGANISM: Artificial Sequence
<220> FEATURE:
<223> OTHER INFORMATION: Amplicon

<400> SEQUENCE: 74

```
cgagtcagct agtggtccgt ttaatttaac tgcacctata cctgagcgtc aaaatttatt    60
tggctacact ttagcaagag ctatgcat                                      88
```

<210> SEQ ID NO 75
<211> LENGTH: 79
<212> TYPE: DNA
<213> ORGANISM: Artificial Sequence
<220> FEATURE:
<223> OTHER INFORMATION: Amplicon

<400> SEQUENCE: 75

```
tgcccataac acatttgaca cttttgtaat cggacctggt aaccgctttc cacatgcagc    60
gagtttagct gtggccgaa                                                79
```

<210> SEQ ID NO 76
<211> LENGTH: 241
<212> TYPE: DNA
<213> ORGANISM: Artificial Sequence
<220> FEATURE:
<223> OTHER INFORMATION: Amplicon

<400> SEQUENCE: 76

```
cgccaaatga ctcgcattgt gaaattactg tagcagggtt gcatgctggt aaacatgtga      60
tgtgtgaaaa accaatggct aaaacgacag cagaagctca aaaaatgata gatacagcta     120
aatcaacagg taaaaaatta acaataggtt atcaaaatcg tttccgagca gatagtcaat     180
ttttacatca agcagcgcaa cgtggcgact taggagacat ttacttcgga aaggcacatg     240
c                                                                    241
```

<210> SEQ ID NO 77
<211> LENGTH: 240
<212> TYPE: DNA
<213> ORGANISM: Artificial Sequence
<220> FEATURE:
<223> OTHER INFORMATION: Amplicon

<400> SEQUENCE: 77

```
gatgacgtga taactgtacg tsgatcaaag ctaacaaaat tacctactga aatacctaaa      60
ctctttgtat cttcttctga tgtagttact tcatcaattc ttatttccat atgcttttga     120
tctctaggta tttcatgatt atttctatat acatgaacac ttgtttcatg cagacaaatt     180
gttcctgtat atatttgacc agcatcagtt ttaatttggc aatattcacc ctcaatcgcg     240
```

<210> SEQ ID NO 78
<211> LENGTH: 118
<212> TYPE: DNA
<213> ORGANISM: Artificial Sequence
<220> FEATURE:
<223> OTHER INFORMATION: Amplicon

<400> SEQUENCE: 78

```
tgcggatgtc ctatgtctga agtttacga ttattcttat ttctagttaa tgcacttaca       60
taccatccat cctctaacaa ctgttttaca actgcattac cttgcttccc tgttgcgc      118
```

<210> SEQ ID NO 79
<211> LENGTH: 106
<212> TYPE: DNA
<213> ORGANISM: Artificial Sequence
<220> FEATURE:
<223> OTHER INFORMATION: Amplicon

<400> SEQUENCE: 79

```
accttatacg gaacatagca gacgttattt attagatgaa ggcttcaata aagcgaatat      60
ctttgtgaca ggatcaccga tgacagaagt gatagaagcg catcga                   106
```

<210> SEQ ID NO 80
<211> LENGTH: 243
<212> TYPE: DNA
<213> ORGANISM: Artificial Sequence
<220> FEATURE:
<223> OTHER INFORMATION: Amplicon

<400> SEQUENCE: 80

```
cctgaagaag aagagcgttt aagaaacgta aacgtcgtaa agwagaacaa gatagaaagc      60
```

```
aacgacatga agaacgtaaa cgtcgtaaag aagaacaaga tagaaagctt aaagaaaaat      120
tagaaaagcg aaaagcacaa caataaagcc tgatggcagc atcattcaat gcgtgccacc      180
aggtttttat gttttgtcta gaaattaaat aaatcattaa atgattcggc catcgtagga      240 tgy                                                                   243

<210> SEQ ID NO 81
<211> LENGTH: 99
<212> TYPE: DNA
<213> ORGANISM: Artificial Sequence
<220> FEATURE:
<223> OTHER INFORMATION: Amplicon

<400> SEQUENCE: 81
catgaccgcc actataacca gatacgactg acttgatgcc tggatatgat gtaaatggtt       60
taaccatgca ccagaaacat cctcctgcta atgttgcat                              99

<210> SEQ ID NO 82
<211> LENGTH: 241
<212> TYPE: DNA
<213> ORGANISM: Artificial Sequence
<220> FEATURE:
<223> OTHER INFORMATION: Amplicon

<400> SEQUENCE: 82
cgccaaatga ctcgcattgt gaaattactg tagcagggct gcatgctggt aaacatgtga       60
tgtgtgaaaa accaatggct aaaacgacag cagaagctca aaaatgata gatacagcta      120 aatcaacagg taaaaatta acaataggtt atcaaaatcg tttccgagca gatagtcaat      180
ttttacatca agcagcgcaa cgtggcgact taggagacat ttacttcgga aaggcacatg      240
c                                                                     241

<210> SEQ ID NO 83
<211> LENGTH: 240
<212> TYPE: DNA
<213> ORGANISM: Artificial Sequence
<220> FEATURE:
<223> OTHER INFORMATION: Amplicon

<400> SEQUENCE: 83
gatgacgtga taactgtacg tsgatcaaag ctaacaaaat cacctactga aatacctaaa       60
ctctttgtat cttcttctga tgtagttact tcatcaattc ttatttccat atgctttga      120 tctctaggta tttcatgatt atttctatat acatgaacac ttgtttcatg cagacaaatt      180
gttcctgtat atatttgacc agcatcagtt ttaatttggc aatattcacc ctcaatcgcg      240

<210> SEQ ID NO 84
<211> LENGTH: 118
<212> TYPE: DNA
<213> ORGANISM: Artificial Sequence
<220> FEATURE:
<223> OTHER INFORMATION: Amplicon

<400> SEQUENCE: 84
tgcggatgtc ctatgtctga aagtttacga ttattcttat ttctagttaa tgcacttaca       60
tatcatccat cctctaacaa ctgttttaca actgcattac cttgcttccc tgttgcgc       118

<210> SEQ ID NO 85
<211> LENGTH: 243
<212> TYPE: DNA
<213> ORGANISM: Artificial Sequence
```

-continued

```
<220> FEATURE:
<223> OTHER INFORMATION: Amplicon

<400> SEQUENCE: 85
cctgaagaag aagagcgttt aagaaacgta aacgtcgtaa agwagaacaa gatagaaagc      60
aacgacatga agaacgtaaa cgtcgtaaag tagaacaaga tagaaagctt aaagaaaaat     120
tagaaaagcg aaaagcacaa caataaagcc tgatggcagc atcattcaat gcgtgccacc    180
aggtttttat gttttgtcta gaaattaaat aaatcattaa atgattcggc catcgtagga    240 tgy                                                                   243
```

METHODS AND ASSAYS FOR SUBTYPING *STAPHYLOCOCCUS AUREUS* CLONAL COMPLEX 8 STRAINS

CROSS-REFERENCE TO RELATED APPLICATIONS

This application is the U.S. National Stage of International Application No. PCT/US2018/029666, filed on Apr. 26, 2018, which claims the benefit of U.S. Provisional Patent Application No. 62/490,460, filed on Apr. 26, 2017, the contents of each of which are incorporated herein by reference in their entireties.

STATEMENT REGARDING FEDERALLY SPONSORED RESEARCH

This invention was made with governmental support under contract number 200-2014-61029 awarded by the Centers for Disease Control and Prevention (CDC). The United States government has certain rights in the invention.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 20,397 byte ASCII (text) file named "Seq_List" created on Apr. 26, 2018.

TECHNICAL FIELD

This application relates to assays, probes, primers, methods, microarrays, and kits for detecting the presence of *Staphylococcus aureus* in a sample.

BACKGROUND

*Staphylococcus aureus* causes infection in both immunocompromised and healthy persons, and in both healthcare and community settings. In the United States, most of the community-associated methicillin-resistant *S. aureus* (CA-MRSA) infections and a significant proportion of healthcare-associated (HA-) infections are caused by strains in clonal complex 8 (CC8) (1-3). Lineages within CC8 include the major so-called epidemic "clones" USA300, USA500, Archaic, Iberian, and the lineage identified by multilocus sequence typing as sequence type (ST) 239 (4). ST239 is an HA lineage with distinct populations distributed throughout Asia, in Eastern Europe, South America, and Australia (1, 5, 6). ST239, a hybrid of strains ST8 and ST30 (7), is often classed in CC30, given its distant relationship to the rest of CC8 and its spa gene type similarity to ST30 isolates. The Archaic (ST250) and Iberian (ST247) strains are also HA; the Archaic clone was widespread in parts of Europe decades ago, however, it has largely disappeared with the appearance of other more antimicrobial resistant CC8 lineages such as USA500 (8). The CA-MRSA strain USA300 emerged clinically only around 2000, and has since become the most prevalent pathogenic strain circulating in the U.S. (2, 3).

Distinguishing among the sub-lineages of CC8 is critical for purposes of epidemiology and surveillance, especially as the epidemiologic separation between HA and CA strains disappears (1). Although strain typing techniques have improved over time, they still have many limitations. Pulse field gel electrophoresis (PFGE), the method by which the "USA" strains were originally defined (9), is laborious and determination of a strain type can be subjective. Heterogeneity in banding patterns and discordance with other typing methods is not uncommon (10). Sequencing and interpretation of the spa gene is relatively expensive, and spa types aren't always consistent with evolutionary lineages (5, 10-13). Furthermore, PFGE and spa typing alone are often not able to distinguish among lineages within CC8, as well as other clonal complexes (14). Currently, many laboratories use PCR typing that targets factors located on mobile genetic elements, e.g., Panton-Valentine leukocidin (PVL) genes, arginine catabolic mobile element (ACME) genes, enterotoxin genes, and the SCCmec variants.

Confounding the issue is the multitude of names given to a strain type (15) as well as the confusion regarding the phylogenetic relatedness among strains in CC8. Relatively imprecise methods of strain characterization and lack of consistency with regard to reference isolates have caused variation in the classification of the CC8 lineages. Most strains were originally defined and deposited in repositories prior to the routine use of whole genome sequencing (WGS) and WGS-based phylogenies, and relatedness to these type strains was inferred based on varying criteria, resulting in inconsistent application of strain nomenclature. An influential study by Li et al. (4) on the evolution of virulence in CC8 illustrated that USA300 is a lineage derived from USA500. In that study, the authors identified a now widely used set of genetic markers to distinguish between USA500 and Iberian strains, using a USA500 reference isolate called BD02-25. Two recent studies refuted the idea that USA500 is the progenitor to USA300 using different USA500 isolate genomes as references; Jamrozy et al. (16) used 2395 originally described in a study on hypervirulence in a USA500 isolate (typing method unknown) (17), and Boyle-Vavra et al. (18) used NRS385 (aka 95938), the USA500 type strain described by McDougal in 2003 (9) (deposited at BEI Resources as USA500, cat. no. NR-46071). We postulate that not all of these isolates belong to the same phylogenetic clade, though they were previously described as the same strain, USA500.

One goal of the inventors was to closely examine the cladistics of CC8 with whole genome sequence (WGS) data, illustrating the issues that have arisen from lack of consistency in type nomenclature, with the hopes of more clearly defining CC8 sub-lineages. Another goal was to develop a rapid and simple, yet robust strain-typing scheme based on stable genomic markers, e.g., real-time PCR assays targeting canonical single nucleotide polymorphisms (canSNPs), or SNPs that define a lineage (14, 19).

*Staphylococcus aureus* is a major human pathogen worldwide in both community and healthcare settings. Surveillance for *S. aureus* strains is important to our understanding of their spread and to informing infection prevention and control. Confusion surrounding the strain nomenclature of one of the most prevalent lineages of *S. aureus*, clonal complex 8 (CC8), as well as the imprecision of current tools for typing methicillin-resistant *S. aureus* (MRSA) and the lack of tools for typing methicillin-susceptible *S. aureus* (MSSA) make surveillance and source tracing difficult and sometimes misleading. There is a need for assays, methods, and kits that address these challenges in detecting and typing MRSA and MSSA.

SUMMARY

The present invention provides useful probes and methods for detecting canSNPs from a CC8 phylogeny to target each of the major lineages, including the widely circulating USA300 subtype USA300-0114, an oft-cited etiologic cause for MRSA clusters. The present invention involves a canSNP-based approach to eliminate the lineage confusion seen with PFGE, spa typing, and mobile genetic marker typing, as SNPs are inherently stable and quantify relatedness among strains. Additionally, the methods and assays provided herein may employ real-time PCR as a rapid, scalable technique that is ubiquitous in public health and reference laboratories, making the assay scheme an attractive tool for surveillance and epidemiology.

In certain aspects, the present invention provides a method of detecting a *Staphylococcus aureus* clonal complex 8 (CC8) strain in a biological sample. The method typically comprises the steps of: obtaining nucleic acid from a biological sample; optionally amplifying the nucleic acid to produce an amplicon; contacting the nucleic acid or the amplicon with a SNP variant polynucleotide probe; and detecting specific hybridization of the SNP variant probe to the nucleic acid or to the amplicon, thereby detecting Clade CC8, Clade Inner CC8, Clade CC8a, Clade CC8b, Clade CC8c, Clade CC8e, Clade CC8f, or Clade ST239. One or more probes are preferably used, e.g., 2, 3, 4, 6, or more. The SNP variant polynucleotide probe preferably selected from the group consisting of: 20-35 contiguous nucleotides of SEQ ID NOs.: 34, 38, 42, 46, 50, 54, 58, or 62, a sequence which is at least 85% identical thereto, an RNA equivalent, or a reverse complement thereof; and 13-25 contiguous nucleotides of SEQ ID NOs.: 35, 39, 43, 47, 51, 55, 59, or 63, a sequence which is at least 85% identical thereto, an RNA equivalent, or a reverse complement thereof.

In another exemplary embodiment the method of detecting a *Staphylococcus aureus* CC8 strain in a biological sample, comprises the steps of: obtaining nucleic acid from a biological sample; optionally amplifying the nucleic acid to produce an amplicon; producing a sequence from the nucleic acid or the amplicon; and detecting the presence of SEQ ID NO: 3, 34, 35, 8, 38, 39, 12, 42, 43, 16, 46, 47, 20, 50, 51, 24, 54, 55, 28, 58, 59, or 32, 62, or 63, or the reverse complement thereof, in the sequence, thereby identifying the presence of Clade CC8, Clade Inner CC8, Clade CC8a, Clade CC8b, Clade CC8c, Clade CC8e, Clade CC8f, or Clade ST239. In a particular embodiment, the presence of SEQ ID NO: 3, 34, 8, 38, 12, 42, 16, 46, 20, 50, 24, 54, 28, 58, 32, 62, or the reverse complement thereof is detected in the sequence.

The present invention is also directed to one or more polynucleotide probes.

Preferred probes of the invention are selected from the group consisting of:
a) 20-35 contiguous nucleotides of SEQ ID NOs.: 34, 38, 42, 46, 50, 54, 58, or 62, a sequence which is at least 85% identical thereto, an RNA equivalent, or a reverse complement thereof; and
b) 13-25 contiguous nucleotides of SEQ ID NOs.: 35, 39, 43, 47, 51, 55, 59, or 63, a sequence which is at least 85% identical thereto, an RNA equivalent, or a reverse complement thereof.

In certain embodiments the polynucleotide probe comprises a label or is otherwise detectable.

In a particular embodiment, the method of detecting *Staphylococcus aureus* in a subject, comprises the steps of: contacting a nucleic acid sample obtained from the subject with at least one detectably labeled probe comprising a nucleic acid sequence selected from the group consisting of: at least 20 contiguous nucleotides of SEQ ID NOs.: 3-4, 8-9, 12-13, 16-17, 20-21, 24-25, 28-29, and 32-33; optionally at least one forward primer comprising a nucleic acid sequence selected from the group consisting of SEQ ID NO: 1, 5, 10, 14, 18, 22, 26, and 30; and optionally at least one reverse primer comprising a nucleic acid sequence of SEQ ID NO: 2, 6, 7, 11, 15, 19, 23, 27, and 31. Preferably the probes used in these methods are labeled or otherwise easily detectible and in a exemplary embodiment, real-time PCR is used. Upon detecting the detectably labeled probe, the presence of *Staphylococcus aureus* in the subject sample is confirmed. In one aspect, the at least one forward primer comprises SEQ ID NO: 1, the at least one reverse primer comprises SEQ ID NO: 2, the at least one detectably labeled probe comprises SEQ ID NO: 3 and/or 4, and *Staphylococcus aureus* Clade CC8 including ST239 and ST630 is detected.

In other embodiments, the at least one forward primer comprises SEQ ID NO: 5, the at least one reverse primer comprises SEQ ID NO: 6 and/or 7, the at least one detectably labeled probe comprises SEQ ID NO: 8 and/or 9, and *Staphylococcus aureus* Clade Inner CC8 excluding ST239 and ST630 is detected.

In yet other embodiments, the at least one forward primer comprises SEQ ID NO: 10, the at least one reverse primer comprises SEQ ID NO: 11, the at least one detectably labeled probe comprises SEQ ID NO: 12 and/or 13, and *Staphylococcus aureus* Clade CC8a including Archaic and Iberian is detected.

In one embodiment, the at least one forward primer comprises SEQ ID NO: 14, the at least one reverse primer comprises SEQ ID NO: 15, the at least one detectably labeled probe comprises SEQ ID NO: 16 and/or 17, and *Staphylococcus aureus* Clade CC8b is detected.

In another embodiment, the at least one forward primer comprises SEQ ID NO: 18, the at least one reverse primer comprises SEQ ID NO: 19, the at least one detectably labeled probe comprises SEQ ID NO: 20 and/or 21, and *Staphylococcus aureus* Clade CC8c including New Iberian is detected.

In some aspects, the at least one forward primer comprises SEQ ID NO: 22, the at least one reverse primer comprises SEQ ID NO: 23, the at least one detectably labeled probe comprises SEQ ID NO: 24 and/or 25, and *Staphylococcus aureus* Clade CC8e including USA500 and USA300 is detected.

In other aspects, the at least one forward primer comprises SEQ ID NO: 26, the at least one reverse primer comprises SEQ ID NO: 27, the at least one detectably labeled probe comprises SEQ ID NO: 28 and/or 29, and *Staphylococcus aureus* Clade CC8f including USA300 is detected.

In yet other aspects, the at least one forward primer comprises SEQ ID NO: 30 the at least one reverse primer comprises SEQ ID NO: 31, the at least one detectably labeled probe comprises SEQ ID NO: 32 and/or 33, and *Staphylococcus aureus* Clade ST239 is detected.

In certain embodiments, the at least one forward primer, the at least one reverse primer, and/or the at least one detectably labeled probe detect a canonical single nucleotide polymorphism (SNP) specific to a *Staphylococcus aureus* Clade.

In other aspect, the present invention is directed to a method of detecting *Staphylococcus aureus* in a subject, comprising: amplifying a nucleic acid segment from a sample obtained from the subject with at least one forward primer comprising a nucleic acid sequence selected from the group consisting of SEQ ID NO: 1, 5, 10, 14, 18, 22, 26, and 30; and at least one reverse primer comprising a nucleic acid sequence of SEQ ID NO: 2, 6, 7, 11, 15, 19, 23, 27, and 31 to produce an amplicon; and sequencing the amplicon to detect the *Staphylococcus aureus*. In one aspect, the amplicon is sequenced with next-generation sequencing.

In another embodiment, the method further comprises performing whole genome sequencing (WGS) of DNA in the sample to confirm detection of the *Staphylococcus aureus*.

In yet further specific embodiments the method, the sample is obtained from environment or food; alternatively an animal, e.g., a human subject. Still further specific embodiments further include after detecting the presence of a CC8 strain, a step of administering an effective amount of Doxycycline, Linezolid, Rifampin, Trimethoprim-Sulfamethoxazole, Vancomycin, or a combination thereof.

In some aspects, the sample is a wound swab, a nasal swab, rectal swab, skin swab, saliva, feces, urine, whole blood, serum, plasma, or buffy coat.

In yet other aspects, the present invention provides a kit comprising: at least one detectably labeled probe comprising a nucleic acid sequence selected from the group consisting of SEQ ID NOs.: 3-4, 8-9, 12-13, 16-17, 20-21, 24-25, 28-29, and 32-33; at least one forward primer comprising a nucleic acid sequence selected from the group consisting of SEQ ID NO: 1, 5, 10, 14, 18, 22, 26, and 30; and at least one reverse primer comprising a nucleic acid sequence of SEQ ID NO: 2, 6, 7, 11, 15, 19, 23, 27, and 31; and optionally one or more PCR reagents.

In one aspect, the at least one detectably labeled probe, the at least one forward primer, the at least one reverse primer, and the one or more PCR reagents are lyophilized.

In another aspect, the present invention is directed to a microarray for detecting a *Staphylococcus aureus* CC8 strain in a biological sample comprising a surface and at least one probe comprising a nucleic acid sequence selected from the group consisting of: at least 20 contiguous nucleotides of SEQ ID NOs.: 3-4, 8-9, 12-13, 16-17, 20-21, 24-25, 28-29, 32-33; 20-35 contiguous nucleotides of SEQ ID NOs.: 34, 38, 42, 46, 50, 54, 58, or 62; 13-25 contiguous nucleotides of SEQ ID NOs.: 35, 39, 43, 47, 51, 55, 59, or 63; and a sequence which is at least 85% identical, an RNA equivalent, or a reverse complement of the SEQ ID NOs. above, wherein the at least one probe is immobilized on the surface of the microarray. In a particular embodiment, the surface of the microarray is glass.

The invention is also directed to a kit for detecting a *Staphylococcus aureus* CC8 strain in a biological sample. In one embodiment, the kit comprises: a polynucleotide probe selected from the group consisting of: at least 20 contiguous nucleotides of SEQ ID NOs.: 3-4, 8-9, 12-13, 16-17, 20-21, 24-25, 28-29, 32-33; 20-35 contiguous nucleotides of SEQ ID NOs.: 34, 38, 42, 46, 50, 54, 58, or 62; 13-25 contiguous nucleotides of SEQ ID NOs.: 35, 39, 43, 47, 51, 55, 59, or 63; and a sequence which is at least 85% identical, an RNA equivalent, or a reverse complement of the SEQ ID NOs. above. Preferably the probe is labeled. In an exemplary embodiment the kit also comprises a SNP variant forward primer; and a SNP variant reverse primer. The preferred SNP variant primers are selected from the sequences herein.

DETAILED DESCRIPTION

Figure 1:
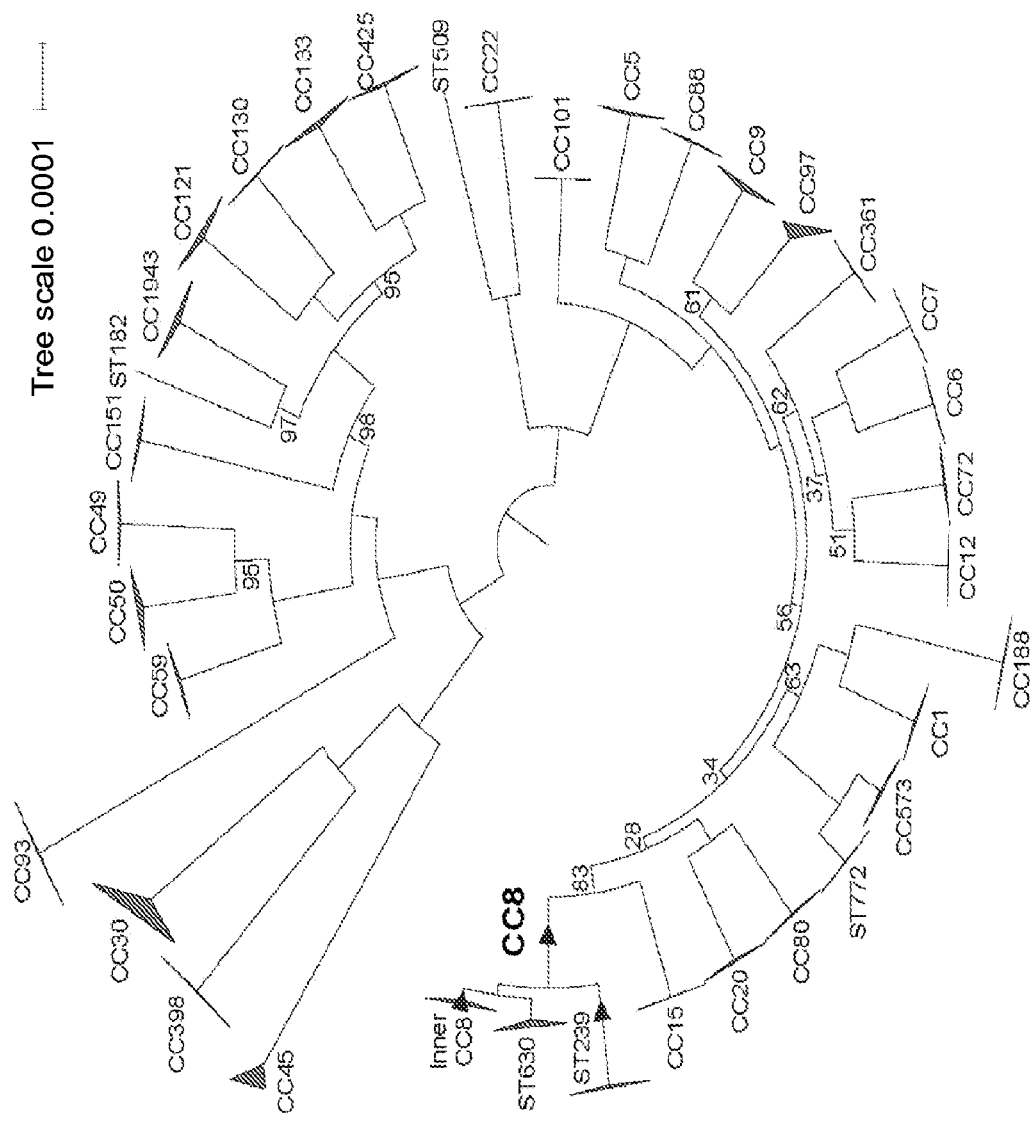
FIG. 1 depicts WGS-based maximum likelihood phylogeny (using the best-fit model TVMe+ASC) of 497 *S. aureus* isolate genomes showing the CC8 group in the context of the whole of *S. aureus*. This analysis includes 1000 bootstraps of 275,242 total SNPs in a core genome size (the length of the reference genome covered by all samples, excluding repeated regions) of 1.84 Mbp. Regions of chromosomal exchange among lineages resulting in hybrid strains (e.g., ST239) were not excluded. Bootstrap values are 100% except where indicated. Branches of the phylogeny on which SNPs were selected for assay development are marked with a triangle.

Herein, we disclose a typing scheme for designating CC8 strains based on novel and stable genomic markers. The disclosed method is rapid and easy to use. We demonstrate its superiority over traditional typing techniques. This scheme has the potential to greatly improve epidemiological investigations of *S. aureus* as well as clinical diagnosis of *S. aureus*.

As used herein, the verb "comprise" as is used in this description and in the claims and its conjugations are used in its non-limiting sense to mean that items following the word are included, but items not specifically mentioned are not excluded.

As used herein, reference to an element by the indefinite article "a" or "an" does not exclude the possibility that more than one of the elements are present, unless the context clearly requires that there is one and only one of the elements. The indefinite article "a" or "an" thus usually means "at least one."

As used herein, "hybridization" refers to the ability of complementary single-stranded DNA or RNA to form a duplex molecule (also referred to as a hybridization complex). Nucleic acid hybridization techniques can be used to form hybridization complexes between a primer and a nucleic acid (e.g., a *S. aureus* nucleic acid), a primer and an amplicon, a probe and a nucleic acid, or a probe and an amplicon.

"Specific hybridization," "specifically hybridizable," and "specifically hybridizes" are terms which indicate a sufficient degree of complementarity such that stable and specific binding occurs between an oligonucleotide and its DNA or RNA target.

Hybridization conditions resulting in particular degrees of stringency will vary depending upon the nature of the hybridization method and the composition and length of the hybridizing nucleic acid sequences. Generally, the temperature of hybridization and the ionic strength (such as the $Na_+$ concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11). The following is an exemplary set of hybridization conditions and is not limiting:

Very High Stringency (detects sequences that share at least 90% identity):
Hybridization: 5×SSC at 65° C. for 16 hours; Wash twice: 2×SSC at room temperature (RT) for 15 minutes each; Wash twice: 0.5×SSC at 65° C. for 20 minutes each.
High Stringency (detects sequences that share at least 80% identity):
Hybridization: 5×-6×SSC at 65° C.-70° C. for 16-20 hours; Wash twice: 2×SSC at RT for 5-20 minutes each; Wash twice: 1×SSC at 55° C.-70° C. for 30 minutes each.
Low Stringency (detects sequences that share at least 50% identity):
Hybridization: 6×SSC at RT to 55° C. for 16-20 hours; Wash at least twice: 2×-3×SSC at RT to 55° C. for 20-30 minutes each.

In some embodiments, the probe or primer disclosed herein specifically hybridizes to the nucleic acids or amplicon under very high stringency. In other embodiments, the probe or primer disclosed herein specifically hybridizes to the nucleic acids or amplicon under high stringency. In yet other embodiments, the probe or primer disclosed herein specifically hybridizes to the nucleic acids or amplicon under low stringency.

As used herein in connection with probes, the term "polynucleotide" or "oligonucleotide" denotes a DNA or RNA molecule of at least 10 nucleotides. For example, at least 11, 12, 13, 14, 15, 16, 17, 18, 19, 20, 21, 22, 23, 24, 25, 30 or 35 nucleotides. In some embodiments, the length of the polynucleotide is up to 45 nucleotides. For example, up to 20, 25, 30, 35, or 40 nucleotides. In other embodiments, the polynucleotide has a length of 10-45 nucleotides or any number range in between, e.g., 10-45, 12-45, 12-41, 14-41, 14-37, 16-37, 16-33, 18-33, 18-29, 20-29, or 20-25 nucleotides. In further embodiments, the polynucleotide has a length of 10-35 nucleotides or any number range in between, e.g., 10-35, 12-35, 12-33, 14-33, 14-31, 16-31, 16-29, 18-29, 18-27, 20-27, or 20-25 nucleotides.

It is known in the art that SNP mismatches can affect the hybridization of probes by reducing the Tm of a polynucleotide by as much as 5-18° C. The degree of effect on Tm depends on the mismatch position, type of mismatch (e.g., A/A, A/C, G/T), as well as the surrounding environment, sequence, or both (Owczarzy R, Tataurov A V, et al. (2008) IDT SciTools: a suite for analysis and design of nucleic acid oligomers. Nucl Acids Res, 36 (suppl 2): W163-69). The destabilizing effects are highest for mismatches located in the interior of the duplex (Letowski J, Brousseau R, Masson L. (2004). Designing better probes: effect of probe size, mismatch position and number on hybridization in DNA oligonucleotide microarrays. J Microbiol Meth, 57:269-278; You Y, Moreira B G, et al. (2006) Design of LNA probes that improve mismatch discrimination. Nucl Acids Res, 34:e60; SantaLucia J Jr, Hick D. (2004) The thermodynamics of DNA structural motifs. Annu Rev Biophys Biomol Struct, 33:415-40; and Heissl A, Arbeithuber B, Tiemann-Boege I., High-Throughput Genotyping with TaqMan Allelic Discrimination and Allele-Specific Genotyping Assays, Methods Mol Biol. 2017; 1492:29-57).

In some embodiments, the probe is designed to have a Tm that is an approximately 0-20° C. above the annealing temperature of the amplification primers to promote hybridization. For example, 0-20, 0-18, 1-18, 1-16, 2-16, 2-14, 3-14, 3-12, 4-12, 4-10, 5-10, 5-8, or 6-8° C.

To detect the presence of CC8 Clade, in some embodiments, a polynucleotide identical to SEQ ID NO: 3, 34, or 35 is used. In other embodiments, an RNA equivalent, or a reverse complement of SEQ ID NO: 3, 34, or 35 is used.

To detect the absence of CC8 Clade, in some embodiments, a polynucleotide identical to SEQ ID NO: 4, 36, or 37 is used. In other embodiments, an RNA equivalent, or a reverse complement of SEQ ID NO: 4, 36, or 37 is used.

To detect the presence of inner CC8 Clade, in some embodiments, a polynucleotide identical to SEQ ID NO: 8, 38, or 39 is used. In other embodiments, an RNA equivalent, or a reverse complement of SEQ ID NO: 8, 38, or 39 is used.

To detect the absence of inner CC8 Clade, in some embodiments, a polynucleotide identical to SEQ ID NO: 9, 40, or 41 is used. In other embodiments, an RNA equivalent, or a reverse complement of SEQ ID NO: 9, 40, or 41 is used.

To detect the presence of Clade CC8a, in some embodiments, a polynucleotide identical to SEQ ID NO: 12, 42, or 43 is used. In other embodiments, an RNA equivalent, or a reverse complement of SEQ ID NO: 12, 42, or 43 is used.

To detect the absence of Clade CC8a, in some embodiments, a polynucleotide identical to SEQ ID NO: 13, 44, or 45 is used. In other embodiments, an RNA equivalent, or a reverse complement of SEQ ID NO: 13, 44, or 45 is used.

To detect the presence of Clade CC8b, in some embodiments, a polynucleotide identical to SEQ ID NO: 16, 46, or 47 is used. In other embodiments, an RNA equivalent, or a reverse complement of SEQ ID NO: 16, 46, or 47 is used.

To detect the absence of Clade CC8b, in some embodiments, a polynucleotide identical to SEQ ID NO: 17, 48, or 49 is used. In other embodiments, an RNA equivalent, or a reverse complement of SEQ ID NO: 17, 48, or 49 is used.

To detect the presence of Clade CC8c, in some embodiments, a polynucleotide identical to SEQ ID NO: 20, 50, or 51 is used. In other embodiments, an RNA equivalent, or a reverse complement of SEQ ID NO: 20, 50, or 51 is used.

To detect the absence of Clade CC8c, in some embodiments, a polynucleotide identical to SEQ ID NO: 21, 52, or 53 is used. In other embodiments, an RNA equivalent, or a reverse complement of SEQ ID NO: 21, 52, or 53 is used.

To detect the presence of Clade CC8e, in some embodiments, a polynucleotide identical to SEQ ID NO: 24, 54, or 55 is used. In other embodiments, an RNA equivalent, or a reverse complement of SEQ ID NO: 24, 54, or 55 is used.

To detect the absence of Clade CC8e, in some embodiments, a polynucleotide identical to SEQ ID NO: 25, 56, or 57 is used. In other embodiments, an RNA equivalent, or a reverse complement of SEQ ID NO: 25, 56, or 57 is used.

To detect the presence of Clade CC8f, in some embodiments, a polynucleotide identical to SEQ ID NO: 28, 58, or 59 is used. In other embodiments, an RNA equivalent, or a reverse complement of SEQ ID NO: 28, 58, or 59 is used.

To detect the absence of Clade CC8f, in some embodiments, a polynucleotide identical to SEQ ID NO: 29, 60, or 61 is used. In other embodiments, an RNA equivalent, or a reverse complement of SEQ ID NO: 29, 60, or 61 is used.

To detect the presence of ST239, in some embodiments, a polynucleotide identical to SEQ ID NO: 32, 62, or 63 is used. In other embodiments, an RNA equivalent, or a reverse complement of SEQ ID NO: 32, 62, or 63 is used.

To detect the absence of ST239, in some embodiments, a polynucleotide identical to SEQ ID NO: 33, 64, or 65 is used. In other embodiments, an RNA equivalent, or a reverse complement of SEQ ID NO: 33, 64, or 65 is used.

A polynucleotide probe needs not be 100% complementary to its target DNA or RNA sequence to be specifically hybridizable. A polynucleotide is specifically hybridizable when there is a sufficient degree of complementarity to avoid non-specific binding of the polynucleotide to non-target sequences under conditions in which specific binding is desired, or under conditions in which an assay is performed.

The disclosure also contemplates the use of probes which comprise a polynucleotide sequence that is essentially identical to one of SEQ ID. NOs.: 3, 4, 8, 9, 12, 13, 16, 17, 29, 21, 24, 25, 28, 29, 32, 33, 34, 36, 38, 40, 42, 44, 46, 48, 50, 52, 54, 56, 58, 60, 62, 64, 35, 37, 39, 41, 43, 45, 47, 49, 51, 53, 55, 57, 59, 61, 63, or 65.

In some embodiments, the difference comprises a substitution. In other embodiments, the difference comprises an insertion. In yet other embodiments, the difference comprises a deletion. In further embodiments, the difference comprises a combination of a substitution, an insertion, and/or a deletion. Such sequence variations are acceptable as long as they do not affect the reliability of the polynucleotide probes in specific binding to the variant or reference sequences.

In some embodiments, the polynucleotide sequence is essentially identical to one of SEQ ID NOs.: 3, 4, 8, 9, 12, 13, 16, 17, 29, 21, 24, 25, 28, 29, 32, or 33, but differs by one or more (e.g., 1, 2, or 3) nucleotides. In these embodiments, the polynucleotide sequence has at least 80% sequence identity to one of SEQ ID NOs.: 3, 4, 8, 9, 12, 13, 16, 17, 29, 21, 24, 25, 28, 29, 32, or 33. For example, at least 81, 82, 83, 84, 85, 86, 87, 88, 89, 90, 91, 92, 93, 94, or 95% sequence identity. In other embodiments, the polynucleotide sequence is an RNA equivalent of the polynucleotide described in this paragraph. In yet other non-limiting embodiments, the polynucleotide is a reverse complement of the polynucleotide described in this paragraph.

In other embodiments, the polynucleotide sequence is essentially identical to one of SEQ ID NOs.: 34, 36, 38, 40, 42, 44, 46, 48, 50, 52, 54, 56, 58, 60, 62, or 64, but differs by one or more nucleotides. For example, the difference may be 1, 2, 3, 4, 5, 6, 7, 8, 9, 10, 11, 12, 13, 14, 15, 16, 17, 18, 19, or 20 nucleotides. In these embodiments, the polynucleotide sequence has at least 42% sequence identity to one of SEQ ID NOs.: 34, 36, 38, 40, 42, 44, 46, 48, 50, 52, 54, 56, 58, 60, 62, or 64. For example, at least 45, 50, 55, 60, 65, 70, 75, 80, 85, 90, or 95% sequence identity. In yet other embodiments, the polynucleotide sequence is an RNA equivalent of the polynucleotide described in this paragraph. In further non-limiting embodiments, the polynucleotide is a reverse complement of the polynucleotide described in this paragraph.

The disclosure further contemplates the use of probes which comprise a polynucleotide sequence that differs from SEQ ID NOs.: 35, 37, 39, 41, 43, 45, 47, 49, 51, 53, 55, 57, 59, 61, 63, or 65 by one or more nucleotides. For example, the difference may be 1, 2, 3, 4, 5, 6, 7, 8, 9, or 10 nucleotides. In these embodiments, the polynucleotide sequence has at least 60% sequence identity to one of SEQ ID NOs.: 34, 36, 38, 40, 42, 44, 46, 48, 50, 52, 54, 56, 58, 60, 62, or 64. For example, at least 65, 70, 75, 80, 85, 90, or 95% sequence identity. In yet other embodiments, the polynucleotide sequence is an RNA equivalent of the polynucleotide described in this paragraph. In further non-limiting embodiments, the polynucleotide is a reverse complement of the polynucleotide described in this paragraph.

A probe comprises an isolated nucleic acid attached to a detectable label or reporter molecule. As used herein, the term "label" refers to a detectable compound or composition that is conjugated directly or indirectly to another molecule to facilitate detection of that molecule. Typical labels include radioactive isotopes, ligands, chemiluminescent agents, and enzymes. Methods for labeling and guidance in the choice of labels appropriate for various purposes are discussed, e.g., in Sambrook et al. (1989), Ausubel et al. (1987), and Ausubel et al. (1995).

Specific, non-limiting examples of labels include fluorescent tags, enzymatic linkages, and radioactive isotopes. Non-limiting examples of labels include: amine-reactive dye, hapten, biotin, fluorescent dyes such as Methoxycoumarin, Dansyl, Pyrene, AMCA, Marina Blue dye, Dapoxyl dye, Dialkylaminocoumarin, Bimane, Hydroxycoumarin, Cascade Blue dye, Pacific Orange dye, Cascade Yellow dye, Pacific Blue dye, PyMPO, NBD, QSY 35, Fluorescein, Oregon Green 488, tetramethylrhodamine, Texas Red, Cy5, Rhodamine dyes (such as Rhodamine Green dye, Rhodamine 6G, Tetramethyl-rhodamine (TMR), Lissamine rhodamine B, Rhodamine Red dye, X-rhodamine), 2',7'-Dichloro-fluorescein, Oregon Green 514, Eosin, Naphthofluorescein, Malachite green, Alexa Fluor dyes (such as Alexa Fluor 350, Alexa Fluor 405, Alexa Fluor 430, Alexa Fluor 488, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 635, Alexa Fluor 647, Alexa Fluor 660, Alexa Fluor 680, Alexa Fluor 700, Alexa Fluor 750, and Alexa Fluor 790), SYBR 101, FAM, 4',5'-Dichloro-2',7'-dimethoxy-fluorescein (JOE), TAMRA, ROX, BODIPY (such as BODIPY FL, BODIPY R6G, BODIPY 530/550, BODIPY 564/570, BODIPY FL, BODIPY R6G, BODIPY 564/570 and BODIPY 581/591, BODIPY 558/568, BODIPY 564/570, BODIPY 576/589, BODIPY 581/591, BODIPY 630/650, BODIPY 650/665, BODIPY TR, BODIPY TMR dyes), QSY 7, QSY 9, and QSY 21.

In a non-limiting aspect, the polynucleotide probe comprises a TAQMAN® probe.

Some embodiments of the disclosure comprises contacting the nucleic acids with a probe and detecting the hybridization of the probe. Some embodiments of the disclosure further comprises amplifying the nucleic acid to produce an amplicon and contacting the amplicon with the probe and detecting the hybridization of the probe.

In some aspects, a SNP variant probe is used to detect the presence of a CC8 strain. In some aspects, a reference probe is used to detect the absence of a CC8 strain (i.e., a *S. aureus* strain lacking the CC8 strain-specific polymorphism). In other aspects, both the SNP variant probe and the reference probes are used to detect the presence of a mixture of *S. aureus* strains, i.e., the presence of (1) a CC8 strain having the polymorphism; and (2) a *S. aureus* lacking the aforementioned polymorphism. In further aspects, the relative amount of hybridization signals are quantified to estimate the relative quantities of the CC8 strain having the polymorphism and the *S. aureus* lacking the aforementioned polymorphism.

In some aspects, two or more SNP variant probes are used to contact the same nucleic acid or amplicon to detect the presence of two or more CC8 strains. For example, detecting the presence of 3, 4, 5, 6, 7, or 8 CC8 strains using 3, 4, 5, 6, 7, or 8 SNP variant probes.

In other aspects, two or more reference probes are used to contact the same nucleic acid or amplicon to detect the absence of two or more CC8 strains. For example, detecting the absence of 3, 4, 5, 6, 7, or 8 CC8 strains using 3, 4, 5, 6, 7, or 8 reference probes. In yet other aspects, two or more (e.g., 3, 4, 5, 6, 7, or 8) SNP variant probes and two or more (e.g., 3, 4, 5, 6, 7, or 8) reference probes are used together.

In non-limiting aspects, detection is performed by a nucleic acid amplification reaction. In some embodiments the amplification reaction maybe an end-point determination or the amplification reaction maybe quantitative. The quantification may be a real-time PCR method. In some embodiments, the real-time PCR may be a SYBR® Green Assay or a TAQMAN® Assay. Detection, in some embodiments, maybe performed by hybridization using probes specific to target sequences. According to some embodiments, combinations of amplification and hybridization may be used for detection.

As used herein, the term "primers" refer to short nucleic acids. In some embodiments, a primer is annealed to a complementary target DNA strand by nucleic acid hybridization to form a hybrid between the primer and the target DNA strand, and then extended along the target DNA strand by a DNA polymerase enzyme. In further embodiments, one primer pairs are used for amplification of a nucleic acid sequence, e.g., by the polymerase chain reaction (PCR) or other nucleic-acid amplification methods known in the art.

Methods for designing, preparing, and using probes and primers are described, for example, in *Molecular Cloning: A Laboratory Manual,* 2nd ed., vol. 1-3, ed. Sambrook et al., Cold Spring Harbor Laboratory Press, Cold Spring Harbor, N.Y., 1989, and *Current Protocols in Molecular Biology*, ed. Ausubel et al., Greene Publishing and Wiley-Interscience, New York, 1987 (with periodic updates).

It is known in the art that PCR primer pairs can be derived from a known sequence. For example, manually, or by using any of the computer programs intended for that purpose. Nucleic acid probes and primers may readily be prepared based on the nucleic acids provided by this invention. The sequences of the primer pairs are derived from sequences flanking the CC8 strain-specific SNPs disclosed by the present method.

In some aspects, to detect CC8 Clade, the forward primer comprises a sequence within SEQ ID NO: 66. In other aspects, to detect CC8 Clade, the forward primer comprises a sequence 5' of SEQ ID NO: 66, based on known *S. aureus* genome sequence. In yet other aspects, to detect CC8 Clade, the forward primer comprises SEQ ID NO:1.

In some aspects, to detect CC8 Clade, the reverse primer comprises a sequence within SEQ ID NO: 66. In other aspects, to detect CC8 Clade, the reverse primer comprises a reverse complement sequence 3' of SEQ ID NO: 66, based on known *S. aureus* genome sequence. In yet other aspects, to detect CC8 Clade, the forward primer comprises SEQ ID NO:2.

In some aspects, to detect inner CC8 Clade, the forward primer comprises a sequence within SEQ ID NO: 67. In other aspects, to detect inner CC8 Clade, the forward primer comprises a sequence 5' of SEQ ID NO: 67, based on known *S. aureus* genome sequence. In yet other aspects, to detect inner CC8 Clade, the forward primer comprises SEQ ID NO: 5.

In some aspects, to detect inner CC8 Clade, the reverse primer comprises a sequence within SEQ ID NO: 67. In other aspects, to detect inner CC8 Clade, the reverse primer comprises a reverse complement sequence 3' of SEQ ID NO: 67, based on known *S. aureus* genome sequence. In yet other aspects, to detect inner CC8 Clade, the forward primer comprises SEQ ID NO: 6 or 7.

In some aspects, to detect Clade CC8a, the forward primer comprises a sequence within SEQ ID NO: 68. In other aspects, to detect Clade CC8a, the forward primer comprises a sequence 5' of SEQ ID NO: 68, based on known *S. aureus* genome sequence. In yet other aspects, to detect Clade CC8a, the forward primer comprises SEQ ID NO: 10.

In some aspects, to detect Clade CC8a, the reverse primer comprises a sequence within SEQ ID NO: 68. In other aspects, to detect Clade CC8a, the reverse primer comprises a reverse complement sequence 3' of SEQ ID NO: 68, based on known *S. aureus* genome sequence. In yet other aspects, to detect Clade CC8a, the forward primer comprises SEQ ID NO: 11.

In some aspects, to detect Clade CC8b, the forward primer comprises a sequence within SEQ ID NO: 69. In other aspects, to detect Clade CC8b, the forward primer comprises a sequence 5' of SEQ ID NO: 69, based on known *S. aureus* genome sequence. In yet other aspects, to detect Clade CC8b, the forward primer comprises SEQ ID NO: 14.

In some aspects, to detect Clade CC8b, the reverse primer comprises a sequence within SEQ ID NO: 69. In other aspects, to detect Clade CC8b, the reverse primer comprises a reverse complement sequence 3' of SEQ ID NO: 69, based on known *S. aureus* genome sequence. In yet other aspects, to detect Clade CC8b, the forward primer comprises SEQ ID NO: 15.

In some aspects, to detect Clade CC8c, the forward primer comprises a sequence within SEQ ID NO: 70. In other aspects, to detect Clade CC8c, the forward primer comprises a sequence 5' of SEQ ID NO: 70, based on known *S. aureus* genome sequence. In yet other aspects, to detect Clade CC8c, the forward primer comprises SEQ ID NO: 18.

In some aspects, to detect Clade CC8c, the reverse primer comprises a sequence within SEQ ID NO: 70. In other aspects, to detect Clade CC8c, the reverse primer comprises a reverse complement sequence 3' of SEQ ID NO: 70, based on known *S. aureus* genome sequence. In yet other aspects, to detect Clade CC8c, the forward primer comprises SEQ ID NO: 19.

In some aspects, to detect Clade CC8e, the forward primer comprises a sequence within SEQ ID NO: 71. In other aspects, to detect Clade CC8e, the forward primer comprises a sequence 5' of SEQ ID NO: 71, based on known *S. aureus* genome sequence. In yet other aspects, to detect Clade CC8e, the forward primer comprises SEQ ID NO: 22.

In some aspects, to detect Clade CC8e, the reverse primer comprises a sequence within SEQ ID NO: 71. In other aspects, to detect Clade CC8e, the reverse primer comprises a reverse complement sequence 3' of SEQ ID NO: 71, based on known *S. aureus* genome sequence. In yet other aspects, to detect Clade CC8e, the forward primer comprises SEQ ID NO: 23.

In some aspects, to detect Clade CC8f, the forward primer comprises a sequence within SEQ ID NO: 72. In other aspects, to detect Clade CC8f, the forward primer comprises a sequence 5' of SEQ ID NO: 72, based on known *S. aureus* genome sequence. In yet other aspects, to detect Clade CC8e, the forward primer comprises SEQ ID NO: 26.

In some aspects, to detect Clade CC8f, the reverse primer comprises a sequence within SEQ ID NO: 72. In other aspects, to detect Clade CC8f, the reverse primer comprises a reverse complement sequence 3' of SEQ ID NO: 72, based on known *S. aureus* genome sequence. In yet other aspects, to detect Clade CC8e, the forward primer comprises SEQ ID NO: 27.

In some aspects, to detect ST239, the forward primer comprises a sequence within SEQ ID NO: 72. In other aspects, to detect ST239, the forward primer comprises a sequence 5' of SEQ ID NO: 72, based on known *S. aureus* genome sequence. In yet other aspects, to detect Clade CC8e, the forward primer comprises SEQ ID NO: 30.

In some aspects, to detect ST239, the reverse primer comprises a sequence within SEQ ID NO: 72. In other aspects, to detect ST239, the reverse primer comprises a reverse complement sequence 3' of SEQ ID NO: 72, based on known *S. aureus* genome sequence. In yet other aspects, to detect Clade CC8e, the forward primer comprises SEQ ID NO: 31.

In some embodiments, the primer comprises a DNA oligonucleotide 10 nucleotides or more in length. For example, at least 11, 12, 13, 14, 15, 16, 17, 18, 19, 20, 21, 22, 23, 24, 25, or 30 nucleotides.

A primer needs not be 100% complementary to its target DNA or RNA sequence to be specifically hybridizable. A primer is specifically hybridizable when there is a sufficient degree of complementarity to avoid non-specific binding of the primer to non-target sequences under conditions in which specific binding is desired, or under conditions in which an assay is performed.

The disclosure also contemplates the use of primers which comprise a sequence that is essentially identical to one of SEQ ID. NOs.: 1, 2, 5, 6, 7, 10, 11, 12, 14, 15, 18, 19, 22, 23, 26, 27, 30, or 31.

In some embodiments, the primer sequence is essentially identical to one of SEQ ID NOs.: 1, 2, 5, 6, 7, 10, 11, 12, 14, 15, 18, 19, 22, 23, 26, 27, 30, or 31, but differs by one or more (e.g., 1, 2, or 3) nucleotides. In these embodiments, the primer sequence has at least 70% sequence identity to one of SEQ ID NOs.: 1, 2, 5, 6, 7, 10, 11, 12, 14, 15, 18, 19, 22, 23, 26, 27, 30, or 31. For example, at least 75, 80, 85, 86, 87, 88, 89, 90, 91, 92, 93, 94, or 95% sequence identity.

In some embodiments, the difference comprises a substitution. In other embodiments, the difference comprises an insertion. In yet other embodiments, the difference comprises a deletion. In further embodiments, the difference comprises a combination of a substitution, an insertion, and/or a deletion. Such sequence variations are acceptable as long as they do not affect the reliability of the polynucleotide probes in specific binding to the variant or reference sequences.

A probe or primer (such as any of those listed in Table 2) having some homology to a disclosed *Staphylococcus aureus* nucleic acid molecule can form a hybridization complex with a complementary nucleic acid molecule. In particular examples, the probes and primers disclosed herein hybridize to a *Staphylococcus aureus* nucleic acid molecule.

A non-limiting example of a "sample" as used herein is a biological sample. As used herein, biological samples include cells, tissues, and bodily fluids, such as: blood; derivatives and fractions of blood, such as plasma or serum; extracted galls; biopsied or surgically removed tissue, including tissues that are, for example, unfixed, frozen, fixed in formalin and/or embedded in paraffin; tears; milk; skin scrapes; surface washings; urine; sputum; cerebrospinal fluid; prostate fluid; pus; or bone marrow aspirates.

In some embodiments, the sample comprises one or more bacteria colonies. In other embodiments, the sample is obtained from food, environment, or both. In yet other embodiments, the sample is obtained from an animal. In further embodiments, the sample is obtained from a human subject, e.g., a patient.

Exemplary amplification methods include polymerase chain reaction (PCR; see, e.g., U.S. Pat. Nos. 4,683,202; 4,683,195; 4,965,188; and 5,035,996), isothermal procedures (using one or more RNA polymerases (see, e.g., WO 2006/081222), strand displacement (see, e.g., U.S. Pat. No. RE39007E), partial destruction of primer molecules (see, e.g., WO2006087574)), ligase chain reaction (LCR) (see, e.g., Wu, et al., Genomics 4: 560-569 (1990) and/or Barany, et al. PNAS USA 88:189-193 (1991)), Qβ RNA replicase systems (see, e.g., WO/1994/016108), RNA transcription-based systems (e.g., TAS, 3SR), rolling circle amplification (RCA) (see, e.g., U.S. Pat. No. 5,854,033; U.S. Pub. No. 2004/265897; Lizardi et al., Nat. Genet. 19: 225-232 (1998); and/or Bailer et al. Nucleic Acid Res., 26: 5073-5078 (1998)), and strand displacement amplification (SDA) (Little, et al. Clin Chem 45:777-784 (1999)), among others. Many systems are suitable for use in amplifying target nucleic acids and are contemplated herein as would be understood by one of skill in the art. Any of several methods may be used to detect amplified target nucleic acids using primers and/or probes. Many different reagents, systems, and/or detectable labels may be used in the methods described herein. These include, for example, TAQMAN® systems, detectable label-quencher systems (e.g., FRET, salicylate/DTPA ligand systems (see, e.g., Oser et al. Angew. Chem. Int. Engl. 29(10):1167 (1990), displacement hybridization, homologous probes, assays described in EP 070685), molecular beacons (e.g., NASBA), Scorpion, locked nucleic acid (LNA) bases (Singh, et al. Chem Commun 4:455-456 (1998)), peptide nucleic acid (PNA) probes (Pellestor, et al. European J. Human Gen. 12:694-700 (2004)), Eclipse probes (Afonina, et al. Biotechniques 32:940-949 (2002)), light-up probes (Svanvik, et al. Anal Biochem 281:26-35 (2001)), molecular beacons (Tyagi, et al. Nat. Biotechnol. 14:303-308 (1996)), tripartite molecular beacons (Nutiu, et al. Nucleic Acids Res. 30:e94 (2002)), QuantiProbes, HyBeacons (French, et al. Mol. Cell. Probes 15:363-374 (2001)), displacement probes (Li, et al. Nucleic Acids Res. 30:e5 (2002)), HybProbes (Cardullo, et al. PNAS 85:8790-8794 (1988)), MGB Alert, Q-PNA (Fiandaca, et al. Genome Res. 11:609-611 (2001)), Plexor, LUX primers (Nazarenko, et al. Nucleic Acids Res. 30:e37 (2002)), Scorpion primers (Whitcombe, et al. Nat Biotechnol 17:804-807 (1999)), AmpliFluor (Sunrise) primers (Nazarenko, et al. Nucleic Acids Res. 25:2516-2521 (1997)), DzyNA primers (Todd, et al. Clin. Chem. 46:625-630 (2000)), and the like. In each of these assays, the generation of amplification products may be monitored while the reaction is in progress.

An apparatus for detecting the signal generated by the detectable label may be used to detect, measure, and quantify the signal before, during, and/or after amplification. The particular type of signal may dictate the choice of detection method. For example, in some embodiments, fluorescent dyes are used to label probes and/or amplified products. The probes bind to single-stranded and/or double-stranded amplified products, and/or the dyes intercalate into the double-stranded amplified products, and consequently, the resulting fluorescence increases as the amount of amplified product increases. In some embodiments, the $T_m$ is ascertained by observing a fluorescence decrease as the double-stranded amplified product dissociates and the intercalating dye is released therefrom. The amount of fluorescence may be quantitated using standard equipment such as a spectrafluorometer, for example. The use of other methods and/or reagents is also contemplated herein as would be understood by one of skill in the art in view of the teachings of this specification.

As used herein, "real-time PCR" refers to the detection and quantitation of a DNA or a surrogate thereof in a sample. In some embodiments, the amplified segment or "amplicon" can be detected in real time using a 5'-nuclease assay, particularly the TaqMan® assay as described by e.g., Holland et al. (*Proc. Natl. Acad. Sci. USA* 88:7276-7280, 1991); and Heid et al. (*Genome Research* 6:986-994, 1996). For use herein, a TaqMan® nucleotide sequence to which a TaqMan® probe binds can be designed into the primer portion, or known to be present in DNA of a sample.

In some embodiments, the PCR methods use end-point PCR and a positive result is obtained when there is a detectable signal after the PCR is finished. Real-time and end-point PCR methods useful in accordance with the present methods and compositions include, but are not limited to, fluorescence resonance energy transfer (FRET), TAQMAN®, Molecular Beacons, Amplifluor®, Scorpion™, Plexor™, BHQplus™.

When a TaqMan® probe is hybridized to DNA or a surrogate thereof, the 5'-exonuclease activity of a thermostable DNA-dependent DNA polymerase such as SUPERTAQ® (a Taq polymerase from *Thermus aquaticus*, Ambion, Austin, Tex.) digests the hybridized TaqMan® probe during the elongation cycle, separating the fluor from the quencher. The reporter fluor dye is then free from the quenching effect of the quencher moiety resulting in a decrease in FRET and an increase in emission of fluorescence from the fluorescent reporter dye. One molecule of reporter dye is generated for each new molecule synthesized, and detection of the free reporter dye provides the basis for quantitative interpretation of the data. In real-time PCR, the amount of fluorescent signal is monitored with each cycle of PCR. Once the signal reaches a detectable level, it has reached the "threshold or cycle threshold (Ct)." A fluorogenic PCR signal of a sample can be considered to be above background if its Ct value is at least 1 cycle less than that of a no-template control sample. The term "Ct" represents the PCR cycle number when the signal is first recorded as statistically significant. Thus, the lower the Ct value, the greater the concentration of nucleic acid target. In the TaqMan® assay, typically each cycle almost doubles the amount of PCR product and therefore, the fluorescent signal should double if there is no inhibition of the reaction and the reaction was nearly 100% efficient with purified nucleic acid. Certain systems such as the ABI 7500, 7500FAST, 7700 and 7900HT Sequence Detection Systems (Applied Biosystems, Foster City, Calif.) conduct monitoring during each thermal cycle at a pre-determined or user-defined point.

Detection method embodiments using a TaqMan® probe sequence comprise combining the test sample with PCR reagents, including a primer set having a forward primer and a reverse primer, a DNA polymerase, and a fluorescent detector oligonucleotide TaqMan® probe, as well as dNTP's and a salt, to form an amplification reaction mixture; subjecting the amplification reaction mixture to successive cycles of amplification to generate a fluorescent signal from the detector probe; and quantitating the nucleic acid presence based on the fluorescent signal cycle threshold of the amplification reaction.

Protocols and reagents for means of carrying out other 5'-nuclease assays are well known to one of skill in the art, and are described in various sources. For example, 5'-nuclease reactions and probes are described in U.S. Pat. No. 6,214,979 issued Apr. 10, 2001; U.S. Pat. No. 5,804,375 issued Sep. 8, 1998; U.S. Pat. No. 5,487,972 issued Jan. 30, 1996; and U.S. Pat. No. 5,210,015 issued May 11, 1993, all to Gelfand et al.

"$T_m$" refers to the melting temperature (temperature at which 50% of the oligonucleotide is a duplex) of an oligonucleotide determined experimentally or calculated using the nearest-neighbor thermodynamic values of SantaLucia J. et al. (*Biochemistry* 35:3555-62, 1996) for DNA. In general, the $T_m$ of the TaqMan® probe is about 10 degrees above the $T_m$ of amplification primer pairs. The $T_m$ of the MGB probes is calculated using the SantaLucia method with factors correcting for the increased $T_m$ due to MGB.

As used herein, the term "Ct" represents the PCR cycle number when the signal is first recorded as statistically significant. The term "Cq" designates quantification cycle and is interchangeable with the term "Ct" (See e.g., "MIQE: Minimum Information for Publication of Quantitative Real-Time PCR Experiments,"*Clinical Chemistry* 55:4; 611-622 (2009).

As used herein, "amplification" or "amplify" and the like refers to a process that results in an increase in the copy number of a molecule or set of related molecules. Amplification can encompass a variety of chemical and enzymatic processes including without limitation, a polymerase chain reaction (PCR), a strand displacement amplification reaction, a transcription mediated amplification reaction, a nucleic acid sequence-based amplification reaction, a rolling circle amplification reaction, or a ligase chain reaction. According to certain embodiments, following at least one amplification cycle, the amplification products can be detected by sequence or by separation based on their molecular weight or length or mobility, for example.

The term "end-point" measurement refers to a method where data collection occurs only once the reaction has been stopped.

The term "real-time" and "real-time continuous" are interchangeable and refer to a method where data collection occurs through periodic monitoring during the course of the polymerization reaction. Thus, the methods combine amplification and detection into a single step.

A "kit," as used herein, refers to a combination of at least some items for performing a PCR assay for *S. aureus* detection. Embodiments of kits may comprise one or more of the following reagents: at least one set of primers specific for *S. aureus* detection, at least one probe specific for *S. aureus* detection, internal positive control DNA to monitor presence of PCR inhibitors from various food and environmental sources, a baseline control, reagents for sample collection, reagents for isolating nucleic acid such as magnetic beads, spin columns, lysis buffers, proteases, reagents for PCR amplification such as a DNA polymerase or an enzymatically active mutant or variant thereof, a DNA polymerase buffer, deoxyribonucleotides dATP, dCTP, dGTP, or dTTP. In some embodiments, a probe is a TaqMan® probe. In certain kit embodiments, amplification primers are attached to a solid support such as a microarray. In some embodiments, a kit may include an internal control.

One or more kit components may be packaged in one or more container means. Kit container means may generally include at least one vial, test tube, flask, bottle, syringe or other packaging means, into which a component can be placed, and in some embodiments, suitably aliquoted. Where more than one component is included in a kit (they can be packaged together), the kit also will generally contain at least one second, third or other additional container into which the additional components can be separately placed. However, various combinations of components can be packaged in a container means. Kits of the present teachings also will typically include reagent containers in close confinement for commercial sale. Such containers can include injection or blow-molded plastic containers into which the desired container means are retained. When the components of kits are provided in one and/or more liquid solutions, the liquid solution comprises an aqueous solution that can be a sterile aqueous solution.

In certain embodiments, at least one kit component is lyophilized and provided as dried powder(s). For example, primers and TaqMan® probes may be lyophilized. When reagents and/or components are provided as a dry powder, the powder can be reconstituted by the addition of a suitable solvent. In certain embodiments, a solvent is provided in another container means. Kits can also comprise an additional container means for containing a sterile, pharmaceutically acceptable buffer and/or other diluent.

A kit can also include instructions for employing the kit components as well as the use of any other reagent not included in the kit. Instructions can include variations that can be implemented.

In another aspect of the present invention, there is provided a gene microarray or membrane to which a DNA fragment is immobilized, which is useful in the detection of Staphylococcus aureus in a sample obtained from a subject. The gene microarray includes DNA chips effective for detection of a gene corresponding to a probe by hybridization including applying an oligonucleotide probe on the surface of a slide glass treated with a specific chemical reagent. Non-limiting examples of the membrane, which can be used instead of the slide glass in hybridization, include all membranes capable of immobilizing DNA fragments, and preferably, nylon and nitrocellulose membranes.

Spotting the probes on the surface of a slide glass and a membrane can be easily achieved by the conventional technique known in the art. In addition, preparation of probes, hybridization and stripping will be performed according to the conventional techniques common in the art.

In some aspects, the microarray is a collection of microscopic oligonucleotide spots. A DNA microarray (also commonly known as gene chip, DNA chip, or biochip) may be a collection of microscopic DNA spots attached to a solid surface. Probes are synthesized and then attached via surface engineering to a solid surface by a covalent bond to a chemical matrix (via epoxy-silane, amino-silane, lysine, polyacrylamide or others). Solid surfaces are known in the art and include microscopic beads as well as solid supports. In particular, the probes of the present invention may be immobilized on a solid support.

Preferably, the kit of the present invention further comprises reagents for the visualization of the hybridization between any amplification product and the microarray of probes.

In non-limiting embodiments, the length of the sequencing read is at least 13 nucleotides. For example, at least 15, 20, 25, 30, 35, 40, 45, 50, 60, 70, 80, 90, 100, 200, 300, 400, or 1,000 nucleotides. In other embodiments, the sequencing read is between 13-1000, 13-900, 17-900, 17-800, 21-800, 21-700, 25-700, 25-600, 29-600, 29-500, 33-500, 33-400, 37-400, 37-300, 41-300, 41-200, 45-200, 45-100, or 50-100 nucleotides. In further non-limiting embodiments, the sequencing read is between 13-200, 13-190, 17-190, 17-180, 21-180, 21-170, 25-170, 25-160, 29-160, 29-150, 33-150, 33-140, 37-140, 37-130, 41-130, 41-120, 45-120, 45-100, or 50-100 nucleotides.

The sequencing read covers the position of the polymorphism for detection purposes. When the sequencing read is relatively short, for example, 13-15 nucleotides, 100% identity to the sequences flanking the SNP is preferable. When the sequence is relatively long, for example, 50-100 nucleotides, the present disclosure contemplates variability and some sequencing error outside the polymorphism. Thus, for long sequences 100% identity is not as necessary. When an amplicon is used, the present disclosure also contemplates possible errors introduced by PCR, and an even more sequence deviation may be tolerated while preserving the SNP variation for detection purposes.

In some embodiments, the disclosed methods further comprise administering an effective amount of one or more antimicrobial agents to a subject having a S. aureus infection or at risk of developing a S. aureus infection. In these embodiments the antimicrobial agent(s) may be selected from the group that includes, but is not limited to, an Aminoglycoside, such as Amikacin, Gentamicin, Kanamycin, Neomycin, Netilmicin, Streptomycin, Tobramycin or Paromomycin; a Carbacephem, such as Loracarbef; a Carbapenem, such as Ertapenem, Doripenem, Imipenem/Cilastatin or Meropenem; a Cephalosporin, such as Cefadroxil, Cefazolin, Cefalotin, Cefalexin, Cefaclor, Cefamandole, Cefoxitin, Cefprozil, Cefuroxime, Cefixime, Cefdinir, Cefditoren, Cefoperazone, Cefotaxime, Cefpodoxime, Ceftazidime, Ceftibuten, Ceftizoxime, Ceftriaxone, Cefepime or Ceftobiprole; a Glycopeptide, such as Teicoplanin or Vancomycin; a Macrolide, such as Azithromycin, Clarithromycin, Dirithromycin, Erythromycin, Erythroped, Roxithromycin, Troleandomycin, Telithromycin or Spectinomycin; a Monobactam, such as Aztreonam; a Penicillin, such as Amoxicillin, Ampicillin, Azlocillin, Carbenicillin, Cloxacillin, Dicloxacillin, Flucloxacillin, Mezlocillin, Meticillin, Nafcillin, Oxacillin, Penicillin, Piperacillin or Ticarcillin; a Polypeptide, such as Bacitracin, Colistin or Polymyxin B; a Quinolone, such as Ciprofloxacin, Enoxacin, Gatifloxacin, Levofloxacin, Lomefloxacin, Moxifloxacin, Norfloxacin, Ofloxacin or Trovafloxacin; a Sulfonamide, such as Mafenide, Prontosil (archaic), Sulfacetamide, Sulfamethizole, Sulfanilamide (archaic), Sulfasalazine, Sulfisoxazole, Trimethoprim or Trimethoprim-Sulfamethoxazole (Cotrimoxazole) (TMP-SMX); a Tetracycline, such as Demeclocycline, Doxycycline, Minocycline, Oxytetracycline or Tetracycline; as well as Chloramphenicol, Clindamycin, Lincomycin, Fusidic acid, Furazolidone, Linezolid, Metronidazole, Mupirocin, Nitrofurantoin, Macrobid, Platensimycin, Rifampin, or Quinupristin/Dalfopristin. In one embodiment, the disclosed methods further comprise administering to the subject an effective amount of Doxycycline, Linezolid, Rifampin, Trimethoprim-Sulfamethoxazole, Vancomycin or a combination thereof.

In some embodiment, the present disclosure is directed to a method of detecting *Staphylococcus aureus* in a subject, comprising: obtaining *Staphylococcus aureus* nucleic acid from a biological sample, contacting the *Staphylococcus aureus* nucleic acid with one or more CC8 strain-specific polynucleotide probe, detecting specific hybridization of the CC8 strain-specific polynucleotide probe to the *Staphylococcus aureus* nucleic acid and concluding the presence of *Staphylococcus aureus* CC8 Clade, Inner CC8 Clade, Clade CC8a, Clade CC8b, Clade CC8c, Clade CC8e, Clade CC8f, ST239, or a combination thereof.

In other embodiments, the method further comprises amplifying the *Staphylococcus aureus* nucleic acid to produce an amplicon, contacting the amplicon with one or more CC8 strain-specific polynucleotide probe, detecting specific hybridization of the CC8 strain-specific polynucleotide probe to the amplicon and concluding the presence of *Staphylococcus aureus* CC8 Clade, Inner CC8 Clade, Clade CC8a, Clade CC8b, Clade CC8c, Clade CC8e, Clade CC8f, ST239, or a combination thereof.

In further embodiments, the method further comprises contacting *Staphylococcus aureus* nucleic acid with one or more CC8 strain-specific reference polynucleotide probe, detecting specific hybridization of the CC8 strain-specific reference polynucleotide probe to the *Staphylococcus aureus* nucleic acid and concluding the presence of *Staphylococcus aureus* other than CC8 Clade, Inner CC8 Clade, Clade CC8a, Clade CC8b, Clade CC8c, Clade CC8e, Clade CC8f, ST239, or a combination thereof.

In yet further embodiments, the method further comprises amplifying the *Staphylococcus aureus* nucleic acid to produce an amplicon, contacting the amplicon with one or more CC8 strain-specific reference polynucleotide probe, detecting specific hybridization of the CC8 strain-specific reference polynucleotide probe to the amplicon and concluding the presence of *Staphylococcus aureus* other than CC8 Clade, Inner CC8 Clade, Clade CC8a, Clade CC8b, Clade CC8c, Clade CC8e, Clade CC8f, ST239, or a combination thereof.

In some aspects, the relative amount of Clade CC8, Clade Inner CC8, Clade CC8a, Clade CC8b, Clade CC8c, Clade CC8e, Clade CC8f, or Clade ST239 is determined based on the relative intensity between hybridization signal generated using CC8 strain-specific polynucleotide probe and CC8 strain-specific reference polynucleotide probe.

In some embodiment, the present disclosure is directed to a method of detecting *Staphylococcus aureus* in a subject, comprising: obtaining *Staphylococcus aureus* nucleic acid from a biological sample; sequencing the *Staphylococcus aureus* nucleic acid to produce a nucleic acid sequence. Detecting a strain-specific SNP listed in Table 3 indicates the presence of Clade CC8, Clade Inner CC8, Clade CC8a, Clade CC8b, Clade CC8c, Clade CC8e, Clade CC8f, Clade ST239, or a combination thereof. Detecting a strain-specific reference allele listed in Table 3 indicates the absence of Clade CC8, Clade Inner CC8, Clade CC8a, Clade CC8b, Clade CC8c, Clade CC8e, Clade CC8f, Clade ST239, or a combination thereof.

In some aspects, the nucleic acid sequence is at least 10 nucleotides, e.g., at least 11, 12, 13, 14, 15, 16, 17, 18, 19, 20, 25, 30, 35, 40, 45, or 50 nucleotides. In other aspects, any one or more of SEQ ID NOs.: 34, 35, 38, 39, 42, 43, 46, 47, 50, 51, 54, 55, 58, 59, 62, or 63, or the reverse complement thereof is detectable by the nucleic acid sequence.

In some embodiments, amplifying a nucleic acid segment from a sample obtained from the subject with at least one forward primer comprising a nucleic acid sequence selected from the group consisting of SEQ ID NO: 1, 5, 10, 14, 18, 22, 26, and 30; and at least one reverse primer comprising a nucleic acid sequence of SEQ ID NO: 2, 6, 7, 11, 15, 19, 23, 27, and 31 to produce an amplicon; and sequencing the amplicon to detect the *Staphylococcus aureus*.

The invention may further comprise the step of sequencing the amplicon. Methods of sequencing include but need not be limited to any form of DNA sequencing including Sanger, next-generation sequencing, pyrosequencing, SOLiD sequencing, massively parallel sequencing, pooled, and barcoded DNA sequencing.

In Sanger Sequencing, a single-stranded DNA template, a primer, a DNA polymerase, nucleotides and a label such as a radioactive label conjugated with the nucleotide base or a fluorescent label conjugated to the primer, and one chain terminator base comprising a dideoxynucleotide (ddATP, ddGTP, ddCTP, or ddTTP, are added to each of four reaction (one reaction for each of the chain terminator bases). The sequence may be determined by electrophoresis of the resulting strands. In dye terminator sequencing, each of the chain termination bases is labeled with a fluorescent label of a different wavelength that allows the sequencing to be performed in a single reaction.

In pyrosequencing, the addition of a base to a single-stranded template to be sequenced by a polymerase results in the release of a pyrophosphate upon nucleotide incorporation. An ATP sulfurylase enzyme converts pyrophosphate into ATP that in turn catalyzes the conversion of luciferin to oxyluciferin which results in the generation of visible light that is then detected by a camera or other sensor capable of capturing visible light.

In SOLiD sequencing, the molecule to be sequenced is fragmented and used to prepare a population of clonal magnetic beads (in which each bead is conjugated to a plurality of copies of a single fragment) with an adaptor sequence and alternatively a barcode sequence. The beads are bound to a glass surface. Sequencing is then performed through 2-base encoding.

In massively parallel sequencing, randomly fragmented targeted nucleic acids and/or amplicons are attached to a surface. The fragments/amplicons are extended and bridge amplified to create a flow cell with clusters, each with a plurality of copies of a single fragment sequence. The templates are sequenced by synthesizing the fragments in parallel. Bases are indicated by the release of a fluorescent dye correlating to the addition of the particular base to the fragment.

The following examples are given for purely illustrative and non-limiting purposes of the present invention.

EXAMPLES

Example 1. Experimental Methods

Isolate Collection

This study's *S. aureus* isolates, mostly obtained from the CDC's collection, were selected to represent the diversity of known CC8 strains, including USA300, USA500, Iberian, Archaic, Canadian MRSA9 (CMRSA9), and ST239 types, and to encompass both MRSA (313 isolates) and MSSA (119 isolates). Intentionally included were FPR3757 and TCH1516 (prototype USA300 isolates), BD02-25 (the USA500 reference isolate from Li et al. (4) and used in the CDC's quality management system protocols), NRS385 (9)

and ATCC BAA-1763 (two publicly available isolates typed as USA500), and the genomes of COL (an Archaic isolate from 1960 (8)), HPV107 and E2125 (ST247 Iberian strains from the 1960s (21, 22)) and NCTC 8325 (a laboratory strain originally isolated from a septic patient also around 1960). Also included were genomes belonging to the USA300 South American epidemic (USA300-SAE) strain type as well as samples considered "Early Branching USA300" (71, 72, 73), and the Brazilian MRSA-turned-VRSA samples BR-VSSA and BR-VRSA (74). Table 1 lists several of the traditional CC8 strains and their characteristics. Table 2 describes the isolates used in this study that were whole genome sequenced.

Sequencing, SNP Detection, and Phylogenetic Analysis.

Genome libraries for 288 S. aureus isolates were prepared with a 500 base pair insert size using KAPA Library Preparation Kit with Standard PCR Library Amplification (Kapa Biosystems) and sequenced on a 101 bp read, paired-end Illumina GAIIx run or a 2×250 bp Illumina MiSeq run (Table S1). Additionally, 311 S. aureus genomes published in previous studies selected for sequence type diversity were used to generate the CC8 phylogeny and an overall S. aureus phylogeny encompassing several clonal complexes (Table 2) (12, 23).

The bioinformatics pipeline NASP (24) was used to detect SNPs among genomes. In brief, reads were aligned to the finished genome FPR3757 (Genbank accession no. CP000255) using Novoalign (Novocraft.com) and SNPs called with GATK (25). Data filtered out included SNP loci with less than 5× coverage or less than 80% consensus in any one sample, SNP loci that were not present in all genomes in the dataset, and any regions duplicated in the reference genome as identified by NUCmer (26). The results were formatted in a SNP matrix from a core genome common to all isolates in the analysis. Phylogenetic analysis model selection and trees generated from the NASP SNP matrices were performed using IQ-TREE (75) and subsequently plotted with genetic marker data by means of ITOL v3 (28).

S. aureus Typing

Methods for molecular typing of S. aureus were adopted from those previously described (29). These methods are based on a study conducted by the CDC (L. McDougal, unpublished) in which >350 CC8 isolates were tested for multiple genotypic and phenotypic markers including SCCmec type and Iva subtype, Staphylococcus enterotoxin genes sea, seb, sek, and seq, PVL genes, ACME genes, and trimethoprim-sulfamethoxazole resistance. Markers with the greatest sensitivity and specificity for strain typing comprise the original typing algorithm (29).

Figure 4:
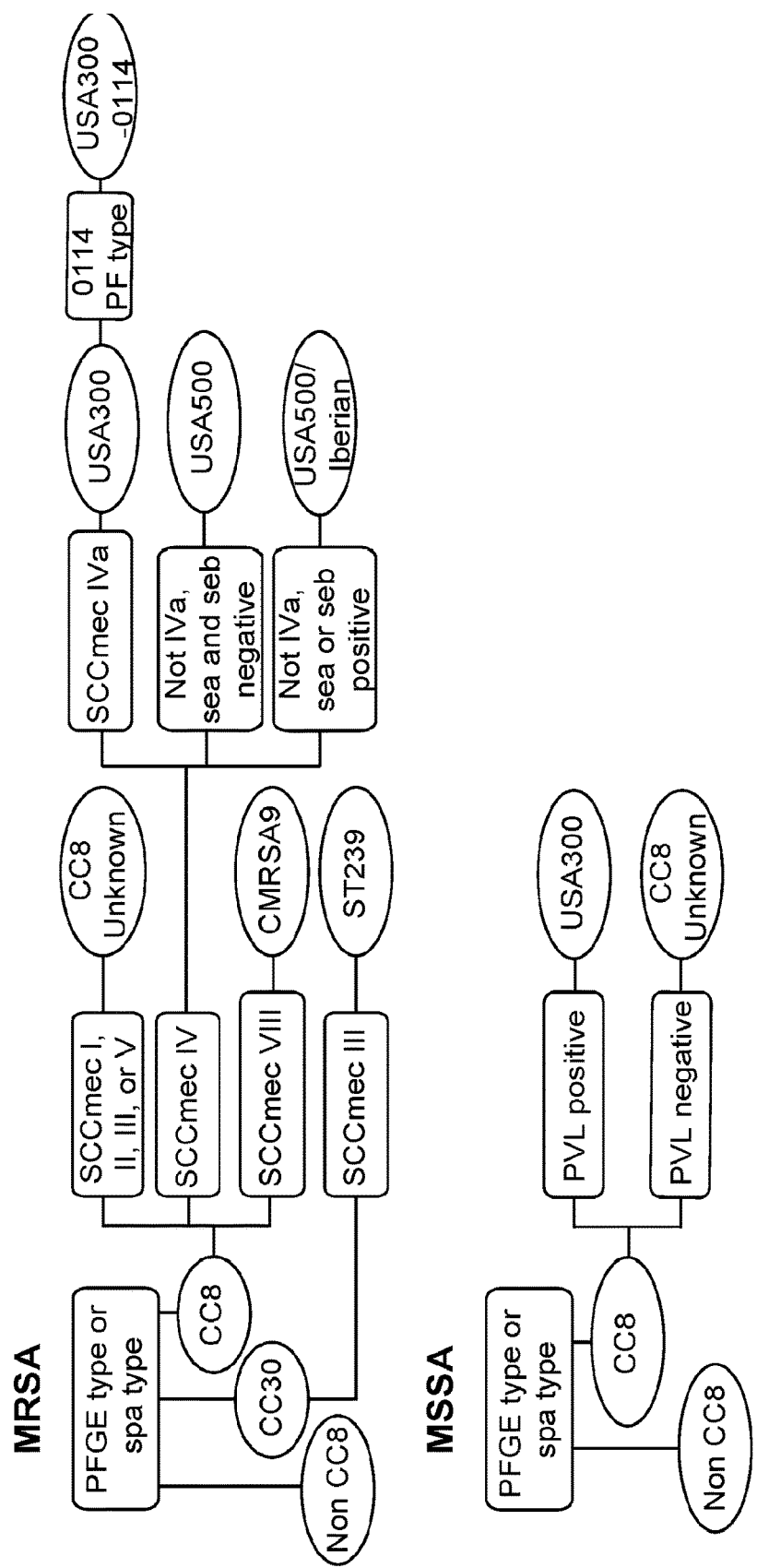
FIG. 4 depicts a genetic marker inference (GMI) methodology used for inferring *S. aureus* strain types using genetic markers.

For purposes of this study, our modified genetic marker typing algorithm is shown in FIG. 4. In brief, traditional PFGE or spa type was used to infer clonal complex. Strain types of CC8 MRSA isolates were inferred based on SCCmec types and toxin gene profiles: SCCmec Iva-positive isolates were called USA300, sea and seb negative isolates with SCCmec IV (other than Iva) were called USA500, and isolates with SCCmec VIII were called CMRSA9. We inferred that the presence of the sea and seb genes were indicative of a separate lineage, called Iberian in Li 2009 (4) and by the CDC in previous surveillance studies (29). However, as the SCCmec I characteristic of the original Iberian strain has largely been replaced by SCCmec IV, and because recent studies have referred to "Iberian" isolates (positive for sea or seb) as USA500 (NRS385 and BAA-1763), we called CC8 isolates positive for sea or seb that carry SCCmec IV (other than Iva) USA500/Iberian to distinguish them from the original Iberian clone. Isolates spatyped as CC30 with SCCmec III were inferred to be ST239. CC8 MSSA isolates were called USA300 if they were PVL positive, and called CC8-Unknown if they were PVL negative. Lastly, we noted whether the USA300 isolates were PF type 0114. This strain typing approach is herein termed the genetic marker inference (GMI) assay.

Multilocus sequence types (MLST) and spa types were determined by the traditional Sanger sequencing analysis or, when typing had not been performed and genomic sequence data were available, MLST was performed with SRST2 (30). SCCmec cassette typing using conventional methods was performed on a subset of isolates depending on the time of their collection (4, 31). To determine SCCmec types for isolates that did not have PCR results and to confirm previous conventional typing, WGS data were used: reads were assembled using SPAdes Genome Assembler (32), and an in silico PCR script using the BioPerl (33) toolkit was used to search for SCCmec typing PCR primer sequences (34) and analyze in silico amplicons. For ten isolates where conventional typing and WGS typing were discordant, raw read data were aligned to sequences of several SCCmec cassette types using SeqMan Ngen® v.12.1.0 (DNASTAR, Madison, Wis.). Types were confirmed by read coverage breadth and depth against the reference SCCmec type sequences.

SNP Assays

SNPs that differentiate specific clades of S. aureus (canS-NPs), identified by NASP and phylogenetic analysis, were exploited for assay design. From the CC8 phylogenetic analysis, SNP loci at which the SNP state differed between a target lineage and the rest of the complex were selected. These loci were then checked in genomes from other clonal complexes to ensure the SNP state was unique to the targeted lineage. In this way, the potential for a shared SNP state across clonal complexes due to recombination (as has been observed (12)) was avoided. Eight sets of primers and probes targeting eight canSNPs were designed with Biosearch Technologies' RealTimeDesign™ software (Biosearch Technologies, Petaluma, Calif.) Assay information is in Table 3.

Cell lysates of 311 isolates were prepared as previously described (35) and used to validate the assays. Reactions were run in 10 µL, on the Applied Biosystems 7500 Fast Real-time PCR instrument (ThermoFisher Scientific) with 5 µL 2× Taqman Universal PCR Master Mix (ThermoFisher Scientific), 80 nM forward and reverse primers, 20 nM each probe, and 1 µL DNA template. Thermal conditions included denaturation at 95° C. for 10 min and 40 cycles of 95° C. for 15 s, 60° C. for 1 min.

Accession number BioProject PRJNA374337 contains the whole genome sequence read data generated in this study.

Example 2. Whole Genome Phylogenetic Analysis

The overall S. aureus phylogeny (FIG. 1) shows the context of CC8 among other S. aureus lineages, and shows that the CC8 strains in this tree all belong to one of three main lineages, ST239 (the HA SCCmec III-carrying MRSA), ST630 (a lineage that branches off basal to the rest of CC8 and comprises five MSSA), and the inner CC8 comprising the other known lineages. Table 1 shows common characteristics of these strain types. This phylogeny comprises 1.84 Mb shared by each genome, and includes large regions exchanged among lineages that resulted in hybrid strains (e.g. ST34 and ST42 of CC30, and ST239 (7).

This tree, therefore, illustrates sum total relationships among lineages within *S. aureus* rather than within-lineage evolutionary history, as removal of these regions would imply a closer than actual relationship between a hybrid strain and one of its parent lineages.

Figure 2:
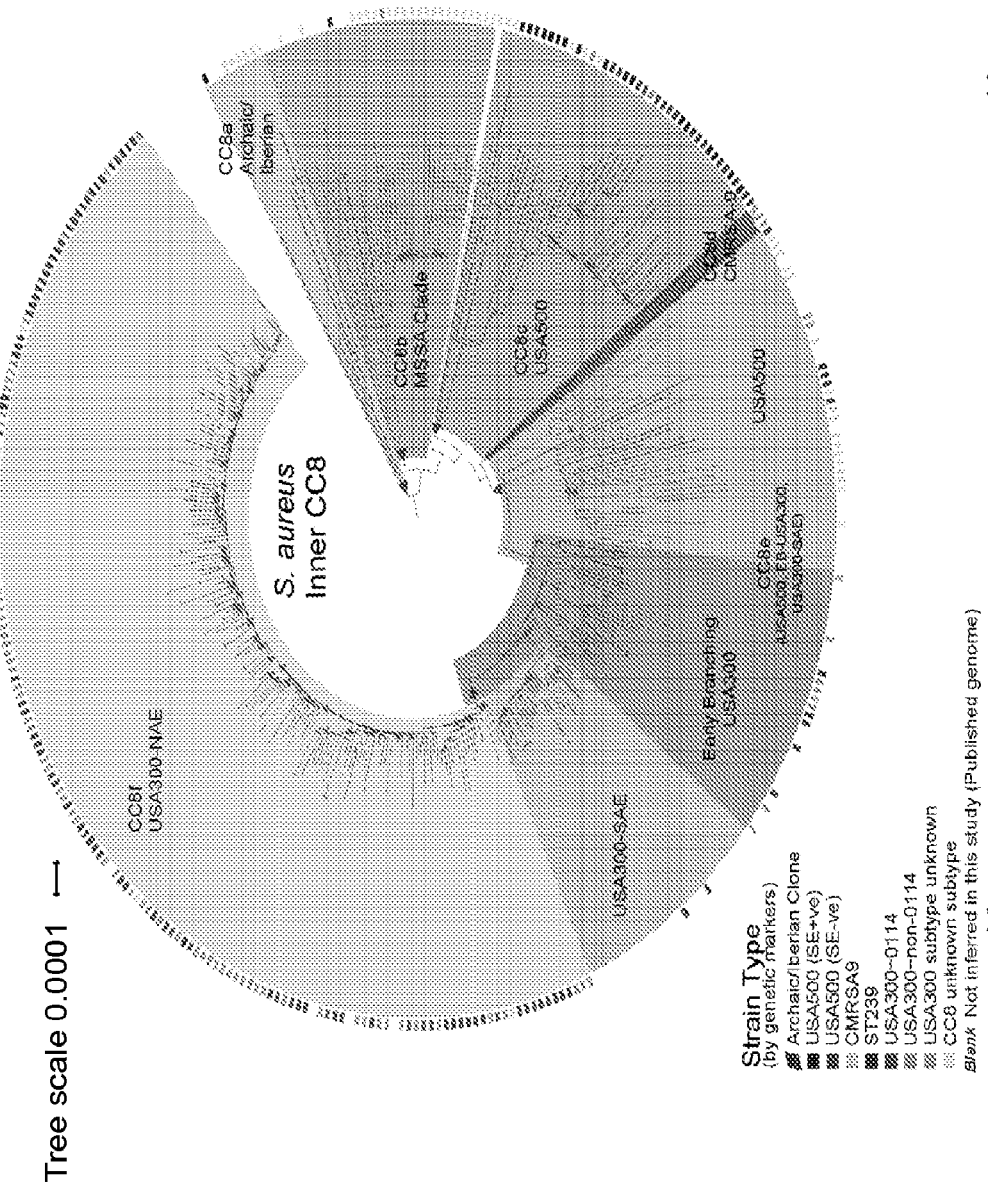
FIG. 2 depicts WGS-based maximum likelihood phylogeny (using the best-fit model TVMe+ASC) of 348 genomes of *S. aureus* (229 MRSA and 119 MSSA) belonging to the inner CC8 clade (excluding ST239 and ST630 genomes), and illustrating the relationship structure of clinically important CC8 groups, and showing that genetic marker inference (GMI) strain typing is not always indicative of genetic relationship. MSSA genomes, on light gray branches, are interspersed among MRSA genomes. This analysis includes 1000 bootstraps of 13,988 SNPs. Nodes with bootstrap values <90% are marked with small triangles. Core genome size is 2.26 Mbp (78.8% of reference genome FPR3757). Branches of the phylogeny on which SNPs were selected for assay development are marked with a large triangle.
Figure 5:
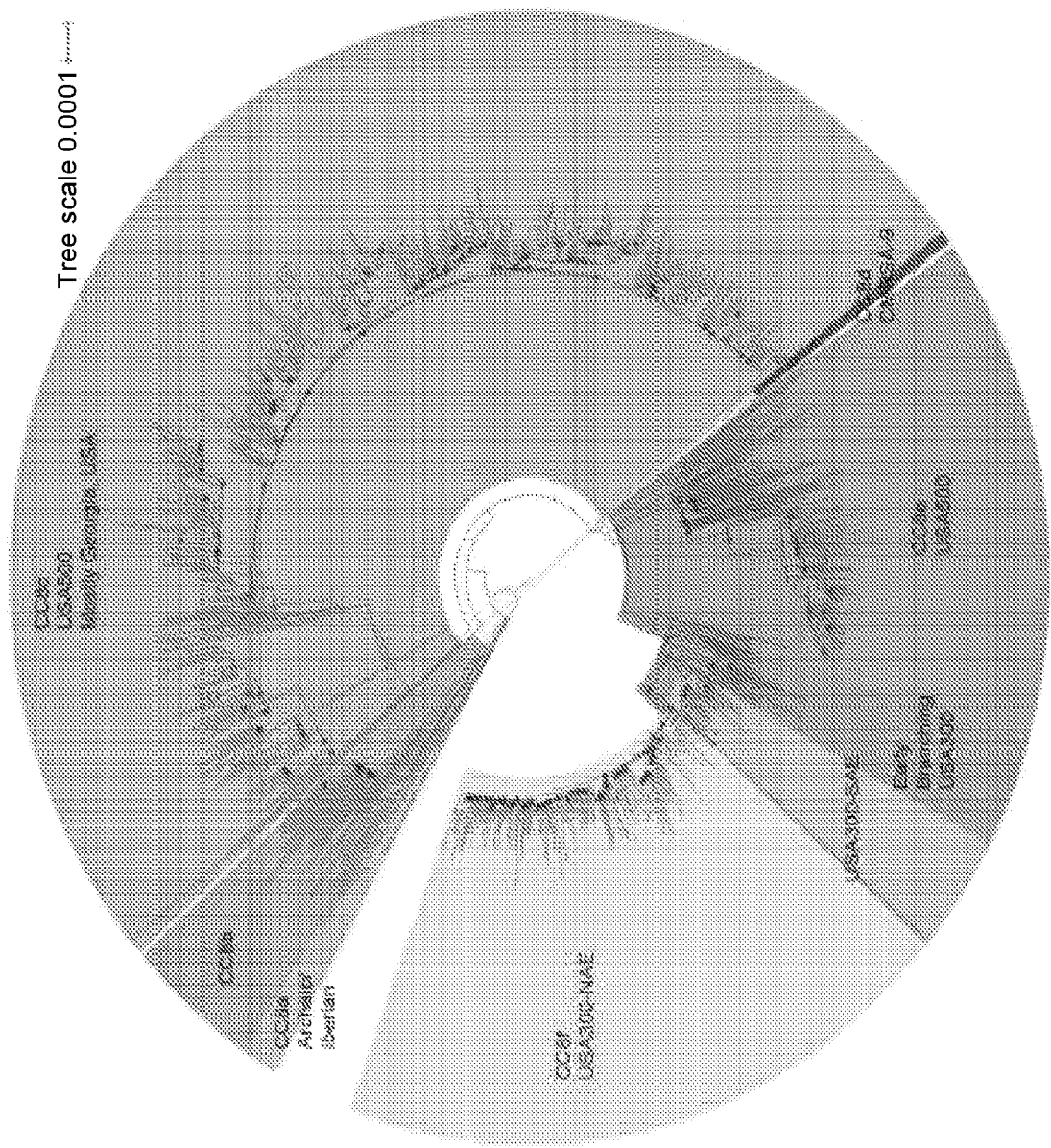
FIG. 5 Maximum likelihood SNP-based phylogeny (using the best-fit model TVMe+ASC) of 839 CC8 genomes: 348 genomes from this study (including the public genomes listed in Table S2), and 491 genomes from companion paper by Frisch et al (BioProject PRJNA342328). CC8 strain groups are labeled according to public literature isolate information and our canonical SNP state definitions. CC8a comprises all old isolates (1960s). CC8b is mostly MSSA and contains NCTC 8325 and the Brazilian BR-VSSA and BR-VRSA genomes (74). CC8c includes two clades, C1 and C2, described in Frisch et al. C2 primarily consists of the Georgia, USA, epidemic strain (Frisch et al). One sample falls between CC8b and CC8c, SA-150 (as noted in FIG. 2). CC8c and CC8e, both considered USA500 groups, are separated phylogenetically by CC8d, the CMRSA9 clade, characterized by SCCmec VIII carriage. Two related samples diverge between CC8d and CC8e, SRR3418706 and SRR3418948 (Frisch et al). CC8e is a paraphyletic group with respect to USA300. Although USA300-SAE and USA300-NAE are considered monophyletic sister clades, it appears there may be other strains circulating that originate from their last common ancestor. (See the Early Branching sample located between USA300-SAE and USA300-NAE, also in FIG. 2.) Purple triangles mark nodes with bootstrap values <90% of 1000 total.

The topology of our inner CC8 SNP-based phylogeny (excluding ST239 and ST630) comprising 348 genomes is similar to those reported recently (16, 36), showing multiple, distinct nested clades, with MSSA (orange branches) interspersed among the MRSA isolates (FIG. 2, Table 1). CC8a, which includes the Archaic and Iberian strains, is the most basal CC8 lineage, which supports the early circulation then disappearance of this lineage over time. All but one MRSA in CC8a carry SCCmec I. To our knowledge, CC8b has not been characterized previously, and contains the old strain NCTC 8325 and the Brazilian VSSA and VRSA isolates, BR-VSSA and BR-VRSA, thought to be closely related to USA300 due to their carriage of SCCmec Iva (74). The majority of the isolates in this clade are MSSA, a few of which carry ACME (suggesting previous SCCmec carriage (37)) or sea, and one of which has the PVL genes. Our phylogeny also shows that isolates known as USA500 fall into two distinct clades separated by CC8d, the Canadian HA-MRSA lineage, CMRSA9 (66): clade CC8c contains NRS385 (9) and BAA-1763 (ATCC), while the group CC8e contains BD02-25 (4). This suggests that the CMRSA9 strains might be defined as USA500 by traditional typing methods. The CC8c clade includes an apparent rapidly expanded lineage (containing BAA-1763), illustrated as shallow branches with low bootstrap support, and several of these isolates were collected in Georgia, U.S. This clade is now known to be an epidemic lineage in Georgia (see companion paper Frisch et al., and FIG. 5).

Genome phylogenetic analysis was performed on *S. aureus* isolates. Specifically, typing information and screening results for all *S. aureus* isolates that were typed by genetic marker inference (GMI, FIG. 3) and by whole genome sequence (WGS) analysis in this study. Of the 295 screened, 224 isolates were typed by GMI and WGS phylogenetic analysis, and 89 of those were then used to validate the SNP strain typing assay panel. A total of 71 isolates were typed by GMI and SNP assay panel, then by WGS phylogenetic analysis for confirmation. Another 137 isolates (not in this table) were screened by GMI and SNP assay panel only (Table 3). Overall, the SNP assays were 100% specific and sensitive on the set of unknown isolates, according to the phylogeny generated through WGS; this result is expected due to the stability of SNPs. The genetic marker inference assay performed fairly well, except in the case of USA500 and USA500/Iberian types, and for MSSA isolates where the only genetic marker for CC8 subtyping was the PVL genes.

Our data support the idea that USA500 in CC8e and USA300 share a direct common ancestor (FIG. 2). The WGS phylogeny indicates that the PVL genes were acquired by an Early Branching USA300 (71) ancestor (nested within CC8e) and passed down to the USA300 lineage, as most USA300 carry PVL, including USA300-SAE (71). As a predictor of USA300, the PVL genes have high sensitivity (97%) and specificity (99%) in our data; however, these genes are not confined to CC8. The phylogeny also confirms that ACME was acquired by the USA300-NAE ancestor and passed vertically, as noted previously (71). ACME is present in six MSSA isolates in CC8f. As ACME is closely associated with SCCmec (37), FIGS. 2 and 3 suggest at least four losses of SCCmec while retaining ACME. Spread across the CC8f USA300-NAE clade are 80 subtype USA300-0114 isolates interspersed with 41 non-0114 isolates, indicating that this important PFGE pattern subtype (20) is not a distinct lineage. Therefore, 0114 strains cannot be phylogenetically distinguished from other USA300 strains, and no canSNP marker can differentiate the 0114 strain type from non-0114 strains.

The incorporation of a significant number of MSSA genomes in the CC8 phylogeny makes it apparent that MSSA was the founder of several of these CC8 strains. A majority of CC8b is MSSA, and the five MRSA in this clade carry four different SCCmec types, suggesting independent acquisitions of the SCCmec cassettes, and much of CC8e remains or has reverted to MSSA. The mostly-MRSA clades are each dominated by a single, different SCCmec type, indicating acquisition by the common ancestor to the clade, except in the Early Branching USA300 group, in which several different SCCmec types exist. All SCCmec types in the Early Branching USA300 group, however, are SCCmec IV subtypes. The MRSA in this clade could be a result of one acquisition event followed by recombination (78), or several separate SCCmec acquisitions. USA300-SAE comprises two SCCmec types, IV and Ivc; however, it is not clear whether the typing schemes used always included a Ivc subtype test. Although USA300-SAE is made up entirely of MRSA, this could be a sampling artifact. Besides their importance in CC8b and CC8e, MSSA genomes are interspersed with the MRSA genomes throughout CC8. The appearance of MSSA dispersed across the CC8 phylogeny supports the idea that the SCCmec cassette is highly mobile, and upholds the notion that MSSA plays a principal role in *S. aureus* evolution and pathology.

Example 3. Assay Screening

Figure 3:
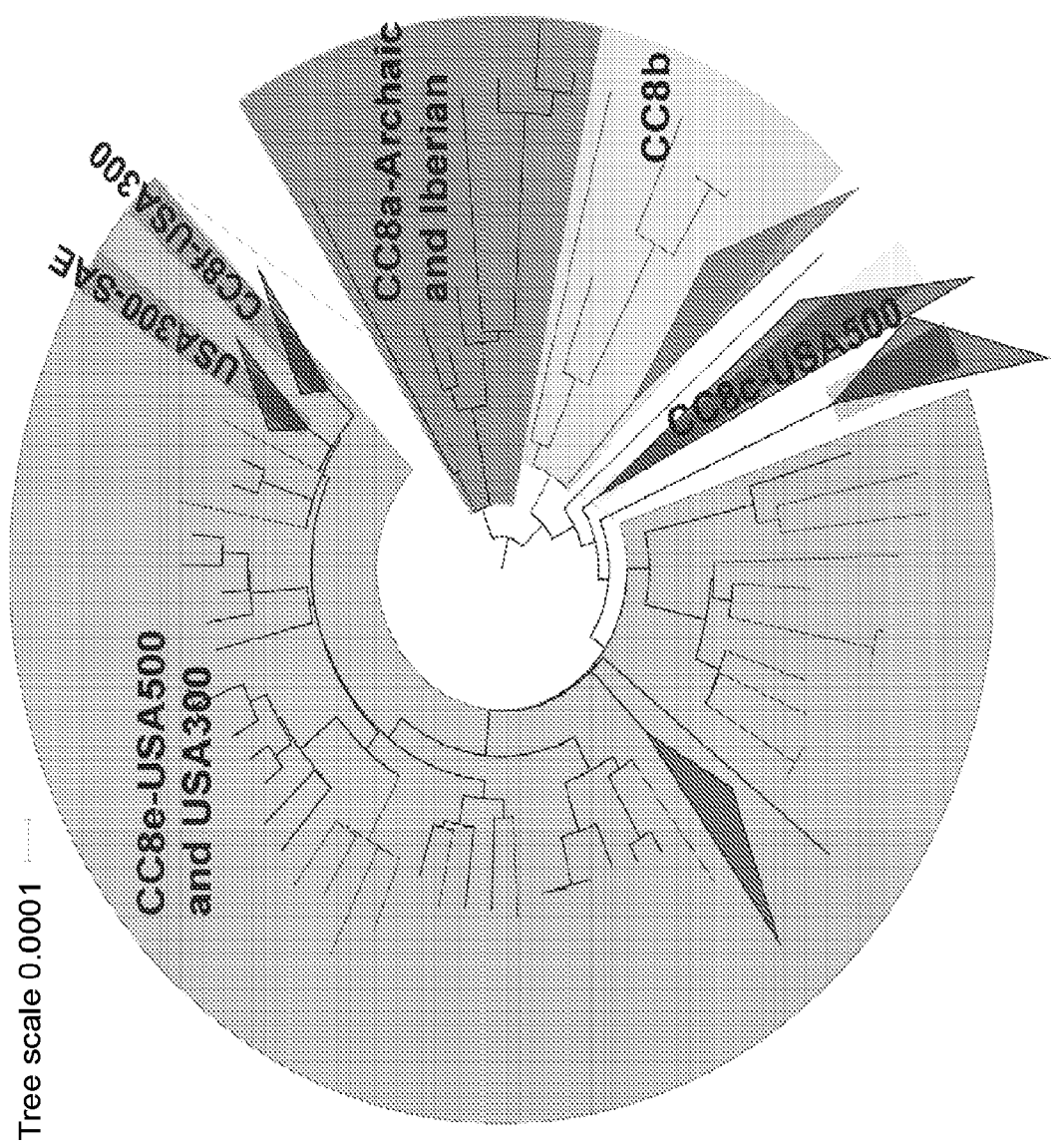
FIG. 3 depicts A circular collapsed view of FIG. 2.

The phylogenetically-informative canSNPs identified using the genomic data presented above and used to design the assays are represented in FIGS. 2 and 3. All assays (Table 2) can be used as stand-alone typing assays for any *S. aureus* except for the CC8b assay, which must be used in combination with either the CC8 assay or the Inner CC8 assay to confirm the phylogenetic placement of an isolate. Although the allelic state that the CC8b assay targets is unique within CC8, some isolates outside of CC8 share this SNP state with the CC8b isolates, possibly due to recombination; therefore, an isolate positive for the CC8b SNP state should be screened across the CC8 or Inner CC8 assay to confirm (or refute) that it falls in CC8b.

Each assay was first validated across a set of isolates used to generate the original phylogeny (WGS followed by SNP assay). In short, the SNP assays performed well and results always agreed with the phylogeny. A second set of 208 isolates that had not been sequenced was then screened, and results from here onward refer to this second set. Here, 144 MRSA and 64 MSSA isolates were compared between GMI and the SNP assay panel (Table 3). Out of the MRSA samples, both methods' distinction between CC8 and non-CC8 isolates was in full agreement; the PFGE/spa strain typing matched the CC8 SNP assay where 114 fell within CC8 while 30 were outside. Out of the MSSA samples, 61 were in agreement that all were CC8, but three isolates called CC8-Unknown by GMI were non-CC8 by SNP assay (Table 3).

Comparison of subtyping within CC8 by GMI and SNP assay panel gave fairly concordant results for MRSA isolates (Table 3). Out of the 114 CC8 screened, 93 fell into their expected clade. Of the other 21, 11 were USA500 (SCCmec IV, negative for sea and seb genes) and two were CC8-

Unknown by GMI and typed as CC8c by SNP panel. Eight isolates typed as a strain for one method for which there was no assay by the other method: seven were CC8-Unknown by GMI and CC8a by SNP panel, and one was CMRSA9 by GMI and CC8-Other by SNP panel. Six of the seven CC8a MRSA isolates were collected in the 1960s, and were SCCmec I positive. This is the SCCmec type observed in the first Archaic and Iberian strains (8) (Table 1), but as these strains seem to have disappeared from circulation, the GMI approach does not account for them. For the 57 isolates typed as USA300 by GMI, all typed in CC8f as expected (Table 2). All USA500/Iberian isolates by GMI were typed as CC8c by SNP panel, and although testing was limited, all four ST239 isolates were concordant between the two typing methods. For MSSA, 45 of the total 64 isolates typed as CC8-Unknown by GMI. These 45 by SNP panel typed as CC8f, CC8e, CC8c, Non-CC8, or CC8-Other. No MSSA isolates typed as non-CC8 by GMI, although three did by SNP panel (Table 3).

A subset of isolates (n=71) were sequenced and added to the CC8 or S. aureus overall phylogeny to determine their true strain type (Table 3, Table 51). All samples in agreement between the two tests also agreed by WGS phylogenetic analysis (n=7). For MRSA, the 11 samples called USA500 by GMI that were CC8c by the SNP panel all typed as CC8c in the phylogeny. CC8-Unknown (GMI)/CC8a (SNP panel) isolates, of which five of the six typed in this study were sequenced, all fell into CC8a. Of the 45 MSSA samples that were labeled as CC8-Unknown by GMI, all the strain types called by SNP panel were corroborated by phylogenetic analysis. The three non-CC8 isolates fell outside of CC8, and were sequence typed as ST6. Of the four CC8-Uknown (GMI)/CC8-Other (SNP panel) isolates, two were sequence typed as ST630, (FIG. 1). The other two diverged after CC8b but before CC8c in the phylogeny (one of these is shown in FIGS. 2 and 3), confirming that both GMI and SNP assay methods were correct but creating previously unseen lineages. It is likely that as we sequence more S. aureus, especially more MSSA, we'll see additional CC8 lineages and a more complex CC8 tree topology develop.

Overall, the SNP assays were 100% specific and sensitive on the set of unknown isolates, according to the phylogeny generated through WGS; this result is expected due to the stability of SNPs. The genetic marker inference assay performed fairly well, except in the case of USA500 and USA500/Iberian types, and for MSSA isolates where the only genetic marker for CC8 subtyping was the PVL genes.

S. aureus remains an important pathogen in healthcare institutions as well as in healthy populations in the community. CC8 strains are among the most prevalent in both environments, especially USA300, and each sub-lineage has different clinical and pathological characteristics (1, 8, 18, 38, 39). Strain typing of S. aureus is important because of these phenotypic differences and their implications on virulence potential, and tracking strains and their prevalence in a healthcare system or network informs epidemiology and infection control practices to help focus resources effectively. Unfortunately, typing is not a routine practice in clinical microbiology laboratories, in part because of the cost, time, and expertise required, as well as the frequent inconclusiveness of results. PFGE, spa typing, and MLST often do not provide the scale of resolution required to determine relationships among a given set of samples, and the presence of particular virulence factors, often located on mobile elements, can be misleading (10). The simple typing system we have developed here, based on presumably stable canSNPs, allows for wide use in clinical laboratories for robust tracking of both MRSA and MSSA infections. Additionally, this method can rapidly and inexpensively assess the possibility of an outbreak or transmission event. Isolates of the same strain type should be investigated further (by WGS), while isolates of different strain types would preclude an outbreak or transmission event, which is just as important (40).

The S. aureus CC8 strain nomenclature, including Iberian, Archaic, USA500, and USA300, was originally based on PFGE typing schemes that used an 80% banding pattern similarity threshold to classify isolates (9). Although adopted for tracking purposes, the continuous evolution and diversification of S. aureus over the years has rendered PFGE a misleading tool for this application. Strains that are within 80% banding pattern similarity may belong to multiple genetic lineages, as shown in this study. USA500 comprises at least two well-established lineages (see companion paper Frisch et al.) and may encompass the Canadian CMRSA9 lineage. Strain BD02-25, called USA500 by Li et al. (4) and currently the CDC's USA500 reference isolate (L. McDougal, unpublished), is not in the same lineage as strains NRS385 (the USA500 reference in McDougal et al. (9) and ATCC BAA-1763, although it is ≥80% similar, suggesting USA500 encompasses a wider genomic range than previously appreciated. Additionally, NRS385 and BAA-1763, which are sea and seb positive, share their clade with several isolates negative for these genes, which were used in the GMI typing scheme. It is necessary to exercise caution in interpretation of typing via mobile elements, as their sensitivity and specificity are not ideal. Likewise, the GMI typing system, although sensitive and specific for USA300-NAE, has limitations. The presence of SCCmec Iva can be used for MRSA but not MSSA isolates, and we show that SCCmec Iva is often found outside USA300-NAE. The presence of PVL, apparently vertically passed to USA300 from its progenitor (13), is a good predictor of USA300, as shown in other studies (10) as well as this one. However the sequencing of the "Early Branching USA300" and USA300-SAE genomes shows that PVL is inclusive of these newly understood strains, and not specific to the highly clonal USA300-NAE (71). Also, we show that MSSA isolates are easily mistyped this way, and PVL is found in other CC8 strains as well as other clonal complexes (10, 41-42). The topologies of several whole genome phylogenies recently generated for CC8 are in agreement (16, 18, 36), despite the differences in interpretations. Li et al. concluded that the USA500 strain is the progenitor of the widespread USA300 strain. Recent studies show that genomes labeled as USA500 fall into a more distant clade from USA300 (CC8c) but that there is an additional clade that shares an ancestor with USA300 (16, 18). We show here that both of these clades contain USA500, and surround the CMRSA9 clade, suggesting CMRSA9 might be considered a USA500 strain. By traditional typing methods, USA500 and other strains named for PF patterns do not represent monophyly. Future studies should note that different lineages contain "USA500" strains, and use WGS phylogenetics or the assays presented here (or the SNPs they target) for strain typing within CC8.

The importance of MRSA is well known. MSSA, on the other hand, continues to have a critical impact on public health (45-47) and remains understudied. MRSA evolution evidences local selection and spread of particular strain types originating from successful MSSA lineages (48) and we demonstrate this within the CC8 lineage. Additionally, diverse MSSA strain types appear ubiquitous (47, 13, 49), and we show that MSSA are present in every major CC8 clade, advancing our understanding of the highly significant role that MSSA plays in *S. aureus* population structure. Importantly, MSSA may ultimately prove more of a challenge to clinically manage, as infection prevention measures targeting particular strain types of MRSA will be less effective against the more diverse MSSA (47). The MSSA in CC8 are interspersed with MRSA, further evidencing the significant mobility of SCCmec (48). Other species of *Staphylococcus* are likely active reservoirs of SCCmec, including the SCCmec Iva characteristic of USA300 (79). The human carriage rate of SCCmec-positive, coagulase-negative *Staphylococcus* (CoNS) can be relatively high, and cocolonization of MSSA and SCCmec-positive CoNS has been observed (79). Regardless of the directionality of SCCmec exchange among species and strains of *Staphylococcus*, the rate of SCCmec acquisition and/or excision may be higher than previously believed, and isolation of only MRSA in healthcare settings will not reveal the entire potential for MRSA carriage or infection.

Additionally, characterization of only MRSA isolates in CC8 (i.e. sampling bias) will give an incomplete evolutionary history of this important clonal complex. In our CC8 phylogeny, MSSA genomes add lineages not represented by MRSA alone, consistent with previous findings in CC8 (13). In our collection, ST630 comprises strictly MSSA isolates. ST630 may be an emerging strain of *S. aureus*, especially in China where recently it reportedly caused a bloodstream infection (as MRSA) (50), endocarditis in a healthy person (as MRSA) (51) and several skin infections (as MSSA) (50, 52). CC8b comprises mostly MSSA, and the three MRSA appear to have emerged separately from different MSSA strains. This clade includes NCTC 8325, a strain isolated in 1943. The ancestor of CC8b diverged early in CC8 evolution like the Archaic lineage. While the Archaic lineage expanded with SCCmec I and has since apparently declined, CC8b does not appear to have acquired and maintained SCCmec, yet contains extant members that cause disease (included in this study). The study and WGS of more MSSA will likely add complexity and clarity to the story of CC8 evolution.

Almost all of the USA300 isolates fall into a distinct clade with distinct features. PFGE profiling of USA300, which was not performed on many isolates in this study, in contrast with our genetic marker-inferred typing, may indeed be 100% concordant with our USA300 SNP-based assay currently. However, USA300 is a relatively young "clone", and as more *S. aureus* lineages develop, a PFGE profiling system using similarity thresholds may soon prove obsolete as it has for other strains and species (53-55). Furthermore, we demonstrate that the PFGE type USA300-0114 is not a "clone" in the phylogenetic sense, as 0114 isolates do not form a monophyletic clade with a common ancestor as was previously believed (56). WGS is irreplaceable to determine if strains of the USA300-0114 PFGE type are part of a single outbreak.

The declining costs and increasingly common use of WGS and phylogenetic analysis allows for discovery of more phylogenetically informative and stable targets that can be used in rapid, relatively simple assays (36, 24, 44). Several advantages to the use of lineage-specific canSNPs as targets include (i) their stability over time, as they're passed vertically through generations, (ii) different SNPs provide different scales of resolution for identifying particular strains (e.g. a CC8-specific SNP versus a USA300-specific SNP) or even species in a given set of samples (44), or for use in global epidemiology (57), regional epidemiology (58), or local cluster analyses (40), and (iii) identification of canSNPs is a straightforward process using whole genome sequence data and publicly available SNP matrix generators (e.g. NASP (24)), followed by parsing the SNPs by sample sets of interest. Here we use real-time PCR assays targeting canSNPs based on WGS to classify isolates into clear evolutionary lineages of CC8, and we illustrate their robustness (working with crude bacterial lysates), and high sensitivity and specificity. Inclusion of assays for SNPs on other branches in a hierarchical fashion, as we've done here, adds confidence to any typing scheme. The hierarchical scheme also provides opportunity to screen clinical or other complex specimens, which may harbor multiple strain types. Although WGS and phylogenetic analysis are irreplaceable in true outbreak situations, WGS is still relatively time-consuming and analysis complex. Robust real-time PCR assays can screen for isolates that may need further investigation with WGS. While WGS gains a foothold in both the public health and clinical laboratory, real-time PCR is a rapid, robust, easy, and therefore universal tool for clinical molecular biology, and provides an excellent vehicle for the assays described here.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

TABLE S1

Accession numbers of previously sequenced *S. aureus* genomes used in this study, along with seven isolates sequenced in this study used solely for the overall *S. aureus* phylogeny (see FIG. 1).

| Sample Name | ST | CC | Accession Information | BioSample | BioProject |
|---|---|---|---|---|---|
| 6850 | 50 | 50 | GCF_000462955.1 | SAMN02604264 | PRJNA216988 |
| 71193 | 398 | 398 | GCF_000258685.1 | SAMN02603419 | PRJNA66999 |

TABLE S1-continued

Accession numbers of previously sequenced *S. aureus* genomes used in this study, along with seven isolates sequenced in this study used solely for the overall *S. aureus* phylogeny (see FIG. 1).

| Sample Name | ST | CC | Accession Information | BioSample | BioProject |
|---|---|---|---|---|---|
| 04_02981 | 225 | 5 | GCA_000025145.2 | SAMN02603764 | PRJNA34809 |
| 08BA02176 | 398 | 398 | GCF_000296595.1 | SAMN02603722 | PRJNA174226 |
| 11819_97 | 80 | 80 | GCF_000239235.1 | SAMN02603886 | PRJNA78269 |
| 55_2053 | 30 | 30 | GCA_000160335.2 | SAMN00103091 | PRJNA34891 |
| ASM38296v1ST228 | 228 | 5 | GCF_000382965.1 | SAMEA2272458 | PRJEA71349 |
| ASM38298v1ST228 | 228 | 5 | GCF_000382985.1 | SAMEA2272299 | PRJEA71351 |
| ASM38300v1ST228 | 228 | 5 | GCF_000383005.1 | SAMEA2272502 | PRJEA71357 |
| Bmb9393 | 239 | 30 | GCF_000418345.1 | SAMN02603524 | PRJNA196937 |
| CA-347 | 45 | 45 | GCF_000412775.1 | SAMN02603909 | PRJNA197422 |
| CC80-11819-97 | 80 | 80 | NC_017351.1 | SAMN02603886 | PRJNA78269 |
| CN1 | 72 | 72 | GCF_000463055.1 | SAMN02603420 | PRJNA162343 |
| COL | 250 | 8 | GCA_000012045.1 | SAMN02603996 | PRJNA238 |
| ECTR2 | 5 | 5 | GCA_000253135.1 | SAMEA2271964 | PRJEA52833 |
| ED133 | 133 | 133 | GCF_000210315.1 | SAMN02604166 | PRJNA41277 |
| ED98 | 5 | 5 | GCF_000024585.1 | SAMN02604165 | PRJNA39547 |
| ERR030256 | 573 | 1 | ERR030256 | SAMEA800337 | PRJEB2295 |
| ERR033301 | 15 | 15 | ERR033301 | SAMEA698687 | PRJEB2478 |
| ERR033313 | 228 | 5 | ERR033313 | SAMEA698507 | PRJEB2478 |
| ERR033335 | 111 | 5 | ERR033335 | SAMEA698256 | PRJEB2478 |
| ERR033336 | 111 | 5 | ERR033336 | SAMEA698255 | PRJEB2478 |
| ERR033358 | 15 | 15 | ERR033358 | SAMEA698616 | PRJEB2478 |
| ERR033382 | 111 | 5 | ERR033382 | SAMEA698445 | PRJEB2478 |
| ERR033386 | 111 | 5 | ERR033386 | SAMEA698295 | PRJEB2478 |
| ERR033411 | 111 | 5 | ERR033411 | SAMEA698614 | PRJEB2478 |
| ERR033426 | 20 | 20 | ERR033426 | SAMEA698330 | PRJEB2478 |
| ERR033530 | 228 | 5 | ERR033530 | SAMEA698184 | PRJEB2478 |
| ERR033544 | 228 | 5 | ERR033544 | SAMEA698667 | PRJEB2478 |
| ERR033561 | 109 | 9 | ERR033561 | SAMEA698205 | PRJEB2478 |
| ERR033570 | 15 | 15 | ERR033570 | SAMEA698267 | PRJEB2478 |
| ERR033576 | 15 | 15 | ERR033576 | SAMEA698266 | PRJEB2478 |
| ERR033598 | 20 | 20 | ERR033598 | SAMEA698551 | PRJEB2478 |
| ERR038664 | 121 | 121 | ERR038664 | SAMEA698598 | PRJEB2478 |
| ERR038670 | 15 | 15 | ERR038670 | SAMEA698626 | PRJEB2478 |
| ERR038695 | 228 | 5 | ERR038695 | SAMEA698390 | PRJEB2478 |
| ERR039392 | 50 | 50 | ERR039392 | SAMEA698655 | PRJEB2478 |
| ERR039394 | 228 | 5 | ERR039394 | SAMEA698652 | PRJEB2478 |
| ERR064902 | 239 | 30 | ERR064902 | SAMEA1029546 | PRJEB2489 |
| ERR064906 | 239 | 30 | ERR064906 | SAMEA1029552 | PRJEB2489 |
| ERR064914 | 239 | 30 | ERR064914 | SAMEA1029514 | PRJEB2489 |
| ERR064918 | 239 | 30 | ERR064918 | SAMEA1029508 | PRJEB2489 |
| ERR064926 | 239 | 30 | ERR064926 | SAMEA1029527 | PRJEB2489 |
| ERR083698 | 30 | 30 | ERR083698 | SAMEA1035650 | PRJEB2862 |
| ERR083699 | 30 | 30 | ERR083699 | SAMEA1035585 | PRJEB2862 |
| ERR083702 | 30 | 30 | ERR083702 | SAMEA1035648 | PRJEB2862 |
| ERR083703 | 30 | 30 | ERR083703 | SAMEA1035671 | PRJEB2862 |
| ERR083722 | 20 | 20 | ERR083722 | SAMEA1035571 | PRJEB2862 |
| ERR083729 | 20 | 20 | ERR083729 | SAMEA1035519 | PRJEB2862 |
| ERR083735 | 20 | 20 | ERR083735 | SAMEA1035624 | PRJEB2862 |
| ERR084580 | 36 | 30 | ERR084580 | SAMEA1033351 | PRJEB2655 |
| ERR084637 | 672 | 361 | ERR084637 | SAMEA1033224 | PRJEB2655 |
| ERR084662 | 36 | 30 | ERR084662 | SAMEA1033348 | PRJEB2655 |
| ERR084743 | 130 | 130 | ERR084743 | SAMEA1033380 | PRJEB2655 |
| ERR084750 | 130 | 130 | ERR084750 | SAMEA1033251 | PRJEB2655 |
| ERR084751 | 130 | 130 | ERR084751 | SAMEA1033270 | PRJEB2655 |
| ERR084761 | 130 | 130 | ERR084761 | SAMEA1033346 | PRJEB2655 |
| ERR084767 | 130 | 130 | ERR084767 | SAMEA1033473 | PRJEB2655 |
| ERR109483 | 12 | 12 | ERR109483 | SAMEA1317131 | PRJEB2755 |
| ERR109486 | 72 | 72 | ERR109486 | SAMEA1317284 | PRJEB2755 |
| ERR109497 | 12 | 12 | ERR109497 | SAMEA1317239 | PRJEB2755 |
| ERR109509 | 7 | 7 | ERR109509 | SAMEA1317097 | PRJEB2755 |
| ERR109518 | 34 | 30 | ERR109518 | SAMEA1317266 | PRJEB2755 |
| ERR109521 | 188 | 188 | ERR109521 | SAMEA1317295 | PRJEB2755 |
| ERR109526 | 39 | 30 | ERR109526 | SAMEA1317228 | PRJEB2755 |
| ERR109531 | 121 | 121 | ERR109531 | SAMEA1317293 | PRJEB2755 |
| ERR109543 | 12 | 12 | ERR109543 | SAMEA1317085 | PRJEB2755 |
| ERR109550 | 34 | 30 | ERR109550 | SAMEA1317122 | PRJEB2755 |
| ERR109553 | 39 | 30 | ERR109553 | SAMEA1317148 | PRJEB2755 |
| ERR109565 | 59 | 59 | ERR109565 | SAMEA1317300 | PRJEB2755 |
| ERR109587 | 7 | 7 | ERR109587 | SAMEA1317273 | PRJEB2755 |
| ERR109588 | 7 | 7 | ERR109588 | SAMEA1317277 | PRJEB2755 |
| ERR109594 | 72 | 72 | ERR109594 | SAMEA1317182 | PRJEB2755 |
| ERR109605 | 672 | 361 | ERR109605 | SAMEA1317234 | PRJEB2755 |
| ERR109611 | 34 | 30 | ERR109611 | SAMEA1317100 | PRJEB2755 |

TABLE S1-continued

Accession numbers of previously sequenced *S. aureus* genomes used in this study, along with seven isolates sequenced in this study used solely for the overall *S. aureus* phylogeny (see FIG. 1).

| Sample Name | ST | CC | Accession Information | BioSample | BioProject |
|---|---|---|---|---|---|
| ERR109617 | 7 | 7 | ERR109617 | SAMEA1317178 | PRJEB2755 |
| ERR109625 | 109 | 9 | ERR109625 | SAMEA1317207 | PRJEB2755 |
| ERR109626 | 7 | 7 | ERR109626 | SAMEA1317116 | PRJEB2755 |
| ERR109628 | 109 | 9 | ERR109628 | SAMEA1317280 | PRJEB2755 |
| ERR109641 | 34 | 30 | ERR109641 | SAMEA1317275 | PRJEB2755 |
| ERR109660 | 672 | 361 | ERR109660 | SAMEA1317150 | PRJEB2755 |
| ERR109684 | 121 | 121 | ERR109684 | SAMEA1317286 | PRJEB2755 |
| ERR114859 | 109 | 9 | ERR114859 | SAMEA1464103 | PRJEB2755 |
| ERR114881 | 6 | 6 | ERR114881 | SAMEA1464159 | PRJEB2755 |
| ERR114897 | 121 | 121 | ERR114897 | SAMEA1464150 | PRJEB2755 |
| ERR114900 | 12 | 12 | ERR114900 | SAMEA1464105 | PRJEB2755 |
| ERR114907 | 39 | 30 | ERR114907 | SAMEA1464138 | PRJEB2755 |
| ERR114928 | 39 | 30 | ERR114928 | SAMEA1464114 | PRJEB2755 |
| ERR114930 | 39 | 30 | ERR114930 | SAMEA1464119 | PRJEB2755 |
| ERR118360 | 22 | 22 | ERR118360 | SAMEA1464668 | PRJEB2756 |
| ERR118477 | 22 | 22 | ERR118477 | SAMEA1464364 | PRJEB2756 |
| ERR118510 | 22 | 22 | ERR118510 | SAMEA1464383 | PRJEB2756 |
| ERR120457 | 36 | 30 | ERR120457 | SAMEA1316744 | PRJEB2394 |
| ERR124466 | 22 | 22 | ERR124466 | SAMEA1464390 | PRJEB2756 |
| ERR127408 | 88 | 88 | ERR127408 | SAMEA1468421 | PRJEB3006 |
| ERR127410 | 88 | 88 | ERR127410 | SAMEA1468425 | PRJEB3006 |
| ERR127411 | 88 | 88 | ERR127411 | SAMEA1468419 | PRJEB3006 |
| ERR127412 | 88 | 88 | ERR127412 | SAMEA1468436 | PRJEB3006 |
| ERR127416 | 88 | 88 | ERR127416 | SAMEA1468416 | PRJEB3006 |
| ERR129302 | 36 | 30 | ERR129302 | SAMEA1464305 | PRJEB2756 |
| ERR134405 | 1 | 1 | ERR134405 | SAMEA1464343 | PRJEB2756 |
| ERR156343 | 101 | 101 | ERR156343 | SAMEA1463380 | PRJEB2655 |
| ERR156345 | 101 | 101 | ERR156345 | SAMEA1463386 | PRJEB2655 |
| ERR156352 | 1943 | 1943 | ERR156352 | SAMEA1463344 | PRJEB2655 |
| ERR156357 | 1943 | 1943 | ERR156357 | SAMEA1463317 | PRJEB2655 |
| ERR156362 | 1943 | 1943 | ERR156362 | SAMEA1463371 | PRJEB2655 |
| ERR156380 | 1943 | 1943 | ERR156380 | SAMEA1463432 | PRJEB2655 |
| ERR156402 | 101 | 101 | ERR156402 | SAMEA1463423 | PRJEB2655 |
| ERR156403 | 101 | 101 | ERR156403 | SAMEA1463425 | PRJEB2655 |
| ERR156404 | 101 | 101 | ERR156404 | SAMEA1463403 | PRJEB2655 |
| ERR156496 | 12 | 12 | ERR156496 | SAMEA1466910 | PRJEB2944 |
| ERR162434 | 573 | | ERR162434 | SAMEA1483437 | PRJEB2097 |
| ERR163371 | 49 | 49 | ERR163371 | SAMEA1484808 | PRJEB2655 |
| ERR163394 | 49 | 49 | ERR163394 | SAMEA1484770 | PRJEB2655 |
| ERR163395 | 1943 | 1943 | ERR163395 | SAMEA1484774 | PRJEB2655 |
| ERR163421 | 49 | 49 | ERR163421 | SAMEA1484738 | PRJEB2655 |
| ERR172025 | 6 | 6 | ERR172025 | SAMEA1523303 | PRJEB2755 |
| ERR172079 | 188 | 188 | ERR172079 | SAMEA1523333 | PRJEB2755 |
| ERR175852 | 50 | 50 | ERR175852 | SAMEA1529816 | PRJEB2655 |
| ERR175870 | 50 | 50 | ERR175870 | SAMEA1529819 | PRJEB2655 |
| ERR175873 | 50 | 50 | ERR175873 | SAMEA1529820 | PRJEB2655 |
| ERR175875 | 50 | 50 | ERR175875 | SAMEA1529867 | PRJEB2655 |
| ERR175902 | 71 | 97 | ERR175902 | SAMEA1529863 | PRJEB2655 |
| ERR175921 | 71 | 97 | ERR175921 | SAMEA1529828 | PRJEB2655 |
| ERR175923 | 133 | 133 | ERR175923 | SAMEA1529838 | PRJEB2655 |
| ERR175942 | 49 | 49 | ERR175942 | SAMEA1529870 | PRJEB2655 |
| ERR182374 | 93 | 93 | ERR182374 | SAMEA1557208 | PRJEB3144 |
| ERR182377 | 93 | 93 | ERR182377 | SAMEA1557239 | PRJEB3144 |
| ERR182379 | 93 | 93 | ERR182379 | SAMEA1557110 | PRJEB3144 |
| ERR182426 | 93 | 93 | ERR182426 | SAMEA1557113 | PRJEB3144 |
| ERR182431 | 93 | 93 | ERR182431 | SAMEA1557200 | PRJEB3144 |
| ERR204157 | 59 | 59 | ERR204157 | SAMEA1572497 | PRJEB3174 |
| ERR204163 | 59 | 59 | ERR204163 | SAMEA1572223 | PRJEB3174 |
| ERR204167 | 6 | 6 | ERR204167 | SAMEA1572322 | PRJEB3174 |
| ERR211682 | 71 | 97 | ERR211682 | SAMEA1565154 | PRJEB2655 |
| ERR211954 | 1 | 1 | ERR211954 | SAMEA1568655 | PRJEB2756 |
| ERR211957 | 80 | 80 | ERR211957 | SAMEA1568653 | PRJEB2756 |
| ERR212760 | 1 | 1 | ERR212760 | SAMEA1572468 | PRJEB3174 |
| ERR212773 | 59 | 59 | ERR212773 | SAMEA1572408 | PRJEB3174 |
| ERR212785 | 80 | 80 | ERR212785 | SAMEA1572531 | PRJEB3174 |
| ERR212817 | 6 | 6 | ERR212817 | SAMEA1572459 | PRJEB3174 |
| ERR212863 | 22 | 22 | ERR212863 | SAMEA1572485 | PRJEB3174 |
| ERR212893 | 6 | 6 | ERR212893 | SAMEA1572368 | PRJEB3174 |
| ERR212922 | 59 | 59 | ERR212922 | SAMEA1572396 | PRJEB3174 |
| ERR212925 | 1 | 1 | ERR212925 | SAMEA1572456 | PRJEB3174 |
| ERR212937 | 1 | 1 | ERR212937 | SAMEA1572234 | PRJEB3174 |
| ERR212960 | 72 | 72 | ERR212960 | SAMEA1572547 | PRJEB3174 |
| ERR212974 | 80 | 80 | ERR212974 | SAMEA1572300 | PRJEB3174 |

TABLE S1-continued

Accession numbers of previously sequenced *S. aureus* genomes used in this study, along with seven isolates sequenced in this study used solely for the overall *S. aureus* phylogeny (see FIG. 1).

| Sample Name | ST | CC | Accession Information | BioSample | BioProject |
|---|---|---|---|---|---|
| ERR217349 | 573 | 1 | ERR217349 | SAMEA1692175 | PRJEB3144 |
| ERR221806 | 573 | 1 | ERR221806 | SAMEA1692198 | PRJEB3144 |
| ERR223117 | 188 | 188 | ERR223117 | SAMEA1317123 | PRJEB2655 |
| ERR223177 | 34 | 30 | ERR223177 | SAMEA1523316 | PRJEB2655 |
| ERR234732 | 133 | 133 | ERR234732 | SAMEA1709027 | PRJEB2655 |
| ERR237566 | 9 | 9 | ERR237566 | SAMEA1708966 | PRJEB2655 |
| ERR237575 | 9 | 9 | ERR237575 | SAMEA1708821 | PRJEB2655 |
| ERR237612 | 133 | 133 | ERR237612 | SAMEA1708935 | PRJEB2655 |
| ERR237615 | 133 | 133 | ERR237615 | SAMEA1708988 | PRJEB2655 |
| ERR246591 | 425 | 425 | ERR246591 | SAMEA1708795 | PRJEB2655 |
| ERR246592 | 425 | 425 | ERR246592 | SAMEA1708779 | PRJEB2655 |
| ERR246595 | 151 | 151 | ERR246595 | SAMEA1708724 | PRJEB2655 |
| ERR246603 | 71 | 97 | ERR246603 | SAMEA1709015 | PRJEB2655 |
| ERR246613 | 425 | 425 | ERR246613 | SAMEA1708788 | PRJEB2655 |
| ERR246618 | 425 | 425 | ERR246618 | SAMEA1708769 | PRJEB2655 |
| ERR246624 | 151 | 151 | ERR246624 | SAMEA1709016 | PRJEB2655 |
| ERR246634 | 151 | 151 | ERR246634 | SAMEA1708875 | PRJEB2655 |
| ERR246637 | 425 | 425 | ERR246637 | SAMEA1708807 | PRJEB2655 |
| ERR246638 | 97 | 97 | ERR246638 | SAMEA1708801 | PRJEB2655 |
| ERR246640 | 151 | 151 | ERR246640 | SAMEA1708737 | PRJEB2655 |
| ERR246641 | 151 | 151 | ERR246641 | SAMEA1708738 | PRJEB2655 |
| ERR246642 | 71 | 97 | ERR246642 | SAMEA1708748 | PRJEB2655 |
| ERR246651 | 97 | 97 | ERR246651 | SAMEA1708972 | PRJEB2655 |
| ERR246669 | 188 | 188 | ERR246669 | SAMEA1708674 | PRJEB2655 |
| ERR246675 | 97 | 97 | ERR246675 | SAMEA1708704 | PRJEB2655 |
| ERR246678 | 97 | 97 | ERR246678 | SAMEA1708714 | PRJEB2655 |
| ERR246679 | 97 | 97 | ERR246679 | SAMEA1708833 | PRJEB2655 |
| ERR266712 | 573 | 1 | ERR266712 | SAMEA1876983 | PRJEB3201 |
| ERR279017 | 772 |  | ERR279017 | SAMEA1903474 | PRJEB3201 |
| ERR279025 | 772 |  | ERR279025 | SAMEA1903479 | PRJEB3201 |
| ERR279027 | 772 |  | ERR279027 | SAMEA1903484 | PRJEB3201 |
| ERR279028 | 772 |  | ERR279028 | SAMEA1903485 | PRJEB3201 |
| ERR294328 | 121 | 121 | ERR294328 | SAMEA1904160 | PRJEB2655 |
| FPR3757 | 8 | 8 | NC_007793.1 | SAMN04485900 | PRJNA311575 |
| HO_5096_0412 | 22 | 22 | GCA_000284535.1 | SAMEA2272552 | PRJEA71279 |
| JH1 | 105 | 5 | GCF_000017125.1 | SAMN02598344 | PRJNA15758 |
| JH9 | 105 | 5 | GCF_000016805.1 | SAMN02598343 | PRJNA15757 |
| JKD6008 | 239 | 30 | GCF_000145595.1 | SAMN02603619 | PRJNA29567 |
| JKD6159 | 93 | 93 | GCF_000144955.1 | SAMN02604217 | PRJNA50759 |
| LGA251 | 425 | 425 | GCF_000237265.1 | SAMEA2272771 | PRJEA62883 |
| M013 | 59 | 59 | GCF_000237125.1 | SAMN02603643 | PRJNA78007 |
| MRSA252 | 36 | 30 | GCF_000011505.1 | SAMEA1705935 | PRJNA265 |
| MSSA476 | 1 | 1 | GCA_000011525.1 | SAMEA1705922 | PRJNA266 |
| Mu3 | 5 | 5 | GCA_000010445.1 | SAMD00060910 | PRJDA18509 |
| Mu50 | 5 | 5 | GCF_000009665.1 | SAMN03859718 | PRJNA289526 |
| MW2 | 1 | 1 | NC_003923.1 | SAMN02146859 | PRJNA203440 |
| N315 | 5 | 5 | GCF_000009645.1 | SAMD00061099 | PRJNA264 |
| NCTC8325 | 8 | 8 | ERS980038 | SAMEA3672889 | PRJEB6403 |
| Newman | 254 | 8 | NC_009641.1 | SAMD00060913 | PRJDA18801 |
| RF122 | 151 | 151 | GCF_000009005.1 | SAMEA3138186 | PRJNA63 |
| SA40 | 59 | 59 | GCF_000470865.1 | SAMN02603110 | PRJNA167373 |
| SA957 | 59 | 59 | GCF_000470845.1 | SAMN00996491 | PRJNA167119 |
| SO385 | 398 | 398 | GCA_000009585.1 | SAMEA2272644 | PRJEA29427 |
| SRR278168 | 36 | 30 | SRR278168 | SAMN00627119 | PRJNA60659 |
| SRR445079 | 398 | 398 | SRR445079 | SAMN00811608 | PRJNA274898 |
| SRR445080 | 398 | 398 | SRR445080 | SAMN00811609 | PRJNA274898 |
| SRR445081 | 398 | 398 | SRR445081 | SAMN00811610 | PRJNA274898 |
| SRR445083 | 398 | 398 | SRR445083 | SAMN00811612 | PRJNA274898 |
| SRR445228 | 398 | 398 | SRR445228 | SAMN00828618 | PRJNA274898 |
| SRR630647 | 72 | 72 | SRR630647 | SAMN00809171 | PRJNA88947 |
| SRR630944 | 72 | 72 | SRR630944 | SAMN00809171 | PRJNA88947 |
| SRR647628 | 188 | 188 | SRR647628 | SAMN00792143 | PRJNA88593 |
| SRR747872 | 672 | 361 | SRR747872 | SAMN01906556 | PRJNA185257 |
| T0131 | 239 | 30 | GCF_000204665.1 | SAMN02603905 | PRJNA65323 |
| TCH1516 | 8 | 8 | GCA_000017085.1 | SAMN00253845 | PRJNA19489 |
| TCH60 | 8 | 8 | GCA_000159535.2 | SAMN00002240 | PRJNA31539 |
| TW20 | 239 | 30 | GCA_000027045.1 | SAMEA2272282 | PRJEA36647 |
| USA300_ISMMS1 | 8 | 8 | GCF_000568455.1 | SAMN03081531 | PRJNA237099 |

TABLE S1-continued

Accession numbers of previously sequenced *S. aureus* genomes used in this study, along with seven isolates sequenced in this study used solely for the overall *S. aureus* phylogeny (see FIG. 1).

| Sample Name | ST | CC | Accession Information | BioSample | BioProject |
|---|---|---|---|---|---|
| VC40 | 8 | 8 | GCF_000245495.1 | SAMN02603393 | PRJNA66591 |
| Z172 | 239 | 30 | GCF_000485885.1 | SAMN02370325 | PRJNA222409 |
| USA1000-94318-NRS483 | 59 | 59 | SRR1014718 | SAMN02314230 | PRJNA214785 |
| USA300-CA-263-NRS647 | 8 | 8 | SRR1014698 | SAMN02314210 | PRJNA214785 |
| USA200-OR-131-NRS722 | 36 | 30 | SRR1014721 | SAMN02314233 | PRJNA214785 |
| USA100-NRS382 | 5 | 5 | SRR1014713 | SAMN02314225 | PRJNA214785 |
| USA1100-04031 | 30 | 30 | SRR1014719 | SAMN02314231 | PRJNA214785 |
| USA200-NRS383 | 346 | 30 | SRR1014720 | SAMN02314232 | PRJNA214785 |
| USA400-BAA1752 | 1 | 1 | SRR1014703 | SAMN02314215 | PRJNA214785 |
| USA500-NRS385 | 8 | 8 | SRR1014700 | SAMN02314212 | PRJNA214785 |
| USA600-BAA1751 | 45 | 45 | SRR1014725 | SAMN02314237 | PRJNA214785 |
| USA600-BAA1754 | 45 | 45 | SRR1014722 | SAMN02314234 | PRJNA214785 |
| USA600-NRS22 | 45 | 45 | SRR1015085 | SAMN02314238 | PRJNA214785 |
| USA600-NY-315 | 45 | 45 | SRR1014723 | SAMN02314235 | PRJNA214785 |
| USA700-NRS386 | 72 | 72 | SRR1014706 | SAMN02314221 | PRJNA214785 |
| USA800-NRS387 | 5 | 5 | SRR1014708 | SAMN02314220 | PRJNA214785 |
| USA900-20210 | 15 | 15 | SRR1014704 | SAMN02314216 | PRJNA214785 |
| 1-29971CC182 | 182 | | This study | This study | This study |
| 2-68462CC9 | 9 | | This study | This study | This study |
| 3-68192CC7 | 7 | | This study | This study | This study |
| 4-68181CC509 | 509 | | This study | This study | This study |
| 5-68179CC15 | 15 | | This study | This study | This study |
| 6-46279CC121 | 121 | | This study | This study | This study |
| 9-40561CC59 | 59 | | This study | This study | This study |

TABLE 1

Characteristics and reference isolates of lineages of CC8.

| Traditional strain nomenclature | Known isolates (alias) | Isolate references | Main SCCmec type | Main spa type | Main sequence clade | WGS-based |
|---|---|---|---|---|---|---|
| ST239 | JKD6008, T0131, TW20 | (59-61) | III | t037, t431, t030 | ST239 | ST239 |
| ST630 | Unknown | — | V[a] | t377[a], t4549[a] | ST630 | ST630 |
| Archaic | Newman, COL, NCTC 10442 | (8, 9, 62, 63) | I | t051 | ST250 | CC8a |
| Iberian | HPV107, PER34, EMRSA5, E2125, NRS209 (28243, NR-46003) | (8, 9, 15, 21, 22, 64, 65) | I | t051 | ST247 | CC8a |
| — | NCTC 8325, BR-VRSA | (74, 65) | II, III, Iva[b] | t334 | ST8, ST1181 | CC8b |
| USA500/Iberian[c] | NRS385 (95938, NR-46071), BAA-1763 (GA229) | (15) | IV | t064 | ST8 | CC8c |
| CMRSA9 | 01S-0965 | (66, 67) | VIII | t008 | ST8 | CC8d |
| USA500[c] | BD02-25, CA-224 (NRS645, NR-46174) | (4, 15) | IV | t008 | ST8 | CC8e |
| Early Branching USA300 | V2200, HUV05 | (71) | IV | t008 | ST8 | CC8e |
| USA300-NAE | FPR3757, TCH1516 (USA300-HOU-MR) | (68-70) | Iva | t008 | ST8 | CC8f |
| USA300-SAE | M121, CA12 | (71) | Ivc | t008 | ST8 | CC8e |

[a]t377 based on this study, SCCmec V and t4549 based on one MRSA isolate (51).
[b]Each SCCmec type is based on one MRSA isolate. Most isolates in this clade are MSSA.
[c]We've made the distinction between USA500 and USA500/Iberian, as recent work (including CDC unpublished data and Albrecht 2015 (29)) have characterized new isolates based on the presence of sea and seb genes (4) and SCCmec IV.

TABLE 2

Assays designed and validated in this study.

| Assay name | Primer/Probe name | Probe labels | Sequence[a] | Product length (bp) | SEQ ID NO. |
|---|---|---|---|---|---|
| *CC8 Clade (including ST239 and ST630)* | | | | | |
| CC8_B+ | tCC8_F | | CGAGTCAGCTAGTGGTCCGTT | 88 | 1 |
| | tCC8_R | | ATGCATAGCTCTTGCTAAAGTGTA | | 2 |
| | tCC8-A_FB+ | FAM, BHQ-1plus | ACCTATACCTGAACGTCAA | | 3 |
| | non-tCC8-G_TB+ | TET, BHQ-1plus | CTATACCTGAGCGTCAAA | | 4 |
| *Inner CC8 Clade (excluding ST239 and ST630)* | | | | | |
| inCC8_B+ | inCC8_F | | TGCCCATAACACATTTGACACTTT | 79 | 5 |
| | inCC8_R1 | | TTCGGCCACAGCTAAACTCG | | 6 |
| | inCC8_R2 | | GTTCGGCTACAGCTAAACTTGC | | 7 |
| | inCC8_FB+ | FAM, BHQ-1plus | ATCGGACCCGGTAACC | | 8 |
| | non-inCC8_TB+ | TET, BHQ-1plus | TAATCGGACCTGGTAACC | | 9 |
| *Clade CC8a (Archaic and Iberian)* | | | | | |
| CC8a_B+ | CC8a_F | | CGCCAAATGACTCGCATTGT | 241 | 10 |
| | CC8a_R | | GCATGTGCCTTTCCGAARTAAA | | 11 |
| | CC8a-C_FB+ | FAM, BHQ-1plus | ATTACTGTAGCAGGGCTG | | 12 |
| | nonCC8a-T_TB+ | TET, BHQ-1plus | CTGTAGCAGGGTTGC | | 13 |
| *Clade CC8b* | | | | | |
| CC8b_B+ | CC8b_F | | GATGACGTGATAACTGTACGTSGAT | 240 | 14 |
| | CC8b_R | | CGCGATTGAGGGTGAATATTGC | | 15 |
| | CC8b-C_FB+ | FAM, BHQ-1plus | AAGCTAACAAAATCACCTACTG | | 16 |
| | nonCC8b-T_TB+ | TET, BHQ-1plus | CAAAGCTAACAAAATTACCTAC | | 17 |
| *Clade CC8c (USE500/Iberian)* | | | | | |
| NewIber_B+ | NewIber_F | | GCGCAACAGGGAAGCAA | 118 | 19 |
| | NewIber_R | | TGCGGATGTCCTATGTCTGAAAG | | 18 |
| | NewIber-T_FB+ | FAM, BHQ-1plus | TGCACTTACATATCATCCAT | | 20 |
| | nonNewIber-C_TB+ | TET, BHQ-1plus | CACTTACATACCATCCATC | | 21 |
| *Group CC8e[b] (USA500, Early Branching USA300, and USA300-SAE)* | | | | | |
| CC8e_B+ | CC8e_F | | ACCTTATACRGAACATAGCAGACG | 106 | 22 |
| | CC8e_R | | TCGATGCGCTTCTATCACTTC | | 23 |
| | CC8e-C_FB+ | FAM, BHQ-1plus | TATTAGATGAAGGCCTCAATA | | 24 |
| | nonCC8e-T_TB+ | TET, BHQ-1plus | TTTATTAGATGAAGGTTCAATA | | 25 |
| *Clade CC8f[b] (USA300-NAE)* | | | | | |
| CC8f_B+ | CC8f_F | | CCTGAAGAAGAAGAGCGTTTAAGAA | 208 | 26 |
| | CC8f_R | | RCATCCTACGATGGCCGAATC | | 27 |
| | CC8f-T_FB+ | FAM, BHQ-1plus | TAAACGTCGTAAAGTAGAACAA | | 28 |
| | nonCC8f-A_TB+ | TET, BHQ-1plus | ACGTAAACGTCGTAAAGAAGAAC | | 29 |

TABLE 2-continued

Assays designed and validated in this study.

| Assay name | Primer/ Probe name | Probe labels | Sequence[a] | Product length (bp) | SEQ ID NO. |
|---|---|---|---|---|---|
| ST239 | | | | | |
| ST239_B+ | ST239_F | | CATGACCGCCACTATAACCAGA | 99 | 30 |
| | ST239_R | | ATGCAACATTAGCAGGAGGATG | | 31 |
| | ST239-C_FB+ | FAM, BHQ-1plus | TACGACTGACCTGATGC | | 32 |
| | non239-T_TB+ | TET, BHQ-1plus | CGACTGACTTGATGCC | | 33 |

[a]Nucleotides in bold in each probe sequence are the phylogenetically-informative canonical SNP state targeted by the assay.
[b]USA300-NAE isolates will also test positive on this assay.

TABLE 3

Comparison of typing *S. aureus* isolates by the genetic marker inference assay and real-time PCR SNP assays on unknown (not sequenced) samples. Numbers in parentheses are the number of isolates that were subsequently whole genome sequenced to determine true strain type.

| Genetic marker inference | CC8 | Clade CC8a | Clade CC8b | Clade CC8c | Group CC8e | Clade CC8f | ST239 | CC8 Other | Non-CC8 | Total |
|---|---|---|---|---|---|---|---|---|---|---|
| MRSA | | | | | | | | | | |
| CC8 | 11 | 7 | 0 | 34 | 11 | 57 | 4 | 1 | 0 | 114 |
| CC8-Unknown | 9 | 7 (5) | 0 | 2 (0) | 0 | 0 | 0 | 0 | 0 | 9 |
| USA500/Iberian | 21 | 0 | 0 | 21 (3) | 0 | 0 | 0 | 0 | 0 | 21 |
| CMRSA9 | 1 | 0 | 0 | 0 | 0 | 0 | 0 | 1 (0) | 0 | 1 |
| USA500 | 22 | 0 | 0 | 11 (11) | 11 (3) | 0 | 0 | 0 | 0 | 22 |
| USA300 | 57 | 0 | 0 | 0 | 0 | 57 (1) | 0 | 0 | 0 | 57 |
| ST239 | 4 | 0 | 0 | 0 | 0 | 0 | 4 (0) | 0 | 0 | 4 |
| Non-CC8 | 0 | 0 | 0 | 0 | 0 | 0 | 0 | 0 | 30 (0) | 30 |
| Total | 11 | 7 | 0 | 34 | 11 | 57 | 4 | 1 | 30 | 144 |
| MSSA | | | | | | | | | | |
| CC8 | 61 | 0 | 18 | 4 | 15 | 20 | 0 | 4 | 3 | 64 |
| CC8-Unknown | 45 | 0 | 18 (18) | 4 (4) | 15 (15) | 4 (4) | 0 | 4 (4) | 3 (3) | 48 |
| USA300 | 16 | 0 | 0 | 0 | 0 | 16 (0) | 0 | 0 | 0 | 16 |

REFERENCES

1. Bal A M, Coombs G W, Holden M T, Lindsay J A, Nimmo G R, Tattevin P, Skov R L. 2016. Genomic insights into the emergence and spread of international clones of healthcare-, community- and livestock-associated methicillin-resistant *Staphylococcus aureus*: Blurring of the traditional definitions. J Glob Antimicrob Resist 6:95-101.
2. Carrel M, Perencevich E N, David M Z. 2015. USA300 Methicillin-Resistant *Staphylococcus aureus*, United States, 2000-2013. Emerg Infect Dis 21:1973-1980.
3. Diekema D J, Richter S S, Heilmann K P, Dohrn C L, Riahi F, Tendolkar S, McDanel J S, Doern G V. 2014. Continued emergence of USA300 methicillin-resistant *Staphylococcus aureus* in the United States: results from a nationwide surveillance study. Infect Control Hosp Epidemiol 35:285-292.
4. Li M, Diep B A, Villaruz A E, Braughton K R, Jiang X, DeLeo F R, Chambers H F, Lu Y, Otto M. 2009. Evolution of virulence in epidemic community-associated methicillin-resistant *Staphylococcus aureus*. Proc Natl Acad Sci USA 106:5883-5888.
5. Harris S R, Feil E J, Holden M T, Quail M A, Nickerson E K, Chantratita N, Gardete S, Tavares A, Day N, Lindsay J A, Edgeworth J D, de Lencastre H, Parkhill J, Peacock S J, Bentley S D. 2010. Evolution of MRSA during hospital transmission and intercontinental spread. Science 327:469-474.
6. Wang Z, Zhou H, Wang H, Chen H, Leung K K, Tsui S, Ip M. 2014. Comparative genomics of methicillin-resistant *Staphylococcus aureus* ST239: distinct geographical variants in Beijing and Hong Kong. BMC Genomics 15:529.
7. Robinson D A, Enright M C. 2004. Evolution of *Staphylococcus aureus* by large chromosomal replacements. J Bacteriol 186:1060-1064.
8. Chambers H F, Deleo F R. 2009. Waves of resistance: *Staphylococcus aureus* in the antibiotic era. Nat Rev Microbiol 7:629-641.
9. McDougal L K, Steward C D, Killgore G E, Chaitram J M, McAllister S K, Tenover F C. 2003. Pulsed-field gel electrophoresis typing of oxacillin-resistant *Staphylococcus aureus* isolates from the United States: establishing a national database. J Clin Microbiol 41:5113-5120.
10. David M Z, Taylor A, Lynfield R, Boxrud D J, Short G, Zychowski D, Boyle-Vavra S, Daum R S. 2013. Comparing pulsed-field gel electrophoresis with multilocus sequence typing, spa typing, staphylococcal cassette chromosome mec (SCCmec) typing, and PCR for panton-valentine leukocidin, arcA, and opp3 in methicillin-resistant *Staphylococcus aureus* isolates at a U.S. Medical Center. J Clin Microbiol 51:814-819.
11. Nubel U, Roumagnac P, Feldkamp M, Song J H, Ko K S, Huang Y C, Coombs G, Ip M, Westh H, Skov R, Struelens M J, Goering R V, Strommenger B, Weller A, Witte W, Achtman M. 2008. Frequent emergence and limited geographic dispersal of methicillin-resistant *Staphylococcus aureus*. Proc Natl Acad Sci USA 105: 14130-14135.
12. Driebe E M, Sahl J W, Roe C, Bowers J R, Schupp J M, Gillece J D, Kelley E, Price L B, Pearson T R, Hepp C M, Brzoska P M, Cummings C A, Furtado M R, Andersen P S, Stegger M, Engelthaler D M, Keim P S. 2015. Using Whole Genome Analysis to Examine Recombination across Diverse Sequence Types of *Staphylococcus aureus*. PloS One 10:e0130955.
13. Strommenger B, Bartels M D, Kurt K, Layer F, Rohde S M, Boye K, Westh H, Witte W, De Lencastre H, Nubel U. 2014. Evolution of methicillin-resistant *Staphylococcus aureus* towards increasing resistance. J Antimicrob Chemother 69:616-622.
14. Engelthaler D M, Kelley E, Driebe E M, Bowers J, Eberhard C F, Trujillo J, Decruyenaere F, Schupp J M, Mossong J, Keim P, Even J. 2013. Rapid and robust phylotyping of spa t003, a dominant MRSA clone in Luxembourg and other European countries. BMC Infect Dis 13:339.
15. Monecke S, Coombs G, Shore A C, Coleman D C, Akpaka P, Borg M, Chow H, Ip M, Jatzwauk L, Jonas D, Kadlec K, Kearns A, Laurent F, O'Brien F G, Pearson J, Ruppelt A, Schwarz S, Scicluna E, Slickers P, Tan H L, Weber S, Ehricht R. 2011. A field guide to pandemic, epidemic and sporadic clones of methicillin-resistant *Staphylococcus aureus*. PloS One 6:e17936.
16. Jamrozy D, Harris S R, Naglaa M, Peacock S J, Tan C Y, Parkhill J, Anderson A S, Holden M T. 2016. Pan-genomic perspective on the evolution of the *Staphylococcus aureus* USA300 epidemic. Microbial Genomics.
17. Benson M A, Ohneck E A, Ryan C, Alonzo F, 3rd, Smith H, Narechania A, Kolokotronis S O, Satola S W, Uhlemann A C, Sebra R, Deikus G, Shopsin B, Planet P J, Torres V J. 2014. Evolution of hypervirulence by a MRSA clone through acquisition of a transposable element. Mol Microbiol 93:664-681.
18. Boyle-Vavra S, Li X, Alam M T, Read T D, Sieth J, Cywes-Bentley C, Dobbins G, David M Z, Kumar N, Eells S J, Miller L G, Boxrud D J, Chambers H F, Lynfield R, Lee J C, Daum R S. 2015. USA300 and USA500 clonal lineages of *Staphylococcus aureus* do not produce a capsular polysaccharide due to conserved mutations in the cap5 locus. Mbio 6.
19. Keim P, Van Ert M N, Pearson T, Vogler A J, Huynh L Y, Wagner D M. 2004. Anthrax molecular epidemiology and forensics: using the appropriate marker for different evolutionary scales. Infect Genet Evol 4:205-213.
20. Nimmo G R. 2012. USA300 abroad: global spread of a virulent strain of community-associated methicillin-resistant *Staphylococcus aureus*. Clin Microbiol Infect 18:725-734.
21. Sanches I S, Ramirez M, Troni H, Abecassis M, Padua M, Tomasz A, de Lencastre H. 1995. Evidence for the geographic spread of a methicillin-resistant *Staphylococcus aureus* clone between Portugal and Spain. J Clin Microbiol 33:1243-1246.
22. de Lencastre H, Chung M, Westh H. 2000. Archaic strains of methicillin-resistant *Staphylococcus aureus*: molecular and microbiological properties of isolates from the 1960s in Denmark. Microb Drug Resist 6:1-10.
23. Stegger M, Wirth T, Andersen P S, Skov R L, De Grassi A, Simoes P M, Tristan A, Petersen A, Aziz M, Kiil K, Cirkovic I, Udo E E, del Campo R, Vuopio-Varkila J, Ahmad N, Tokajian S, Peters G, Schaumburg F, Olsson-Liljequist B, Givskov M, Driebe E E, Vigh H E, Shittu A, Ramdani-Bougessa N, Rasigade J P, Price L B, Vandenesch F, Larsen A R, Laurent F. 2014. Origin and evolution of European community-acquired methicillin-resistant *Staphylococcus aureus*. Mbio 5:e01044-01014.
24. Sahl J W, Lemmer D, Travis J, Schupp J M, Gillece J D, Aziz M, Driebe E M, Drees K P, Hicks N D, Williamson C H D, Hepp C M, Smith D E, Roe C, Engelthaler D M, Wagner D M, Keim P. 2016. NASP: an accurate, rapid method for the identification of SNPs in WGS datasets that supports flexible input and output formats. Microbial Genomics 2:e000074.
25. McKenna A, Hanna M, Banks E, Sivachenko A, Cibulskis K, Kernytsky A, Garimella K, Altshuler D, Gabriel S, Daly M, DePristo M A. 2010. The Genome Analysis Toolkit: a MapReduce framework for analyzing next-generation DNA sequencing data. Genome Res 20:1297-1303.
26. Delcher A L, Salzberg S L, Phillippy A M. 2003. Using MUMmer to identify similar regions in large sequence sets. Curr Protoc Bioinformatics Chapter 10:Unit 10 13.
27. Tamura K, Peterson D, Peterson N, Stecher G, Nei M, Kumar S. 2011. MEGA5: molecular evolutionary genetics analysis using maximum likelihood, evolutionary distance, and maximum parsimony methods. Mol Biol Evol 28:2731-2739.
28. Letunic I, Bork P. 2011. Interactive Tree Of Life v2: online annotation and display of phylogenetic trees made easy. Nucleic Acids Res 39:W475-478.
29. Albrecht V S, Limbago B M, Moran G J, Krishnadasan A, Gorwitz R J, McDougal L K, Talan D A, Group EMINS. 2015. *Staphylococcus aureus* Colonization and Strain Type at Various Body Sites among Patients with a Closed Abscess and Uninfected Controls at U.S. Emergency Departments. J Clin Microbiol 53:3478-3484.
30. Inouye M, Dashnow H, Raven L A, Schultz M B, Pope B J, Tomita T, Zobel J, Holt K E. 2014. SRST2: Rapid genomic surveillance for public health and hospital microbiology labs. Genome Med 6:90.
31. Chen L, Mediavilla J R, Oliveira D C, Willey B M, de Lencastre H, Kreiswirth B N. 2009. Multiplex real-time PCR for rapid Staphylococcal cassette chromosome mec typing. J Clin Microbiol 47:3692-3706.
32. Bankevich A, Nurk S, Antipov D, Gurevich A A, Dvorkin M, Kulikov A S, Lesin V M, Nikolenko S I, Pham S, Prjibelski A D, Pyshkin A V, Sirotkin A V, Vyahhi N, Tesler G, Alekseyev M A, Pevzner P A. 2012. SPAdes: a new genome assembly algorithm and its applications to single-cell sequencing. J Comput Biol 19:455-477.
33. Stajich J E, Block D, Boulez K, Brenner S E, Chervitz S A, Dagdigian C, Fuellen G, Gilbert J G, Korf I, Lapp H, Lehvaslaiho H, Matsalla C, Mungall C J, Osborne B I, Pocock M R, Schattner P, Senger M, Stein L D, Stupka E, Wilkinson M D, Birney E. 2002. The Bioperl toolkit: Perl modules for the life sciences. Genome Res 12:1611-1618.

34. Kondo Y, Ito T, Ma X X, Watanabe S, Kreiswirth B N, Etienne J, Hiramatsu K. 2007. Combination of multiplex PCRs for staphylococcal cassette chromosome mec type assignment: rapid identification system for mec, ccr, and major differences in junkyard regions. Antimicrob Agents Chemother 51:264-274.

35. Kitchel B, Rasheed J K, Endimiani A, Hujer A M, Anderson K F, Bonomo R A, Patel J B. 2010. Genetic factors associated with elevated carbapenem resistance in KPC-producing *Klebsiella* 49ethicill. Antimicrob Agents Chemother 54:4201-4207.

36. Aanensen D M, Feil E J, Holden M T, Dordel J, Yeats C A, Fedosejev A, Goater R, Castillo-Ramirez S, Corander J, Colijn C, Chlebowicz M A, Schouls L, Heck M, Pluister G, Ruimy R, Kahlmeter G, Ahman J, Matuschek E, Friedrich A W, Parkhill J, Bentley S D, Spratt B G, Grundmann H, European SRLWG. 2016. Whole-Genome Sequencing for Routine Pathogen Surveillance in Public Health: a Population Snapshot of Invasive *Staphylococcus aureus* in Europe. Mbio 7.

37. Goering R V, McDougal L K, Fosheim G E, Bonnstetter K K, Wolter D J, Tenover F C. 2007. Epidemiologic distribution of the arginine catabolic mobile element among selected methicillin-resistant and methicillin-susceptible *Staphylococcus aureus* isolates. J Clin Microbiol 45:1981-1984.

38. Diep B A, Carleton H A, Chang R F, Sensabaugh G F, Perdreau-Remington F. 2006. Roles of 34 virulence genes in the evolution of hospital- and community-associated strains of methicillin-resistant *Staphylococcus aureus*. J Infect Dis 193:1495-1503.

39. Planet P J, LaRussa S J, Dana A, Smith H, Xu A, Ryan C, Uhlemann A C, Boundy S, Goldberg J, Narechania A, Kulkarni R, Ratner A J, Geoghegan J A, Kolokotronis S O, Prince A. 2013. Emergence of the epidemic methicillin-resistant *Staphylococcus aureus* strain USA300 coincides with horizontal transfer of the arginine catabolic mobile element and speG-mediated adaptations for survival on skin. Mbio 4:e00889-00813.

40. Roe C C, Horn K S, Driebe E M, Bowers J, Terriquez J A, Keim P, Engelthaler D M. 2016. Whole genome SNP typing to investigate methicillin-resistant *Staphylococcus aureus* carriage in a health-care provider as the source of multiple surgical site infections. Hereditas 153.

41. Holden M T, Hsu L Y, Kurt K, Weinert L A, Mather A E, Harris S R, Strommenger B, Layer F, Witte W, de Lencastre H, Skov R, Westh H, Zemlickova H, Coombs G, Kearns A M, Hill R L, Edgeworth J, Gould I, Gant V, Cooke J, Edwards G F, McAdam P R, Templeton K E, McCann A, Zhou Z, Castillo-Ramirez S, Feil E J, Hudson L O, Enright M C, Balloux F, Aanensen D M, Spratt B G, Fitzgerald J R, Parkhill J, Achtman M, Bentley S D, Nubel U. 2013. A genomic portrait of the emergence, evolution, and global spread of a methicillin-resistant *Staphylococcus aureus* pandemic. Genome Res 23:653-664.

42. Kurt K, Rasigade J P, Laurent F, Goering R V, Zemlickova H, Machova I, Struelens M J, Zautner A E, Holtfreter S, Broker B, Ritchie S, Reaksmey S, Limmathurotsakul D, Peacock S J, Cuny C, Layer F, Witte W, Nubel U. 2013. Subpopulations of *Staphylococcus aureus* clonal complex 121 are associated with distinct clinical entities. PloS One 8:e58155.

43. McAdam P R, Templeton K E, Edwards G F, Holden M T, Feil E J, Aanensen D M, Bargawi H J, Spratt B G, Bentley S D, Parkhill J, Enright M C, Holmes A, Girvan E K, Godfrey P A, Feldgarden M, Kearns A M, Rambaut A, Robinson D A, Fitzgerald J R. 2012. Molecular tracing of the emergence, adaptation, and transmission of hospital-associated methicillin-resistant *Staphylococcus aureus*. Proc Natl Acad Sci USA 109:9107-9112.

44. Bowers J R, Lemmer D, Sahl J W, Pearson T, Driebe E M, Wojack B, Saubolle M A, Engelthaler D M, Keim P. 2016. KlebSeq: A Diagnostic Tool for Surveillance, Detection, and Monitoring of *Klebsiella* 50ethicill. J Clin Microbiol doi:10.1128/JCM.00927-16.

45. See I, Gualandi N, Dumyati G, Koeck M, Lynfield R, Pasutti L, Schaffner W, Wright D, Magill S S. 2015. Public Health Importance of Methicillin-Sensitive *Staphylococcus aureus* (MSSA): Results From Pilot Surveillance in Five Counties, 2014-2015. Open Forum Infectious Diseases 2.

46. David M Z, Boyle-Vavra S, Zychowski D L, Daum R S. 2011. Methicillin-susceptible *Staphylococcus aureus* as a predominantly healthcare-associated pathogen: a possible reversal of roles? PloS One 6:e18217.

47. Miko B A, Hafer C A, Lee C J, Sullivan S B, Hackel M A, Johnson B M, Whittier S, Della-Latta P, Uhlemann A C, Lowy F D. 2013. Molecular characterization of methicillin-susceptible *Staphylococcus aureus* clinical isolates in the United States, 2004 to 2010. J Clin Microbiol 51:874-879.

48. Enright M C, Robinson D A, Randle G, Feil E J, Grundmann H, Spratt B G. 2002. The evolutionary history of methicillin-resistant *Staphylococcus aureus* (MRSA). Proc Natl Acad Sci USA 99:7687-7692.

49. Grundmann H, Aanensen D M, van den Wijngaard C C, Spratt B G, Harmsen D, Friedrich A W, European Staphylococcal Reference Laboratory Working G. 2010. Geographic distribution of *Staphylococcus aureus* causing invasive infections in Europe: a molecular-epidemiological analysis. PloS Med 7:e1000215.

50. Huang J, Ye M, Ding H, Guo Q, Ding B, Wang M. 2013. Prevalence of fusB in *Staphylococcus aureus* clinical isolates. J Med Microbiol 62:1199-1203.

51. Zheng B, Jiang S, Xu Z, Xiao Y, Li L. 2015. Severe infective endocarditis with systemic embolism due to community associated methicillin-resistant *Staphylococcus aureus* ST630. Braz J Infect Dis 19:85-89.

52. Gu F F, Hou Q, Yang H H, Zhu Y Q, Guo X K, Ni Y X, Han L Z. 2015. Characterization of *Staphylococcus aureus* Isolated from Non-Native Patients with Skin and Soft Tissue Infections in Shanghai. PloS One 10:e0123557.

53. Jackson B R, Tarr C, Strain E, Jackson K A, Conrad A, Carleton H, Katz L S, Stroika S, Gould L H, Mody R K, Silk B J, Beal J, Chen Y, Timme R, Doyle M, Fields A, Wise M, Tillman G, Defibaugh-Chavez S, Kucerova Z, Sabol A, Roache K, Trees E, Simmons M, Wasilenko J, Kubota K, Pouseele H, Klimke W, Besser J, Brown E, Allard M, Gerner-Smidt P. 2016. Implementation of Nationwide Real-time Whole-genome Sequencing to Enhance Listeriosis Outbreak Detection and Investigation. Clin Infect Dis 63:380-386.

54. Bergholz T M, den Bakker H C, Katz L S, Silk B J, Jackson K A, Kucerova Z, Joseph L A, Turnsek M, Gladney L M, Halpin J L, Xavier K, Gossack J, Ward T J, Frace M, Tarr C L. 2016. Determination of Evolutionary Relationships of Outbreak-Associated *Listeria monocytogenes* Strains of Serotypes ½a and ½b by Whole-Genome Sequencing. Appl Environ Microbiol 82:928-938.

55. Deng X, Shariat N, Driebe E M, Roe C C, Tolar B, Trees E, Keim P, Zhang W, Dudley E G, Fields P I, Engelthaler D M. 2015. Comparative analysis of subtyping methods against a whole-genome-sequencing standard for *Salmonella enterica* serotype *Enteritidis*. J Clin Microbiol 53:212-218.
56. Tenover F C, McDougal L K, Goering R V, Killgore G, Projan S J, Patel J B, Dunman P M. 2006. Characterization of a strain of community-associated methicillin-resistant *Staphylococcus aureus* widely disseminated in the United States. J Clin Microbiol 44:108-118.
57. Bowers J R, Kitchel B, Driebe E M, MacCannell D R, Roe C, Lemmer D, de Man T, Rasheed J K, Engelthaler D M, Keim P, Limbago B M. 2015. Genomic Analysis of the Emergence and Rapid Global Dissemination of the Clonal Group 258 *Klebsiella* 51 ethicill Pandemic. PloS One 10:e0133727.
58. Engelthaler D M, Valentine M, Bowers J, Pistole J, Driebe E M, Terriquez J, Nienstadt L, Carroll M, Schumacher M, Ormsby M E, Brady S, Livar E, Yazzie D, Waddell V, Peoples M, Komatsu K, Keim P. 2016. Hypervirulent emm59 Clone in Invasive Group A *Streptococcus* Outbreak, Southwestern United States. Emerg Infect Dis 22:734-738.
59. Howden B P, Seemann T, Harrison P F, McEvoy C R, Stanton J A, Rand C J, Mason C W, Jensen S O, Firth N, Davies J K, Johnson P D, Stinear T P. 2010. Complete genome sequence of *Staphylococcus aureus* strain JKD6008, an ST239 clone of methicillin-resistant *Staphylococcus aureus* with intermediate-level vancomycin resistance. J Bacteriol 192:5848-5849.
60. Li Y, Cao B, Zhang Y, Zhou J, Yang B, Wang L. 2011. Complete genome sequence of *Staphylococcus aureus* T0131, an ST239-MRSA-SCCmec type III clone isolated in China. J Bacteriol 193:3411-3412.
61. Holden M T, Lindsay J A, Corton C, Quail M A, Cockfield J D, Pathak S, Batra R, Parkhill J, Bentley S D, Edgeworth J D. 2010. Genome sequence of a recently emerged, highly transmissible, multi-antibiotic- and antiseptic-resistant variant of methicillin-resistant *Staphylococcus aureus*, sequence type 239 (TW). J Bacteriol 192:888-892.
62. Ito T, Katayama Y, Asada K, Mori N, Tsutsumimoto K, Tiensasitorn C, Hiramatsu K. 2001. Structural comparison of three types of staphylococcal cassette chromosome mec integrated in the chromosome in methicillin-resistant *Staphylococcus aureus*. Antimicrob Agents Chemother 45:1323-1336.
63. Suzuki E, Kuwahara-Arai K, Richardson J F, Hiramatsu K. 1993. Distribution of mec regulator genes in methicillin-resistant *Staphylococcus* clinical strains. Antimicrob Agents Chemother 37:1219-1226.
64. Chung M, de Lencastre H, Matthews P, Tomasz A, Adamsson I, Aires de Sousa M, Camou T, Cocuzza C, Corso A, Couto I, Dominguez A, Gniadkowski M, Goering R, Gomes A, Kikuchi K, Marchese A, Mato R, Melter O, Oliveira D, Palacio R, Sa-Leao R, Santos Sanches I, Song J H, Tassios P T, Villari P, Multilaboratory Project C. 2000. Molecular typing of methicillin-resistant *Staphylococcus aureus* by pulsed-field gel electrophoresis: comparison of results obtained in a multilaboratory effort using identical protocols and MRSA strains. Microb Drug Resist 6:189-198.
65. Crisostomo M I, Westh H, Tomasz A, Chung M, Oliveira D C, de Lencastre H. 2001. The evolution of methicillin resistance in *Staphylococcus aureus*: similarity of genetic backgrounds in historically early methicillin-susceptible and -resistant isolates and contemporary epidemic clones. Proc Natl Acad Sci USA 98:9865-9870.
66. Christianson S, Golding G R, Campbell J, Canadian Nosocomial Infection Surveillance P, Mulvey M R. 2007. Comparative genomics of Canadian epidemic lineages of methicillin-resistant *Staphylococcus aureus*. J Clin Microbiol 45:1904-1911.
67. Zhang K, McClure J A, Elsayed S, Conly J M. 2009. Novel staphylococcal cassette chromosome mec type, tentatively designated type VIII, harboring class A mec and type 4 ccr gene complexes in a Canadian epidemic strain of methicillin-resistant *Staphylococcus aureus*. Antimicrob Agents Chemother 53:531-540.
68. Diep B A, Gill S R, Chang R F, Phan T H, Chen J H, Davidson M G, Lin F, Lin J, Carleton H A, Mongodin E F, Sensabaugh G F, Perdreau-Remington F. 2006. Complete genome sequence of USA300, an epidemic clone of community-acquired 52ethicillin-resistant *Staphylococcus aureus*. Lancet 367:731-739.
69. Gonzalez B E, Martinez-Aguilar G, Hulten K G, Hammerman W A, Coss-Bu J, Avalos-Mishaan A, Mason E O, Jr., Kaplan S L. 2005. Severe Staphylococcal sepsis in adolescents in the era of community-acquired methicillin-resistant *Staphylococcus aureus*. Pediatrics 115:642-648.
70. Highlander S K, Hulten K G, Qin X, Jiang H, Yerrapragada S, Mason E O, Jr., Shang Y, Williams T M, Fortunov R M, Liu Y, Igboeli O, Petrosino J, Tirumalai M, Uzman A, Fox G E, Cardenas A M, Muzny D M, Hemphill L, Ding Y, Dugan S, Blyth P R, Buhay C J, Dinh H H, Hawes A C, Holder M, Kovar C L, Lee S L, Liu W, Nazareth L V, Wang Q, Zhou J, Kaplan S L, Weinstock G M. 2007. Subtle genetic changes enhance virulence of methicillin resistant and sensitive *Staphylococcus aureus*. BMC Microbiol 7:99.
71. Planet P J, Diaz L, Kolokotronis S O, Narechania A, Reyes J, Xing G, Rincon S, Smith H, Panesso D, Ryan C, Smith D P, Guzman M, Zurita J, Sebra R, Deikus G, Nolan R L, Tenover F C, Weinstock G M, Robinson D A, Arias C A. 2015. Parallel Epidemics of Community-Associated Methicillin-Resistant *Staphylococcus aureus* USA300 Infection in North and South America. J Infect Dis 212:1874-1882.
72. Glaser P, Martins-Simoes P, Villain A, Barbier M, Tristan A, Bouchier C, Ma L, Bes M, Laurent F, Guillemot D, Wirth T, Vandenesch F. 2016. Demography and Intercontinental Spread of the USA300 Community-Acquired Methicillin-Resistant *Staphylococcus aureus* Lineage. Mbio 7:e02183-02115.
73. Uhlemann A C, Dordel J, Knox J R, Raven K E, Parkhill J, Holden M T, Peacock S J, Lowy F D. 2014. Molecular tracing of the emergence, diversification, and transmission of *S. aureus* sequence type 8 in a New York community. Proc Natl Acad Sci USA 111:6738-6743.
74. Rossi F, Diaz L, Wollam A, Panesso D, Zhou Y, Rincon S, Narechania A, Xing G, Di Gioia T S, Doi A, Tran T T, Reyes J, Munita J M, Carvajal L P, Hernandez-Roldan A, Brandao D, van der Heij den I M, Murray B E, Planet P J, Weinstock G M, Arias C A. 2014. Transferable vancomycin resistance in a community-associated MRSA lineage. N Engl J Med 370:1524-1531.
75. Nguyen L T, Schmidt H A, von Haeseler A, Minh B Q. 2015. IQ-TREE: a fast and effective stochastic algorithm for estimating maximum-likelihood phylogenies. Mol Biol Evol 32:268-274.
76. Coombs G W, Pearson J C, O'Brien F G, Murray R J, Grubb W B, Christiansen K J. 2006. Methicillin-resistant *Staphylococcus aureus* clones, Western Australia. Emerg Infect Dis 12:241-247.

77. Campanile F, Bongiorno D, Borbone S, Stefani S. 2009. Hospital-associated methicillin-resistant *Staphylococcus aureus* (HA-MRSA) in Italy. Ann Clin Microbiol Antimicrob 8:22.
78. Noto M J, Kreiswirth B N, Monk A B, Archer G L. 2008. Gene acquisition at the insertion site for SCCmec, the genomic island conferring methicillin resistance in *Staphylococcus aureus*. J Bacteriol 190:1276-1283.
79. Barbier F, Ruppe E, Hernandez D, Lebeaux D, Francois P, Felix B, Desprez A, Maiga A, Woerther P L, Gaillard K, Jeanrot C, Wolff M, Schrenzel J, Andremont A, Ruimy R. 2010. Methicillin-resistant coagulase-negative staphylococci in the community: high homology of SCCmec Iva between *Staphylococcus epidermidis* and major clones of methicillin-resistant *Staphylococcus aureus*. J Infect Dis 202:270-281.

What is claimed is:

1. A method of detecting the presence of a *Staphylococcus aureus* clonal complex 8 (CC8) strain, including Clade CC8f in a biological sample, comprising:
a. obtaining nucleic acids from the biological sample;
b. optionally amplifying the nucleic acids to produce at least one amplicon;
c. contacting the nucleic acids or the at least one amplicon with a SNP variant polynucleotide probe,
wherein:
the SNP variant polynucleotide probe is selected from the group consisting of:
i) 20-35 contiguous nucleotides of SEQ ID NO: 58, an RNA equivalent, or a reverse complement thereof; and
ii) 13-25 contiguous nucleotides of SEQ ID NO: 59, an RNA equivalent, or a reverse complement thereof; and
d. detecting specific hybridization of the SNP variant probe to the nucleic acids or to the at least one amplicon, thereby detecting the presence of Clade CC8f.

2. The method of claim 1, further comprising:
e. contacting the nucleic acids or the at least one amplicon with a reference polynucleotide probe,
wherein:
the reference polynucleotide probe is selected from the group consisting of:
i) 20-35 contiguous nucleotides SEQ ID NO: 60, an RNA equivalent, or a reverse complement thereof; and
ii) 13-25 contiguous nucleotides SEQ ID NO: 61, an RNA equivalent, or a reverse complement thereof; and
f. detecting specific hybridization of the reference polynucleotide probe to the nucleic acids or to the at least one amplicon, thereby detecting the presence of a *Staphylococcus aureus* strain lacking a polymorphism specific to Clade CC8f.

3. The method of claim 1, wherein the SNP variant polynucleotide probe is SEQ ID NO: 28.

4. The method of claim 1, further comprising:
e. contacting the nucleic acids or the at least one amplicon with a second SNP variant polynucleotide probe,
wherein:
the second SNP variant polynucleotide probe is selected from the group consisting of:
i) 20-35 contiguous nucleotides of SEQ ID NO: 34, an RNA equivalent, or a reverse complement thereof; and
ii) 13-25 contiguous nucleotides of SEQ ID NO: 35, an RNA equivalent, or a reverse complement thereof; and
f. detecting specific hybridization of the second SNP variant probe to the nucleic acids or to the at least one amplicon, thereby detecting the presence of Clade CC8 when present in the biological sample.

5. The method of claim 1, further comprising:
e. contacting the nucleic acids or the at least one amplicon with a second reference polynucleotide probe,
wherein:
the second reference polynucleotide probe is selected from the group consisting of:
i) 20-35 contiguous nucleotides of SEQ ID NO: 36, an RNA equivalent, or a reverse complement thereof; and
ii) 13-25 contiguous nucleotides of SEQ ID NO: 37, an RNA equivalent, or a reverse complement thereof; and
f. detecting specific hybridization of the second reference polynucleotide probe to the nucleic acids or to the at least one amplicon, thereby detecting the presence of a *Staphylococcus aureus* strain lacking a polymorphism specific to Clade CC8 when present in the biological sample.

6. The method of claim 1, further comprising:
e. contacting the nucleic acids or the at least one amplicon with a second SNP variant polynucleotide probe,
wherein:
the second SNP variant polynucleotide probe is selected from the group consisting of:
i) 20-35 contiguous nucleotides of SEQ ID NO: 38, an RNA equivalent, or a reverse complement thereof; and
ii) 13-25 contiguous nucleotides of SEQ ID NO: 39, an RNA equivalent, or a reverse complement thereof; and
f. detecting specific hybridization of the second SNP variant probe to the nucleic acids or to the at least one amplicon, thereby detecting the presence of Inner Clade CC8 when present in the biological sample.

7. The method of claim 1, further comprising:
e. contacting the nucleic acids or the at least one amplicon with a second reference polynucleotide probe,
wherein:
the second reference polynucleotide probe is selected from the group consisting of:
i) 20-35 contiguous nucleotides of SEQ ID NO: 40, an RNA equivalent, or a reverse complement thereof; and ii) 13-25 contiguous nucleotides of SEQ ID NO: 41, an RNA equivalent, or a reverse complement thereof; and
f. detecting specific hybridization of the second reference polynucleotide probe to the nucleic acids or to the at least one amplicon, thereby detecting the presence of a *Staphylococcus aureus* strain lacking a polymorphism specific to Inner Clade CC8 when present in the biological sample.

8. The method of claim 1, further comprising:
e. contacting the nucleic acids or the at least one amplicon with a second SNP variant polynucleotide probe, wherein:
the second SNP variant polynucleotide probe is selected from the group consisting of:
i) 20-35 contiguous nucleotides of SEQ ID NO: 42, an RNA equivalent, or a reverse complement thereof; and
ii) 13-25 contiguous nucleotides of SEQ ID NO: 43, an RNA equivalent, or a reverse complement thereof; and
f. detecting specific hybridization of the second SNP variant probe to the nucleic acids or to the at least one amplicon, thereby detecting the presence of Clade CC8a when present in the biological sample.

9. The method of claim 1, further comprising:
e. contacting the nucleic acids or the at least one amplicon with a second reference polynucleotide probe, wherein:
the second reference polynucleotide probe is selected from the group consisting of:
i) 20-35 contiguous nucleotides of SEQ ID NO: 44, an RNA equivalent, or a reverse complement thereof; and
ii) 13-25 contiguous nucleotides of SEQ ID NO: 45, an RNA equivalent, or a reverse complement thereof; and
f. detecting specific hybridization of the second reference polynucleotide probe to the nucleic acids or to the at least one amplicon, thereby detecting the presence of a *Staphylococcus aureus* strain lacking a polymorphism specific to Clade CC8 when present in the biological sample.

10. The method of claim 1, further comprising:
e. contacting the nucleic acids or the at least one amplicon with a second SNP variant polynucleotide probe, wherein:
the second SNP variant polynucleotide probe is selected from the group consisting of:
i) 20-35 contiguous nucleotides of SEQ ID NO: 46, an RNA equivalent, or a reverse complement thereof; and
ii) 13-25 contiguous nucleotides of SEQ ID NO: 47, an RNA equivalent, or a reverse complement thereof; and
f. detecting specific hybridization of the second SNP variant probe to the nucleic acids or to the at least one amplicon, thereby detecting the presence of Clade CC8b when present in the biological sample.

11. The method of claim 10, wherein the second SNP variant probe is SEQ ID NO. 16.

12. The method of claim 1, further comprising:
e. contacting the nucleic acids or the at least one amplicon with a second reference polynucleotide probe, wherein:
the second reference polynucleotide probe is selected from the group consisting of:
i) 20-35 contiguous nucleotides of SEQ ID NO: 48, an RNA equivalent, or a reverse complement thereof; and
ii) 13-25 contiguous nucleotides of SEQ ID NO: 49, an RNA equivalent, or a reverse complement thereof; and
f. detecting specific hybridization of the second reference polynucleotide probe to the nucleic acids or to the at least one amplicon, thereby detecting the presence of a *Staphylococcus aureus* strain lacking a polymorphism specific to Clade CC8b when present in the biological sample.

13. The method of claim 1, further comprising:
e. contacting the nucleic acids or the at least one amplicon with a second SNP variant polynucleotide probe, wherein:
the second SNP variant polynucleotide probe is selected from the group consisting of:
i) 20-35 contiguous nucleotides of SEQ ID NO: 50, an RNA equivalent, or a reverse complement thereof; and
ii) 13-25 contiguous nucleotides of SEQ ID NO: 51, an RNA equivalent, or a reverse complement thereof; and
f. detecting specific hybridization of the second SNP variant probe to the nucleic acids or to the at least one amplicon, thereby detecting the presence of Clade CC8c when present in the biological sample.

14. The method of claim 13, wherein the second SNP variant probe is SEQ ID NO. 20.

15. The method of claim 1, further comprising:
e. contacting the nucleic acids or the at least one amplicon with a second reference polynucleotide probe, wherein:
the second reference polynucleotide probe is selected from the group consisting of:
i) 20-35 contiguous nucleotides of SEQ ID NO: 52, an RNA equivalent, or a reverse complement thereof; and
ii) 13-25 contiguous nucleotides of SEQ ID NO: 53, an RNA equivalent, or a reverse complement thereof; and
f. detecting specific hybridization of the second reference polynucleotide probe to the nucleic acids or to the at least one amplicon, thereby detecting the presence of a *Staphylococcus aureus* strain lacking a polymorphism specific to Clade CC8c when present in the biological sample.

16. The method of claim 1, further comprising:
e. contacting the nucleic acids or the at least one amplicon with a second SNP variant polynucleotide probe, wherein:
the second SNP variant polynucleotide probe is selected from the group consisting of:
i) 20-35 contiguous nucleotides of SEQ ID NO: 54, an RNA equivalent, or a reverse complement thereof; and
ii) 13-25 contiguous nucleotides of SEQ ID NO: 55, an RNA equivalent, or a reverse complement thereof; and
f. detecting specific hybridization of the second SNP variant probe to the nucleic acids or to the at least one amplicon, thereby detecting the presence of Clade CC8e when present in the biological sample.

17. The method of claim 16, wherein the second SNP variant probe is SEQ ID NO. 24.

18. The method of claim 1, further comprising:
e. contacting the nucleic acids or the at least one amplicon with a second reference polynucleotide probe,
wherein:
  the second reference polynucleotide probe is selected from the group consisting of:
   i) 20-35 contiguous nucleotides of SEQ ID NO: 56, an RNA equivalent, or a reverse complement thereof; and
   ii) 13-25 contiguous nucleotides of SEQ ID NO: 57, an RNA equivalent, or a reverse complement thereof; and
f. detecting specific hybridization of the second reference polynucleotide probe to the nucleic acids or to the at least one amplicon, thereby detecting the presence of a *Staphylococcus aureus* strain lacking a polymorphism specific to Clade CC8e when present in the biological sample.

19. The method of claim 1, further comprising:
e. contacting the nucleic acids or the at least one amplicon with a second SNP variant polynucleotide probe,
wherein:
  the second SNP variant polynucleotide probe is selected from the group consisting of:
   i) 20-35 contiguous nucleotides of SEQ ID NO: 62, an RNA equivalent, or a reverse complement thereof; and
   ii) 13-25 contiguous nucleotides of SEQ ID NO: 63, an RNA equivalent, or a reverse complement thereof; and
f. detecting specific hybridization of the second SNP variant probe to the nucleic acids or to the at least one amplicon, thereby detecting the presence of ST239 when present in the biological sample.

20. The method of claim 1, further comprising:
e. contacting the nucleic acids or the at least one amplicon with at least seven additional SNP variant polynucleotide probes,
wherein:
the at least seven additional SNP variant polynucleotide probes are selected from the group consisting of:
   i) 20-35 contiguous nucleotides of SEQ ID NOS: 34, 36, 38, 40, 42, 44, 46, 48, 50, 52, 54, 56, 62, 64 an RNA equivalent, or a reverse complement thereof; and
   ii) 13-25 contiguous nucleotides of SEQ ID NOS: 35, 37, 39, 41, 43, 45, 47, 49, 51, 53, 55, 57, 63, 65 an RNA equivalent, or a reverse complement thereof; and
f. detecting specific hybridization of the at least seven additional SNP variant probes to the nucleic acids or to the at least one amplicon, thereby further detecting the presence of ST239, Clade CC8, Clade CC8b, Clade CC8c, Clade CC8e, Inner Clade CC8 when present in the biological sample.

\* \* \* \* \*